United States Patent
Leusen et al.

(10) Patent No.: US 11,866,511 B2
(45) Date of Patent: Jan. 9, 2024

(54) ANTI-GD2 ANTIBODY

(71) Applicant: TigaTX, Inc., Westerly, RI (US)

(72) Inventors: Jeanette Henrica Wilhelmina Leusen, Utrecht (NL); Johannes Gerardus Maria Evers, Utrecht (NL)

(73) Assignee: TigaTX, Inc., Boston, MA (US)

( * ) Notice: Subject to any disclaimer, the term of this patent is extended or adjusted under 35 U.S.C. 154(b) by 564 days.

(21) Appl. No.: 16/825,563

(22) Filed: Mar. 20, 2020

(65) Prior Publication Data

US 2020/0283541 A1 Sep. 10, 2020

Related U.S. Application Data

(63) Continuation of application No. PCT/NL2018/050629, filed on Sep. 21, 2018.

(30) Foreign Application Priority Data

Sep. 21, 2017 (EP) .................... 17192476

(51) Int. Cl.
| | | |
|---|---|---|
| *C07K 16/30* | (2006.01) | |
| *A61K 39/395* | (2006.01) | |
| *A61K 39/00* | (2006.01) | |
| *A61P 35/00* | (2006.01) | |
| *A61K 31/203* | (2006.01) | |
| *A61K 38/19* | (2006.01) | |

(52) U.S. Cl.
CPC ........ *C07K 16/3084* (2013.01); *A61K 31/203* (2013.01); *A61K 38/193* (2013.01); *A61K 39/39558* (2013.01); *A61P 35/00* (2018.01); *A61K 2039/505* (2013.01); *C07K 2317/21* (2013.01); *C07K 2317/24* (2013.01); *C07K 2317/522* (2013.01); *C07K 2317/526* (2013.01); *C07K 2317/53* (2013.01); *C07K 2317/565* (2013.01); *C07K 2317/732* (2013.01); *C07K 2317/734* (2013.01)

(58) Field of Classification Search
CPC ........ A61K 39/39558; A61K 2039/505; C07K 16/3084
See application file for complete search history.

(56) References Cited

U.S. PATENT DOCUMENTS

| | | |
|---|---|---|
| 6,284,536 B1 | 9/2001 | Morrison et al. |
| 8,236,561 B2 | 8/2012 | Jones et al. |
| 8,313,730 B2 | 11/2012 | Simon et al. |
| 9,505,848 B2 | 11/2016 | Davis et al. |
| 9,522,184 B2 | 12/2016 | Von Gunten et al. |
| 9,573,996 B2 | 2/2017 | Ariaans et al. |
| 9,580,501 B2 | 2/2017 | Ariaans et al. |
| 9,593,147 B2 | 3/2017 | Ito |
| 9,828,418 B2 | 11/2017 | El Menyawi et al. |
| 9,890,216 B2 | 2/2018 | Georgiou et al. |
| 2014/0170155 A1* | 6/2014 | Loibner ............. C07K 16/3084 424/139.1 |
| 2017/0058018 A2 | 3/2017 | Brown et al. |
| 2019/0365717 A1 | 12/2019 | Raaben et al. |

FOREIGN PATENT DOCUMENTS

| | | |
|---|---|---|
| WO | WO-2008049643 A2 | 5/2008 |
| WO | 2014006217 | 1/2014 |
| WO | 2015075194 A1 | 5/2015 |

OTHER PUBLICATIONS

Chintalacharuvu, K. R., et al. Hybrid IgA2/IgG1 Antibodies with Tailor-Made Effector Functions (Clinical Immunology vol. 101, No. 1, October, pp. 21-31, 2001) (Year: 2001).

Nimmerjahn, F. et al., FcgyR Dependent Mechanisms of Cytotoxic, Agonistic, and Neutralizing Antibody Activities (Trends in Immunology, Jun. 2015, vol. 36, No. 6 pp. 325-336) (Year: 2015).

Armour et al. Recombinant human IgG molecules lacking Fcgamma receptor I binding and monocyte triggering activities. Eur J Immunol 29(8):2613-2624 (1999).

Barker, Edward et al., Effect of a Chimeric Anti-Ganglioside GD2 Antibody on Cell-mediated Lysis of Human Neuroblastoma Cells, Cancer Res, vol. 51: p. 144-9.

Bate-Eva, Laurel et al., (2014), Newly-derived neuroblastoma cell lines propagated inserum-fre media recapitulate the genotype and phenotype of primary neuroblastoma tumours, European Journal of Cancer 50.3: 628-637.

Batova,Ayse et al., TheCh14.18-GM-CSF Fusion Protein Is Effective at Mediating Antibody-dependent Cellular Cytotoxicity and Complement-dependent Cytotoxicity inVitro, (1999) Clin Cancer Res vol. 5: p. 4259-63.

Beyer, T., et al. Serum-free production and purification of chimeric IgA antibodies, Journal of immunological methods 346.1 (2009): 26-37.

Bogenmann,E. (1996), A Metastatic Neuroblastoma Model in SCID Mice, Int. J. Cancer vol. 67:379.

Boross et al. IgA EGFR antibodies mediate tumour killing in vivo. EMBO Mol Med 5:1213-1226 (2013).

Boross et al. The in vivo mechanism of action of CD20 monoclonal antibodies depends on local tumor burden. Haematologica 96:1822-1830 (2011).

(Continued)

*Primary Examiner* — Elly-Gerald Stoica
(74) *Attorney, Agent, or Firm* — Greenberg Traurig, LLP

(57) ABSTRACT

The invention relates to anti-ganglioside GD2 antibodies that comprise an antibody variable domain and antibody constant domains, wherein the variable domain comprises a heavy and light chain variable region comprising respectively at least the CDR3 of the heavy chain variable region of antibody ch14.18 and at least the CDR3 of the light chain variable region of antibody ch14.18; and an IgA hinge and $C_H2$ domain and to methods of treatment of subjects with a GD2 positive tumor, preferably neuroblastoma with these antibodies.

7 Claims, 26 Drawing Sheets

Specification includes a Sequence Listing.

(56) References Cited

OTHER PUBLICATIONS

Boross, Peter et al., Mechanisms of action of CD20 antibodies, Am JCancer Res. 2012; 2(6):676-690. Published online Nov. 20, 2012.
Braekeveldt, Noemie et al., 2016 Neuroblastoma patient-derived orthotopic xenografts reflect the microenvironmental hallmarks of aggressive patient tumors, Cancer Lett. vol. 1;375(2):384-9. doi: 10.1016/j.canlet.2016.02.046.
Brandsma, Arianne et al.( 2015), Simultaneous Targeting of FcyRs and FcαRIEnhances Tumor Cell Killing, Cancer Immunol Res 3(12):1316-1324).
Bruchelt et al.(1989); Lysis of neuroblastoma cells by the ADCC-reaction: granulocytes of patients with chronic granulomatous disease are more effective than those of healthy donors, Immunol Lett 22(3): 217-220.
Bruhns et al. Specificity and Affinity of Human Fc Receptors and Their Polymorphic Variants for Human IgG Subclasses. Blood 113(16):3716-3725 (2009).
Chaplan et al. Quantitative assessment of tactile allodynia in the rat paw. J Neurosci Methods 53:55-63 (1994).
Cheung, Irene et al., Activation of Peripheral-Blood Granulocytes Is Strongly Correlated With Patient Outcome After Immunotherapy With Anti-GD2 Monoclonal Antibody and Granulocyte-Macrophage Colony-Stimulating Factor,2012, J Clin Oncol, vol. 30: p. 426-32.
Cheung, Nai-Kong V. at al (2014),Key Role for Myeloid Cells: Phase II Results of Anti-GD2 Antibody3F8 Plus Granulocyte-Macrophage Colony-Stimulating Factor for Chemoresistant Osteomedullary Neuroblastoma, Int J Cancer 135(9): 2199-2205).
Cheung, Nai-Kong V et al., 2012, Humanizing murine IgG3 anti-GD2 antibody m3F8substantially improves antibody-dependent cell-mediated cytotoxicity while retaining targeting in vivo, Oncoimmunology 1.4: 477-486.
Eijkelkamp, et al., "IL4-10 Fusion Protein Is a Novel Drug to Treat Persistent Inflammatory Pain" The Journal of Neuroscience, Jul. 13, 2016; 36(28):7353-7363.
Galluzi, Lorenzo et al., Trial Watch: Monoclonal Antibodies in Cancer Therapy, Jan./Feb. 2012, OncoImmunology, vol. 1, Issue 1, pp. 28-37.
Gillies et al., 1989, High-level expression of chimeric antibodies using adapted cDNA variableregion cassettes,J Immunol Methods, 125, p. 191-202.
Gilman et al.2009, Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group, J Clin Oncol 27(1): 85-91.
Golay, Josee et al., Glycoengineered CD20 antibody obinutuzumab activates neutrophils and mediates phagocytosis through CD16B more efficiently than rituximab, Immunobiology, Nov. 14, 2013, Blood (2013) 122 (20): 3482-3491, https://doi.org/10.1182/blood-2013-05-504043.
Hiemstra, Peter S. et al., Activation of the alternative pathway of complement by human serum IgA European Journal of immunology. 1987;17(3):321-6.
Idusogie, et al. Mapping of the C1q binding site on rituxan, a chimeric antibody with a human IgG1 Fc. J Immunol. Apr. 15, 2000;164(8):4178-84.
Idusogie.et al., Engineered Antibodies with Increased Activity to Recruit Complement, 2001. J Immunol.166(4):2571-5.
Jarvis et al., Human IgA1 initiates Compliment Mediated Killing of Neisseria Meningitis, J Immunol. 1989;143(5):1703-9.
Ladenstein et al 2013,Ch14.18 antibody produced in CHO cells in relapsed or refractory Stage 4 neuroblastoma patients A SIOPEN phase 1 study, MAbs 5(5): 801-809.
Leusen, Jeanette H.W., et al., IgA as therapeutic antibody, Molecular Immunology, vol. 68, Issue 1, Nov. 2015, pp. 35-39https://doi.org/10.1016/j.molimm.2015.09.005.
Lohse et al., 2016, An Anti-EGFR IgA That Displays Improved Pharmacokinetics and Myeloid Effector Cell Engagement In Vivo, Cancer Res 76(2): 403-417.

Lohse, Loew et al; Effector Mechanisms of IgA antibodies against CD20 include recruitment of myeloid cells for antibody dependent cell-mediated cytocity and complement-dependent cytocity, 2018; Br J Haematol 181(3): 413-417).
Mahiuddin et al., Engineering anti-GD2 Monoclonal Antibodies for Cancer Immunotherapy, 2014; FEBS letters588: 288-297.
Matthay et al., Treatment of High-Risk Neuroblastoma with Intensive Chemotherapy, Radiotherapy, Autologous Bone marrow Transplantation, and13-CIS-Retinoic Acid, 1999; New Engl. J. of Med vol. 341: pp. 1165-1173.
Meyer et al., 2016, Improved in vivo anti-tumor effects of IgA-Her2antibodies through half-life extension and serum exposure enhancement by FcRn targeting, MAbsvol. 8: pp. 87-98.
Mora, J, 2016, Dinutuximab for the treatment of pediatric patients with high-risk neuroblastoma, Expert review of clinical pharmacology, pp. 1-7; http://dx.doi.org/10.1586/17512433.2016.1160775.
Morrell et al, Metabolic Properties of Human IgA Subclasses, 1973, Clin Exp Immunol 13(4): 521-528.
Nassin et al 2018, Immune Reconstitution Following Autologous Stem Cell Transplantation in Patients with High-Risk Neuroblastoma at theTime of Immunotherapy, Biol Blood Marrow Transplant 24(3): 452-459).
Navid et al2014, Phase I Trial of a Novelanti-GD2 Monoclonal Antibody, Hu14.18K322A, Designed to Decrease Toxicity in Children With Refractory or Recurrent Neuroblastoma, J Clin Oncol 32(14): 1445-1452.
Pascal, Virginie et al., (2012) Anti-CD20 IgA Can Protect Mice Against Lymphoma Development: Evaluation of the Direct Impact of IgA and Cytotoxic Effector Recruitment on CD20 Target Cells, Haematologica, pp. 1686-1694 DOI: 10.3324/haematol.2011.061408 .
Pascal,et al., Activation of the guinea pig alternative complement pathway by mouse IgA immune complexes, J. Exp. Med., Rockefeller University Press, vol. 155, Jan. 1982, pp. 231-247.
Pfaffenbach et al., Activation of the Guinea Pig Alternative Complement Pathway by Mouse IgA Immune Complexes, The Journal of Experimental medicine.1982;155(1):231-47.
Raffaghello et al., Anti-GD2 monoclonal antibody immunotherapy: a promising strategy in the prevention of neuroblastoma relapse, 2003 Cancer Lett, vol. 197(1-2): p. 205-9.
Rajasekaran et al., 2015, Enhancement of antibody-dependent cell mediated cytotoxicity: a new era in cancer treatment, Immuno Targets and Therapy vol. 4: 91.
Roos et al., 2001, HumanIgA Activates the Complement System Via the Mannan-Binding Lectin Pathway J Immunol 167(5): 2861-2868.
Shields, et al. High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-6604.
Sorkin et al., Anti-GD2 with an FC point mutation reduces complement fixation and decreases antibody-induced allodynia, 2010, Pain 149(1): 135-142.
Suzuki and Cheung, Dialog anglioside GD2 as a therapeutic target for human diseases, 2015, Expert Opinion on Therapeutic Targets vol. 19: p. 349-62.
Terme et al., Chimeric Antibody c.8B6 to O-acetyl-GD2 Mediates the Same Efficient Anti-Neuroblastoma Effects as Therapeutic ch14.18 Antibody to GD2 Without Antibody Induced Allodynia, 2014, PLoS One 9(2): e87210.
Unituxin (dinutuximab) Highlights of Prescribing Information United Therapeutics Corp., Silver Spring, MD 20910, US License No. 1993, p. 19, Copyright 2015.
Yu et al. (2010), Anti-GD2 Antibody with GM-CSF, Interleukin-2,and Isotretinoin for Neuroblastoma N Engl J Med 363(14): 1324-1334.
Allesandri-Haber, Nicole et al., A Transient Receptor Potential Vanilloid-4-Dependent Mechanism of Hyperalgesia Is Engaged by Concerted Action of Inflammatory Mediators, The Journal of Neuroscience, Apr. 5, 2006, 26(14):3864-3784.
Brezski,Randall et al., Immunoglobulin isotype Knowledge and Application to FC Engineering,Current Opinions in Immunology, 2016, 40:62-69.

(56) References Cited

OTHER PUBLICATIONS

Eijkelkamp et al., GRK2: A Novel Cell-Specific Regulator of Severity andDuration of Inflammatory Pain, J. Neuroscience, Feb. 20, 2010, pp. 2138-2149.

Steurer, W. et al., Ex Vivo Coating of Islet Cell Allografts With Murine CTLA4/Fc Promotes Graft Tolerance, 1995. J Immunol. 155(3):1165-74.

Xiao, et al., 1997, Electrophysiological Characteristics of Primary Afferent Fibers After Systemic Administration of Anti-GC2 Ganglioside Antibody, Pain69: 145-151.

* cited by examiner

\>9754H|dinutuximab|Chimeric||H-GAMMA-1 (VH (1-113) [D1] CDR
EVQLLQSGPELEKPGASVMISCKASGSSFTGYNMNWVRQNIGKSLEWIGAIDPYYGGTSY 60
NQKFKGRATLTVDKSSSTAYMHLKSLTSEDSAVYYCVSGMEYWGQGTSVTVSS (SEQ ID NO: 3)

FIG. 1A

\>9754L|dinutuximab|Chimeric||L-KAPPA (V-KAPPA (1-113) [D1] CDR
EIVMTQSPATLSVSPGERATLSCRSSQSLVHRNGNTYLHWYLQKPGQSPKLLIHKVSNRF 60
SGVPDRFSGSGSGTDFTLKISRVEAEDLGVYFCSQSTHVPPLTFGAGTKLELK (SEQ ID NO: 4)

FIG. 1B

V-H ch14.18 DNA-sequence

GAAGTGCAGCTGCTGCAGAGCGGCCCGGAACTGGAAAAACCGGGCGCGAGCGTGATGATTAGCTGCAAAGC
GAGCGGCAGCAGCTTTACCGGCTATAACATGAACTGGGTGCGCCAGAACATTGGCAAAAGCCTGGAATGGAT
TGGCGCGATTGATCCGTATTATGGCGGCACCAGCTATAACCAGAAATTTAAAGGCCGCGCGACCCTGACCGTG
GATAAAAGCAGCAGCACCGCGTATATGCATCTGAAAAGCCTGACCAGCGAAGATAGCGCGGTGTATTATTGC
GTGAGCGGCATGGAATATTGGGGCCAGGGCACCAGCGTGACCGTGAGCAGC (SEQ ID NO: 7)

FIG. 1C

V-L ch14.18 DNA-sequence

GAAATTGTGATGACCCAGAGCCCGGCGACCCTGAGCGTGAGCCCGGGCGAACGCGCGACCCTGAGCTGCCGC
AGCAGCCAGAGCCTGGTGCATCGCAACGGCAACACCTATCTGCATTGGTATCTGCAGAAACCGGGCCAGAGCC
CGAAACTGCTGATTCATAAAGTGAGCAACCGCTTTAGCGGCGTGCCGGATCGCTTTAGCGGCAGCGGCAGCG
GCACCGATTTTACCCTGAAAATTAGCCGCGTGGAAGCGGAAGATCTGGGCGTGTATTTTTGCAGCCAGAGCAC
CCATGTGCCGCCGCTGACCTTTGGCGCGGGCACCAAACTGGAACTGAAA (SEQ ID NO: 8)

FIG. 1D

SEQ ID NO:1

Amino acid sequence of chimeric 3F8 heavy chain

Chimeric Heavy Chain - gamma1:

QVQLKESGPGLVAPSQSLSITCTVSGFSVTNYGVHWVRQPPGKGLEWLGVIWAGGITNYNSAFMSRLSIS
KDNSKSQVFLKMNSLQIDDTAMYYCASRGGHYGYALDYWGQGTSVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPSN
TKVDKRVEPKSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK

FIG. 1E

SEQ ID NO:2

Chimeric Light Chain - kappa:

SIVMTQTPKFLLVSAGDRVTITCKASQSVSNDVTWYQQKAGQSPKLLIYSASNRYSGVPDRFTGSGYGTA
FTFTISTVQAEDLAVYFCQQDYSSFGGGTKLEIKRTVAAPSVFIFPPSDEQLKSGTASVVCLLNNFYPRE
AKVQWKVDNALQSGNSQESVTEQDSKDSTYSLSSTLTLSKADYEKHKVYACEVTHQGLSSPVTKSFNRGE
C

FIG. 1F

|  |  | 120 | 140 | 160 |
|---|---|---|---|---|

```
                        120              140                160
(SEQ ID NO: 12) hIgA1   SSASPTSPKVFPLSLCSTQPDGNVV IACLVQGFFPQEPLSVTWSESGQGVTARNFPPSQD
(SEQ ID NO: 11) hIgA2m(1) SSASPTSPKVFPLSLDSTPQDGNVVVACLVQGFFPQEPLSVTWSESGQNVTARNFPPSQD
(SEQ ID NO: 13) hIgA20  SSASPTSPKVFPLSLDSTPQDGNVVVACLVQGFFPQEPLSVTWSESGQGVTARNFPPSQD

180        Cα1         200                220|   Hinge
   hIgA1      ASGDLYTTSSQLTLPATQCLAGKSVTCHVKHYTNPSQDVTVPCPVPSTPPTPSPSTPPTP
   hIgA2m(1)  ASGDLYTTSSQLTLPATQCPDGKSVTCHVKHYTNPSQDVTVPCPVPPPPP
   hIgA20     ASGDLYTTSSQLTLPATQCPDGKSVTCHVKHYTNPSQDVTVPCRVPPPPP 240|                260                280
   hIgA1      SPSCCHPRLSLHRPALEDLLLGSEANLTCTLTGLRDASGVTFTWTPSSGKSAVQGPPERD
   hIgA2m(1)     CCHPRLSLHRPALEDLLLGSEANLTCTLTGLRDASGATFTWTPSSGKSAVQGPPERD
   hIgA20        CCHPRLSLHRPALEDLLLGSEANLTCTLTGLRDASGATFTWTPSSGKSAVQGPPERD 300        Cα2         320                340|
   hIgA1      LCGCYSVSSVLPGCAEPWNHGKTFTCTAA YPESKTPLT ATLSKSGNTFRPEVHLLPPPSE
   hIgA2m(1)  LCGCYSVSSVLPGCAQPWNHGETFTCTAAHPESKTPLT ANITKSGNTFRPEVHLLPPPSE
   hIgA20     LCGCYSVSSVLPGSAQPWNHGETFTCTAAHPESKTPLT ATLSKSGNTFRPEVHLLPPPSE 360                380    Cα3         400
   hIgA1      ELALNELVTLT CLARGFSPKDVLVRWLQGSQELPREKYLTWASRQEPSQGTTTFAVTSIL
   hIgA2m(1)  ELALNELVTLT CLARGFSPKDVLVRWLQGSQELPREKYLTWASRQEPSQGTTTFAVTSIL
   hIgA20     ELALNELVTLT CLARGFSPKDVLVRWLQGSQELPREKYLTWASRQEPSQGTTTFAVTSIL 420                440        |   460   Tailpiece
   hIgA1      RVAAEDWKKGDTFSCMVGHEALPLAFTQKTIDRLAGKPTHVNVSVVMAEVDGTCY
   hIgA2m(1)  RVAAEDWKKGDTFSCMVGHEALPLAFTQKTIDRLAGKPTHVNVSVVMAEVDGTCY
   hIgA20     RVAAEDWKKGDTFSCMVGHEALPLAFTQKTIDRLAGKPTHVNVSVVMAEVDGT
```

FIG. 12A

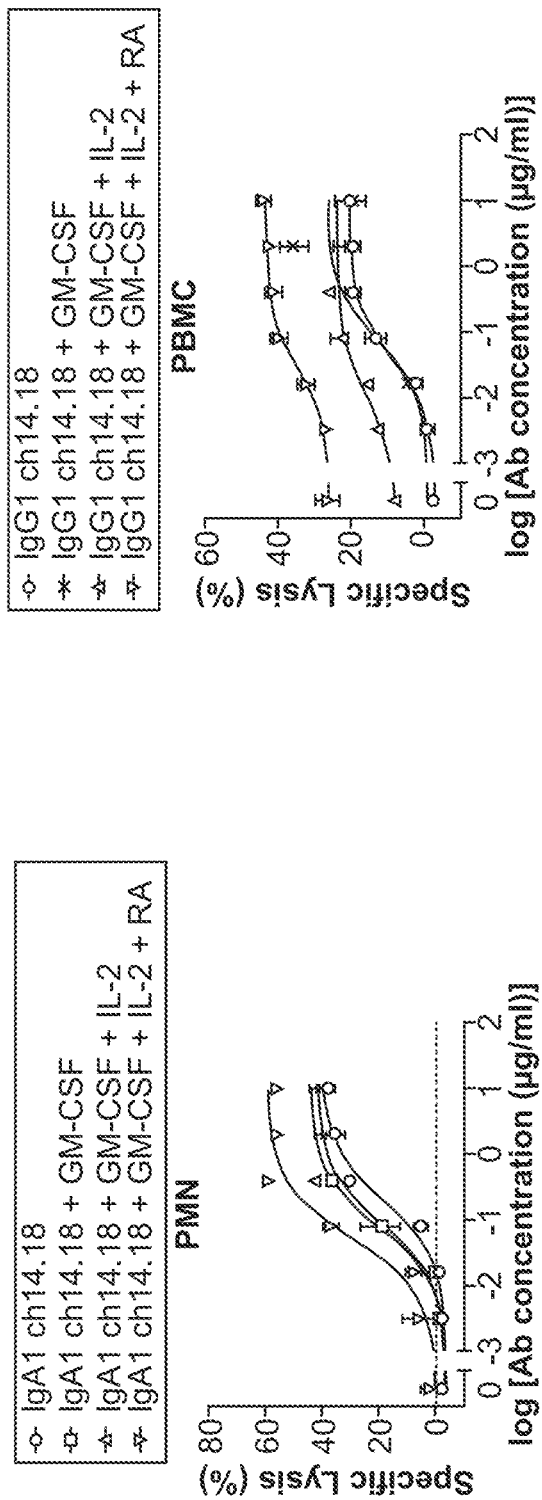
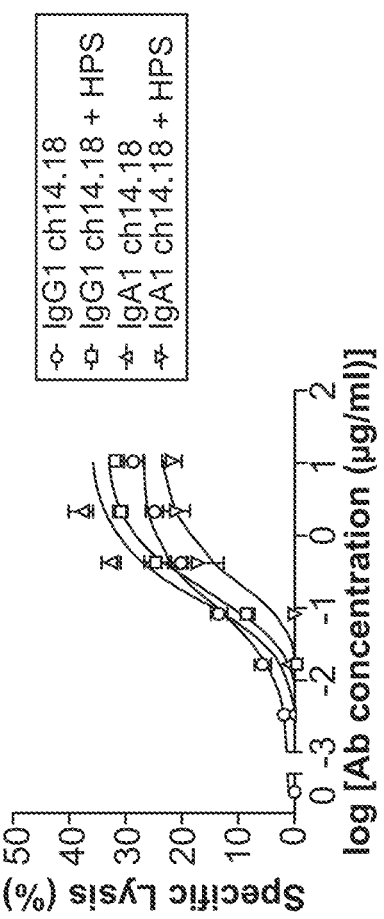
FIG. 15C
FIG. 15D

SEQUENCE LISTING

<160> NUMBER OF SEQ ID NOS: 25

<210> SEQ ID NO 1
<211> LENGTH: 449
<212> TYPE: PRT
<213> ORGANISM: Artificial Sequence
<220> FEATURE:
<223> OTHER INFORMATION: 3f8 heavy chain
<220> FEATURE:
<221> NAME/KEY: MISC_FEATURE
<223> OTHER INFORMATION: Description of Artificial Sequence: Synthetic polypeptide

<400> SEQUENCE: 1

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Ser Leu Gln Ile Asp Asp Thr Ala Met Tyr Tyr Cys Ala
                85                  90                  95

Ser Arg Gly Gly His Tyr Gly Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 211
<212> TYPE: PRT
<213> ORGANISM: Artificial Sequence
<220> FEATURE:
<223> OTHER INFORMATION: 3F8 light chain
<220> FEATURE:
<221> NAME/KEY: MISC_FEATURE
<223> OTHER INFORMATION: Description of Artificial Sequence: Synthetic
      polypeptide

<400> SEQUENCE: 2

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Thr Trp Tyr Gln Gln Lys Ala Gly Gln Ser Pro Lys Leu Leu Ile
            35                  40                  45

Tyr Ser Ala Ser Asn Arg Tyr Ser Gly Val Pro Asp Arg Phe Thr Gly
    50                  55                  60

Ser Gly Tyr Gly Thr Ala Phe Thr Phe Thr Ile Ser Thr Val Gln Ala
65                  70                  75                  80

Glu Asp Leu Ala Val Tyr Phe Cys Gln Gln Asp Tyr Ser Ser Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
            130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
    210

<210> SEQ ID NO 3
<211> LENGTH: 113
<212> TYPE: PRT
<213> ORGANISM: Artificial Sequence
<220> FEATURE:
<223> OTHER INFORMATION: anti-GD2 antibody ch14.18 heavy chain
<220> FEATURE:
<221> NAME/KEY: MISC_FEATURE
<223> OTHER INFORMATION: Description of Artificial Sequence: Synthetic
      polypeptide
```

<400> SEQUENCE: 3

Glu Val Gln Leu Leu Gln Ser Gly Pro Glu Leu Glu Lys Pro Gly Ala
1               5                   10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
50                  55                  60

Lys Gly Arg Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Ser Val Thr Val Ser
            100                 105                 110

Ser

<210> SEQ ID NO 4
<211> LENGTH: 113
<212> TYPE: PRT
<213> ORGANISM: Artificial Sequence
<220> FEATURE:
<223> OTHER INFORMATION: anti-GD2 antibody ch14.18 light chain
<220> FEATURE:
<221> NAME/KEY: MISC_FEATURE
<223> OTHER INFORMATION: Description of Artificial Sequence: Synthetic
      polypeptide

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys

<210> SEQ ID NO 5
<211> LENGTH: 6
<212> TYPE: PRT
<213> ORGANISM: Artificial Sequence
<220> FEATURE:
<223> OTHER INFORMATION: antibody C-terminus
<220> FEATURE:
<221> NAME/KEY: MISC_FEATURE
<223> OTHER INFORMATION: Description of Artificial Sequence: Synthetic
      peptide

<400> SEQUENCE: 5

Val Asp Gly Thr Cys Tyr
1               5

<210> SEQ ID NO 6
<211> LENGTH: 4
<212> TYPE: PRT
<213> ORGANISM: Artificial Sequence
<220> FEATURE:
<223> OTHER INFORMATION: mutated antibody C-terminus
<220> FEATURE:
<221> NAME/KEY: MISC_FEATURE
<223> OTHER INFORMATION: Description of Artificial Sequence: Synthetic
      peptide

<400> SEQUENCE: 6

Val Asp Gly Thr
1

<210> SEQ ID NO 7
<211> LENGTH: 339
<212> TYPE: DNA
<213> ORGANISM: Artificial Sequence
<220> FEATURE:
<223> OTHER INFORMATION: DNA sequence of antibody ch14.18 heavy chain
<220> FEATURE:
<221> NAME/KEY: misc_feature
<223> OTHER INFORMATION: Description of Artificial Sequence: Synthetic
      polynucleotide

<400> SEQUENCE: 7
gaagtgcagc tgctgcagag cggcccggaa ctggaaaaac cgggcgcgag cgtgatgatt      60
agctgcaaag cgagcggcag cagctttacc ggctataaca tgaactgggt gcgccagaac     120
attggcaaaa gcctggaatg gattggcgcg attgatccgt attatggcgg caccagctat     180
aaccagaaat ttaaaggccg cgcgaccctg accgtggata aaagcagcag caccgcgtat     240
atgcatctga aaagcctgac cagcgaagat agcgcggtgt attattgcgt gagcggcatg     300
gaatattggg ccagggcac cagcgtgacc gtgagcagc                             339

<210> SEQ ID NO 8
<211> LENGTH: 339
<212> TYPE: DNA
<213> ORGANISM: Artificial Sequence
<220> FEATURE:
<223> OTHER INFORMATION: DNA sequence of antibody ch14.18 light chain
<220> FEATURE:
<221> NAME/KEY: misc_feature
<223> OTHER INFORMATION: Description of Artificial Sequence: Synthetic
      polynucleotide

<400> SEQUENCE: 8
gaaattgtga tgacccagag cccggcgacc ctgagcgtga gcccgggcga acgcgcgacc      60
ctgagctgcc gcagcagcca gagcctggtg catcgcaacg gcaacaccta tctgcattgg     120
tatctgcaga accgggcca gagcccgaaa ctgctgattc ataaagtgag caaccgcttt     180
agcggcgtgc cggatcgctt tagcggcagc ggcagcggca ccgatttac cctgaaaatt     240 agccgcgtgg aagcggaaga tctgggcgtg tattttttgca gccagagcac ccatgtgccg     300
ccgctgacct ttggcgcggg caccaaactg gaactgaaa                            339

<210> SEQ ID NO 9
<211> LENGTH: 1017
<212> TYPE: DNA
<213> ORGANISM: Artificial Sequence
<220> FEATURE:
<223> OTHER INFORMATION: IgA2.0 heavy chain
<220> FEATURE:
<221> NAME/KEY: misc_feature
<220> FEATURE:
<223> OTHER INFORMATION: Description of Artificial Sequence: Synthetic polynucleotide
<220> FEATURE:
<221> NAME/KEY: CDS
<222> LOCATION: (1)..(1014)

<400> SEQUENCE: 9

```
gca tcc ccg acc agc ccc aag gtc ttc ccg ctg agc ctc gac agc acc     48
Ala Ser Pro Thr Ser Pro Lys Val Phe Pro Leu Ser Leu Asp Ser Thr
1               5                   10                  15 ccc caa gat ggg aac gtg gtc gtc gca tgc ctg gtc cag ggc ttc ttc     96
Pro Gln Asp Gly Asn Val Val Val Ala Cys Leu Val Gln Gly Phe Phe
            20                  25                  30 ccc cag gag cca ctc agt gtg acc tgg agc gaa agc gga cag ggc gtg    144
Pro Gln Glu Pro Leu Ser Val Thr Trp Ser Glu Ser Gly Gln Gly Val
        35                  40                  45 acc gcc aga aac ttc cca cct agc cag gat gcc tcc ggg gac ctg tac    192
Thr Ala Arg Asn Phe Pro Pro Ser Gln Asp Ala Ser Gly Asp Leu Tyr
    50                  55                  60 acg acg agc agc cag ctg acc ctg ccg gcc aca cag tgc cca gac ggc    240
Thr Thr Ser Ser Gln Leu Thr Leu Pro Ala Thr Gln Cys Pro Asp Gly
65                  70                  75                  80 aag tcc gtg aca tgc cac gtg aag cac tac acg aat ccc agc cag gat    288
Lys Ser Val Thr Cys His Val Lys His Tyr Thr Asn Pro Ser Gln Asp
                85                  90                  95 gtg act gtg ccc tgc cga gtt ccc cca cct ccc cca tgc tgc cac ccc    336
Val Thr Val Pro Cys Arg Val Pro Pro Pro Pro Pro Cys Cys His Pro
            100                 105                 110 cga ctg tcg ctg cac cga ccg gcc ctc gag gac ctg ctc tta ggt tca    384
Arg Leu Ser Leu His Arg Pro Ala Leu Glu Asp Leu Leu Leu Gly Ser
        115                 120                 125 gaa gcg aac ctc acg tgc aca ctg acc ggc ctg aga gat gcc tct ggt    432
Glu Ala Asn Leu Thr Cys Thr Leu Thr Gly Leu Arg Asp Ala Ser Gly
    130                 135                 140 gcc acc ttc acc tgg acg ccc tca agt ggg aag agc gct gtt caa gga    480
Ala Thr Phe Thr Trp Thr Pro Ser Ser Gly Lys Ser Ala Val Gln Gly
145                 150                 155                 160 cca cct gag cgt gac ctc tgt ggc tgc tac agc gtg tcc agt gtc ctg    528
Pro Pro Glu Arg Asp Leu Cys Gly Cys Tyr Ser Val Ser Ser Val Leu
                165                 170                 175 cct ggc tct gcc cag cca tgg aac cat ggg gag acc ttc acc tgc act    576
Pro Gly Ser Ala Gln Pro Trp Asn His Gly Glu Thr Phe Thr Cys Thr
            180                 185                 190 gct gcc cac ccc gag ttg aag acc cca cta acc gcc acc ctg tca aaa    624
Ala Ala His Pro Glu Leu Lys Thr Pro Leu Thr Ala Thr Leu Ser Lys
        195                 200                 205 tcc gga aac aca ttc cgg ccc gag gtc cac ctg ctg ccg ccg ccg tcg    672
Ser Gly Asn Thr Phe Arg Pro Glu Val His Leu Leu Pro Pro Pro Ser
    210                 215                 220 gag gag ctg gcc ctg aac gag ctg gtg acg ctg acg tgc ctg gca cgt    720
Glu Glu Leu Ala Leu Asn Glu Leu Val Thr Leu Thr Cys Leu Ala Arg
225                 230                 235                 240 ggc ttc agc ccc aag gat gtg ctg gtt cgc tgg ctg cag ggg tca cag    768
Gly Phe Ser Pro Lys Asp Val Leu Val Arg Trp Leu Gln Gly Ser Gln
                245                 250                 255 gag ctg ccc cgc gag aag tac ctg act tgg gca tcc cgg cag gag ccc    816
Glu Leu Pro Arg Glu Lys Tyr Leu Thr Trp Ala Ser Arg Gln Glu Pro
            260                 265                 270 agc cag ggc acc acc acc ttc gct gtg acc agc ata ctg cgc gtg gca    864
Ser Gln Gly Thr Thr Thr Phe Ala Val Thr Ser Ile Leu Arg Val Ala
        275                 280                 285
```

```
gcc gag gac tgg aag aag ggg gac acc ttc tcc tgc atg gtg ggc cac      912
Ala Glu Asp Trp Lys Lys Gly Asp Thr Phe Ser Cys Met Val Gly His
    290             295                 300 gag gcc ctg ccg ctg gcc ttc aca cag aag acc atc gac cgc ttg gcg      960
Glu Ala Leu Pro Leu Ala Phe Thr Gln Lys Thr Ile Asp Arg Leu Ala
305             310                 315                 320 ggt aaa ccc acc cat gtc aat gtg tct gtt gtc atg gcg gag gtg gac     1008
Gly Lys Pro Thr His Val Asn Val Ser Val Val Met Ala Glu Val Asp
                325                 330                 335 ggc acc tga                                                          1017
Gly Thr
```

<210> SEQ ID NO 10
<211> LENGTH: 338
<212> TYPE: PRT
<213> ORGANISM: Artificial Sequence
<220> FEATURE:
<223> OTHER INFORMATION: Synthetic Construct

<400> SEQUENCE: 10

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Ser Ala Gln Pro Trp Asn His Gly Glu Thr Phe Thr Cys Thr
            180                 185                 190

Ala Ala His Pro Glu Leu Lys Thr Pro Leu Thr Ala Thr Leu Ser Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285
```

```
Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Met Ala Glu Val Asp
                325                 330                 335

Gly Thr

<210> SEQ ID NO 11
<211> LENGTH: 342
<212> TYPE: PRT
<213> ORGANISM: Artificial Sequence
<220> FEATURE:
<223> OTHER INFORMATION: hIgA2m(1)
<220> FEATURE:
<221> NAME/KEY: MISC_FEATURE
<223> OTHER INFORMATION: Description of Artificial Sequence: Synthetic
      polypeptide

<400> SEQUENCE: 11

Ser Ser Ala Ser Pro Thr Ser Pro Lys Val Phe Pro Leu Ser Leu Asp
1               5                   10                  15

Ser Thr Pro Gln Asp Gly Asn Val Val Ala Cys Leu Val Gln Gly
            20                  25                  30

Phe Phe Pro Gln Glu Pro Leu Ser Val Thr Trp Ser Glu Ser Gly Gln
        35                  40                  45

Asn Val Thr Ala Arg Asn Phe Pro Pro Ser Gln Asp Ala Ser Gly Asp
50                  55                  60

Leu Tyr Thr Thr Ser Ser Gln Leu Thr Leu Pro Ala Thr Gln Cys Pro
65                  70                  75                  80

Asp Gly Lys Ser Val Thr Cys His Val Lys His Tyr Thr Asn Pro Ser
                85                  90                  95

Gln Asp Val Thr Val Pro Cys Pro Val Pro Pro Pro Pro Cys Cys
            100                 105                 110

His Pro Arg Leu Ser Leu His Arg Pro Ala Leu Glu Asp Leu Leu Leu
        115                 120                 125

Gly Ser Glu Ala Asn Leu Thr Cys Thr Leu Thr Gly Leu Arg Asp Ala
130                 135                 140

Ser Gly Ala Thr Phe Thr Trp Thr Pro Ser Ser Gly Lys Ser Ala Val
145                 150                 155                 160

Gln Gly Pro Pro Glu Arg Asp Leu Cys Gly Cys Tyr Ser Val Ser Ser
                165                 170                 175

Val Leu Pro Gly Cys Ala Gln Pro Trp Asn His Gly Glu Thr Phe Thr
            180                 185                 190

Cys Thr Ala Ala His Pro Glu Leu Lys Thr Pro Leu Thr Ala Asn Ile
        195                 200                 205

Thr Lys Ser Gly Asn Thr Phe Arg Pro Glu Val His Leu Leu Pro Pro
210                 215                 220

Pro Ser Glu Glu Leu Ala Leu Asn Glu Leu Val Thr Leu Thr Cys Leu
225                 230                 235                 240

Ala Arg Gly Phe Ser Pro Lys Asp Val Leu Val Arg Trp Leu Gln Gly
                245                 250                 255

Ser Gln Glu Leu Pro Arg Glu Lys Tyr Leu Thr Trp Ala Ser Arg Gln
            260                 265                 270

Glu Pro Ser Gln Gly Thr Thr Thr Phe Ala Val Thr Ser Ile Leu Arg
        275                 280                 285
```

Val Ala Ala Glu Asp Trp Lys Lys Gly Asp Thr Phe Ser Cys Met Val
            290                 295                 300

Gly His Glu Ala Leu Pro Leu Ala Phe Thr Gln Lys Thr Ile Asp Arg
305                 310                 315                 320

Leu Ala Gly Lys Pro Thr His Val Asn Val Ser Val Val Met Ala Glu
                325                 330                 335

Val Asp Gly Thr Cys Tyr
            340

<210> SEQ ID NO 12
<211> LENGTH: 355
<212> TYPE: PRT
<213> ORGANISM: Artificial Sequence
<220> FEATURE:
<223> OTHER INFORMATION: hIgA1
<220> FEATURE:
<221> NAME/KEY: MISC_FEATURE
<223> OTHER INFORMATION: Description of Artificial Sequence: Synthetic
      polypeptide

<400> SEQUENCE: 12

Ser Ser Ala Ser Pro Thr Ser Pro Lys Val Phe Pro Leu Ser Leu Cys
1               5                   10                  15

Ser Thr Gln Pro Asp Gly Asn Val Val Ile Ala Cys Leu Val Gln Gly
                20                  25                  30

Phe Phe Pro Gln Glu Pro Leu Ser Val Thr Trp Ser Glu Ser Gly Gln
            35                  40                  45

Gly Val Thr Ala Arg Asn Phe Pro Pro Ser Gln Asp Ala Ser Gly Asp
        50                  55                  60

Leu Tyr Thr Thr Ser Ser Gln Leu Thr Leu Pro Ala Thr Gln Cys Leu
65                  70                  75                  80

Ala Gly Lys Ser Val Thr Cys His Val Lys His Tyr Thr Asn Pro Ser
                85                  90                  95

Gln Asp Val Thr Val Pro Cys Pro Val Pro Ser Thr Pro Pro Thr Pro
            100                 105                 110

Ser Pro Ser Thr Pro Pro Thr Pro Ser Pro Ser Cys Cys His Pro Arg
        115                 120                 125

Leu Ser Leu His Arg Pro Ala Leu Glu Asp Leu Leu Leu Gly Ser Glu
130                 135                 140

Ala Asn Leu Thr Cys Thr Leu Thr Gly Leu Arg Asp Ala Ser Gly Val
145                 150                 155                 160

Thr Phe Thr Trp Thr Pro Ser Ser Gly Lys Ser Ala Val Gln Gly Pro
                165                 170                 175

Pro Glu Arg Asp Leu Cys Gly Cys Tyr Ser Val Ser Ser Val Leu Pro
            180                 185                 190

Gly Cys Ala Glu Pro Trp Asn His Gly Lys Thr Phe Thr Cys Thr Ala
        195                 200                 205

Ala Tyr Pro Glu Ser Lys Thr Pro Leu Thr Ala Thr Leu Ser Lys Ser
    210                 215                 220

Gly Asn Thr Phe Arg Pro Glu Val His Leu Leu Pro Pro Pro Ser Glu
225                 230                 235                 240

Glu Leu Ala Leu Asn Glu Leu Val Thr Leu Thr Cys Leu Ala Arg Gly
                245                 250                 255

Phe Ser Pro Lys Asp Val Leu Val Arg Trp Leu Gln Gly Ser Gln Glu
            260                 265                 270

Leu Pro Arg Glu Lys Tyr Leu Thr Trp Ala Ser Arg Gln Glu Pro Ser

```
                275                 280                 285
Gln Gly Thr Thr Thr Phe Ala Val Thr Ser Ile Leu Arg Val Ala Ala
    290                 295                 300

Glu Asp Trp Lys Lys Gly Asp Thr Phe Ser Cys Met Val Gly His Glu
305                 310                 315                 320

Ala Leu Pro Leu Ala Phe Thr Gln Lys Thr Ile Asp Arg Leu Ala Gly
                325                 330                 335

Lys Pro Thr His Val Asn Val Ser Val Val Met Ala Glu Val Asp Gly
                340                 345                 350

Thr Cys Tyr
        355

<210> SEQ ID NO 13
<211> LENGTH: 340
<212> TYPE: PRT
<213> ORGANISM: Artificial Sequence
<220> FEATURE:
<223> OTHER INFORMATION: higA2.0
<220> FEATURE:
<221> NAME/KEY: MISC_FEATURE
<223> OTHER INFORMATION: Description of Artificial Sequence: Synthetic
      polypeptide

<400> SEQUENCE: 13

Ser Ser Ala Ser Pro Thr Ser Pro Lys Val Phe Pro Leu Ser Leu Asp
1               5                   10                  15

Ser Thr Pro Gln Asp Gly Asn Val Val Ala Cys Leu Val Gln Gly
                20                  25                  30

Phe Phe Pro Gln Glu Pro Leu Ser Val Thr Trp Ser Glu Ser Gly Gln
                35                  40                  45

Gly Val Thr Ala Arg Asn Phe Pro Pro Ser Gln Asp Ala Ser Gly Asp
    50                  55                  60

Leu Tyr Thr Thr Ser Ser Gln Leu Thr Leu Pro Ala Thr Gln Cys Pro
65                  70                  75                  80

Asp Gly Lys Ser Val Thr Cys His Val Lys His Tyr Thr Asn Pro Ser
                85                  90                  95

Gln Asp Val Thr Val Pro Cys Arg Val Pro Pro Pro Pro Cys Cys
                100                 105                 110

His Pro Arg Leu Ser Leu His Arg Pro Ala Leu Glu Asp Leu Leu Leu
                115                 120                 125

Gly Ser Glu Ala Asn Leu Thr Cys Thr Leu Thr Gly Leu Arg Asp Ala
    130                 135                 140

Ser Gly Ala Thr Phe Thr Trp Thr Pro Ser Ser Gly Lys Ser Ala Val
145                 150                 155                 160

Gln Gly Pro Pro Glu Arg Asp Leu Cys Gly Cys Tyr Ser Val Ser Ser
                165                 170                 175

Val Leu Pro Gly Ser Ala Gln Pro Trp Asn His Gly Glu Thr Phe Thr
                180                 185                 190

Cys Thr Ala Ala His Pro Glu Leu Lys Thr Pro Leu Thr Ala Thr Leu
                195                 200                 205

Ser Lys Ser Gly Asn Thr Phe Arg Pro Glu Val His Leu Leu Pro Pro
    210                 215                 220

Pro Ser Glu Glu Leu Ala Leu Asn Glu Leu Val Thr Leu Thr Cys Leu
225                 230                 235                 240

Ala Arg Gly Phe Ser Pro Lys Asp Val Leu Val Arg Trp Leu Gln Gly
                245                 250                 255
```

```
Ser Gln Glu Leu Pro Arg Glu Lys Tyr Leu Thr Trp Ala Ser Arg Gln
            260                 265                 270

Glu Pro Ser Gln Gly Thr Thr Thr Phe Ala Val Thr Ser Ile Leu Arg
        275                 280                 285

Val Ala Ala Glu Asp Trp Lys Lys Gly Asp Thr Phe Ser Cys Met Val
    290                 295                 300

Gly His Glu Ala Leu Pro Leu Ala Phe Thr Gln Lys Thr Ile Asp Arg
305                 310                 315                 320

Leu Ala Gly Lys Pro Thr His Val Asn Val Ser Val Val Met Ala Glu
                325                 330                 335

Val Asp Gly Thr
            340

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Ser Ser Phe Thr Gly Tyr Asn
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ile Asp Pro Tyr Tyr Gly Gly Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Val Ser Gly Met Glu Tyr
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ser Leu Val His Arg Asn Gly Asn Thr Tyr
1               5                   10

<210> SEQ ID NO 18

<400> SEQUENCE: 18
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ser Thr His Val Pro Pro Leu Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Tyr Gly Val His
1               5

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Ile Trp Ala Gly Gly Ile Thr Asn Tyr Asn Ser Ala Phe Met
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Gly Gly His Tyr Gly Tyr Ala Leu Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Ala Ser Gln Ser Val Ser Asn Asp Val Thr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic

```
    polypeptide

<400> SEQUENCE: 24

Ser Ala Ser Asn Arg Tyr Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Gln Asp Tyr Ser Ser Phe
1               5
```

ANTI-GD2 ANTIBODY

CROSS REFERENCE

This application is a Continuation Application of International Patent Application PCT/NL2018/050629, filed Sep. 21, 2018, which claims priority to EP 17192476.4, filed Sep. 21, 2017, each of which is entirely incorporated herein by reference in its entirety.

SEQUENCE LISTING

The instant application contains a Sequence Listing which has been filed electronically in ASCII format and is hereby incorporated by reference in its entirety. Said ASCII copy, created on Feb. 14, 2023, is named 199828-703301_SL.txt and is 31,020 bytes in size.

TECHNICAL FIELD

The invention relates to the field of antibodies. In particular it relates to antibodies that bind the ganglioside GD2. It further relates to the use of GD2 antibodies in medical and detection methods. The invention further relates to cells, nucleic acid molecules and methods for the production of the antibodies.

BACKGROUND

Approximately 12% of all pediatric cancer patients succumb to neuroblastoma, the most common extracranial solid tumor of childhood. The majority of patients is diagnosed with high-risk neuroblastoma with a mortality of 50%. Neuroblastoma therapy consists of intensive multimodality treatment with severe toxicities. High-risk neuroblastoma therapy consists of intensive multimodality treatment with severe short- and long-term toxicities. Recurrence rates are high with limited further treatment options. Residual disease is treated with intensive chemotherapy, radiotherapy, high-dose chemotherapy followed by autologous hematopoietic stem cell rescue and isotretinoin. Complete eradication of the tumor is often not achieved (Matthay et al., 1999; New Engl. J. of Med Vol 341: pp 1165-73). Intensification of conventional therapy has not improved outcome and is even associated with increased toxicity.

In 2015 the antibody dinutuximab (trade name Unituxin), directed against ganglioside GD2, a carbohydrate antigen uniformly expressed on neuroblastoma and neural tissue, was FDA-approved for neuroblastoma treatment. Application of this antibody, combined with cytokines and differentiation factors, has improved patient prognosis and demonstrated that neuroblastoma is susceptible to immunotherapy (Yu et al., 2010; New Engl. J. Med, Vol 363: pp 1324-34; and Suzuki and Cheung., 2015; Expert Opin Ther Targets Vol 19: p. 349-62). Dinutuximab significantly improved event-free survival in comparison to standard treatment.

Dinutuximab is a chimeric monoclonal antibody composed of the variable heavy- and light-chain regions of the murine anti-GD2 antibody 14.18 and the constant regions of human IgG1 heavy-chain and kappa light-chain (Gillies et al., 1989; J Immunol Methods, 125: p. 191-202). It is directed against the end-terminal penta-oligosaccharide of GD2, an extracellularly expressed disialoganglioside on tissues of the central nervous system and peripheral nerves, as well as on many tumors of neuroectodermal origin, including neuroblastoma (Suzuki and Cheung, 2015; Expert Opin Ther Targets Vol 19: p. 349-62). Antibody produced in SP2/0 mouse myeloma cells can result in aberrant glycosylation with respect to natural human antibodies. In Europe the antibody is now produced in CHO cells. The uniform expression of GD2 on neuroblastoma together with the low expression on other tissues makes this tumor associated antigen a promising target for antibody therapy. Dinutuximab is used in combination with isotretinoin and alternating administration of IL-2 and GM-CSF for the first-line treatment against high-risk neuroblastoma in patients where a response after induction therapy was shown (Suzuki and Cheung, 2015; Expert Opin Ther Targets Vol 19: p. 349-62).

Preclinical research has shown that dinutuximab mediates its anti-tumor effects through antibody dependent cell mediated cytotoxicity (ADCC) and complement mediated cytotoxicity (CDC) (Barker et al., 1991; Cancer Res, Vol 51: p. 144-9). For ADCC activity, most therapeutic antibodies depend on NK cells and possibly macrophages for their action. Remarkably, the ADCC activity of dinutuximab against neuroblastoma is for some reason also dependent on granulocyte activation. This is shown in vitro and in vivo, by showing that patient outcome depends in part on granulocyte activation (Barker et al., 1991; Cancer Res, Vol 51: p. 144-9; Cheung et al., 2012; J Clin Oncol, Vol 30: p. 426-32; and Batova et al., 1999; Clin Cancer Res Vol 5: p. 4259-63). These observations have formed the basis for the inclusion of GM-CSF or G-CSF in the current therapeutic regimen to further stimulate granulocytes to enhance the anti-tumor response against neuroblastoma (Cheung et al., 2012; J Clin Oncol, Vol 30: p. 426-32; and Batova et al., 1999; Clin Cancer Res Vol 5: p. 4259-63).

In spite of the good clinical effects of dinutuximab it is associated with a number of toxicities. The most common toxicities include tachycardia, hypertension, hypotension, difficult to treat pain, fever and urticaria. Many of these toxicities are dose-dependent and are rarely noted at low dosages. Other toxicities include hyponatremia, hypokalemia, nausea, vomiting and diarrhea (Mora J, 2016, Expert review of clinical pharmacology, pp 1-7; http://dx.doi.org/10.1586/17512433.2016.1160775).

The anti-GD2 antibodies and the methods of treatment of present invention exhibit improved efficacy. In addition, toxicity associated with dinutuximab treatment is reduced, in particular pain associated toxicity is abrogated, as shown in pre-clinical models.

SUMMARY OF THE INVENTION

The invention provides an anti-ganglioside GD2 antibody that comprises an antibody variable domain and antibody constant domains, wherein the variable domain comprises a heavy and light chain variable region comprising respectively at least the CDR3 of the heavy chain variable region of antibody ch14.18 and at least the CDR3 of the light chain variable region of antibody ch14.18; and an IgA hinge and $C_H2$ domain. The variable domain preferably comprises a heavy and light chain variable region comprising respectively at least the CDR1, CDR2 and CDR3 of the heavy chain variable region of antibody ch14.18 and at least the CDR1, CDR2 and CDR3 of the light chain variable region of antibody ch14.18. In a preferred embodiment the variable domain comprises the heavy and light chain variable region of antibody ch14.18.

The invention further provides a method of treatment of a subject that has a GD2 positive tumor or is at risk of having a GD2 positive tumor the method comprising administering a therapeutic amount of an antibody of the invention to the subject in need thereof. The method preferably further comprises administering retinoic acid in an amount effective to upregulate the ganglioside GD2 in said GD2 positive tumor, preferably neuroblastoma in said subject. The method may further comprise administering granulocyte-macrophage colony-stimulating factor (GM-CSF, granulocyte colony-stimulating factor (G-CSF) or a combination thereof to said subject. GM-CSF, G-CSF or a combination thereof can increase the number of granulocytes in the subject but is also administered to improve the induced cell killing.

The invention further provides an antibody of the invention for use in the treatment of a subject that has a GD2 positive tumor or is at risk of having a GD2 positive tumor. The invention further provides an antibody of the invention in combination with retinoic acid for use in the treatment of a subject that has a GD2 positive tumor or is at risk of having a GD2 positive tumor. The invention further provides an antibody of the invention in combination with GM-CSF, G-CSF or a combination thereof for use in the treatment of a subject that has a GD2 positive tumor or is at risk of having a GD2 positive tumor. The invention further provides an antibody of the invention in combination with GM-CSF, G-CSF or a combination thereof and retinoic acid for use in the treatment of a subject that has a GD2 positive tumor or is at risk of having a GD2 positive tumor.

The GD2 positive tumor is preferably a GD2 positive neuroblastoma such as a neuroectoderm-derived tumor or a sarcoma. In a preferred embodiment the GD2 positive tumor is a GD2 positive neuroblastoma, retinoblastoma, melanoma, small cell lung cancer, brain tumor such as glioblastoma, osteosarcoma, rhabdomyosarcoma, Ewing's sarcoma in children and adolescents, or liposarcoma, fibrosarcoma, leiomyosarcoma or another soft tissue sarcoma in adults. In a preferred embodiment the GD2 positive tumor is a neuroblastoma. The neuroblastoma treated with a method or use of the invention is preferably a high risk neuroblastoma.

In a preferred embodiment an antibody of the invention comprises a heavy chain variable region with the amino acid sequence

```
EVQLLQSGPE LEKPGASVMI SCKASGSSFT GYNMNWVRQN

IGKSLEWIGA IDPYYGGTSY NQKFKGRATL TVDKSSSTAY

MHLKSLTSED SAVYYCVSGM EYWGQGTSVT VSS;
``` and a light chain variable region with the amino acid sequence

```
EIVMTQSPAT LSVSPGERAT LSCRSSQSLV HRNGNTYLHW

YLQKPGQSPK LLIHKVSNRF SGVPDRFSGS GSGTDFTLKI

SRVEAEDLGV YFCSQSTHVP PLTFGAGTKL ELK;
``` a heavy chain comprising an IgA hinge and $C_H2$ domain.

Provided herein is an engineered antibody or fragment thereof for use in improvement of patient compliance and/or a reduction of a side effect associated with immunoglobulin G (IgG) antibody therapy, wherein the engineered antibody or fragment thereof comprises: (a) CDR1, CDR2, and CDR3 of an immunoglobulin G (IgG); and (b) the constant regions or portion thereof of an immunoglobulin A (IgA), wherein the engineered antibody or fragment thereof results in reduction of at least one side effect upon administration to the subject as compared to administration of a comparable amount of a corresponding IgG antibody.

In an aspect, the engineered antibody or fragment thereof further comprises a heavy chain and light chain variable region of IgG. In an aspect, the constant regions or portion thereof of the IgA comprises a hinge, a $C_H2$ constant region, or a combination thereof. In an aspect, the constant regions or portion thereof comprises a hinge and a $C_H2$ constant region of the IgA. In an aspect, the constant regions comprise a constant heavy and constant light chain of the IgA. In an aspect, the constant regions or portion thereof of the IgA comprises a hinge and a constant heavy chain domain. In an aspect, the antibody or fragment thereof is chimerized, humanized, human, or non-human. In an aspect, the constant regions or portion thereof is human.

In an aspect, the side effect comprises an innate immune response. In some cases, the innate immune response comprises a complement response. In some cases, the complement response comprises IgG binding to FcγRs or C1q. In certain embodiments, the side effect comprises one or more of pain, visceral hypersensitivity, allodynia, hyperalgesia, allergic reactions and flu-like symptoms. In some cases, the pain is acute pain, migraine or intense visceral pain.

In some cases, determining the reduction of the side effect is measured by performing flow cytometry, an in vitro assay, or a combination thereof. In some cases, the flow cytometry comprises determining cellular lysis, binding, cell death, receptor expression, or a combination thereof. In some cases, the flow cytometry comprises determining live/dead staining of a cell. In some cases, the in vitro assay comprises ELISA, antibody-dependent cell-mediated cytotoxicity (ADCC), complement-dependent cytotoxicity (CDC), hemolytic assay, or a combination thereof.

In some cases, the engineered antibody or fragment thereof when administered results in an increased antibody-dependent cell-mediated cytotoxicity (ADCC) and/or reduced complement-dependent cytotoxicity (CDC) as compared to the corresponding IgG antibody that comprises the same CDR1, CDR2, and CDR3. In an aspect, the reduction comprises from 5%, 10%, 15%, 20%, 25%, 30%, 35%, 40%, 45%, 50%, 55%, 60%, 65%, 70%, 75%, 80%, 85%, 90%, 95%, to 100% of the side effect as compared to administering a comparable IgG antibody that comprises the same CDR1, CDR2, and CDR3.

In some cases, the antibody or fragment thereof binds a target present on a non-cancerous cell, a cancer cell, or a combination thereof. In some cases, the antibody or fragment thereof binds a target from a brain-metastasizing cancer. In some cases, the antibody or fragment thereof binds one or more of GD2, ALK, hNET, GD3, and CD20. In some cases, the GD2 positive tumor is neuroblastoma, retinoblastoma, melanoma, small cell lung cancer, glioblastoma, osteosarcoma, rhabdomyosarcoma, Ewing's sarcoma, liposarcoma, fibrosarcoma, leiomyosarcoma, and any combinations thereof. In an aspect, the antibody or fragment thereof binds a neuroblastoma cell. In some cases, the ALK (anaplastic lymphoma kinase) positive tumor is an anaplastic large-cell lymphoma, an adenocarcinoma of the lung, a neuroblastoma, an inflammatory myofibroblastic tumor, a renal cell carcinomas, esophageal squamous cell carcinoma, breast cancer, a colonic adenocarcinoma, a glioblastoma multiforme or an anaplastic thyroid cancer. In some cases, the hNET (human norepinephrine transporter) positive tumor is a bladder tumor, breast tumor, prostate tumor, carcinoma, leukemia, liver cancer, lung cancer, lymphoma, Hodgkin's lymphoma, Non-Hodgkin's lymphoma, melanoma, neuroblastoma, ovarian tumor, pancreatic tumor or a retinoblastoma. In some case, the GD3 positive tumor is a neuroectodermal tumor of the center nervous system, glioma, neuroblastoma, retinoblastoma, ependymoma, sarcoma, melanoma, breast cancer, ovarian cancer, glioblastoma, Ewing's sarcoma, or small cell lung carcinoma. In some cases the CD20 positive tumor is a leukemia, a lymphoma or a neuroblastoma.

Provided herein is a pharmaceutical composition comprising an engineered antibody or fragment thereof and a pharmaceutically acceptable carrier.

Provided herein is a kit comprising an engineered antibody or fragment thereof and instructions for use thereof.

Provided herein is a method comprising: administering to a subject a pharmaceutical composition comprising an antibody or fragment thereof comprising: (a) CDR1, CDR2, and CDR3 of an immunoglobulin G (IgG); and (b) the constant regions or portion thereof of an immunoglobulin A (IgA), wherein the administering results in a reduction of a side effect in the subject as compared to administering a comparable IgG antibody that comprises the same CDR1, CDR2, and CDR3.

Provided herein is an engineered immunoglobulin G (IgG) antibody fragment, wherein the engineered IgG antibody fragment comprises at least a hinge domain and a $C_H2$ domain of a human IgA antibody. In some cases, the engineered IgG antibody fragment, when administered to a subject, results in increased antibody-dependent cell-mediated cytotoxicity (ADCC) and/or reduced complement-dependent cytotoxicity (CDC) as compared to a comparable antibody fragment absent the hinge domain and a $C_H2$ domain of a human IgA antibody Provided herein is a method of treating pain or allodynia associated with IgG administration comprising administering to a subject an engineered IgG antibody or fragment thereof comprising the constant regions of an IgA antibody. Provided herein is a method of reducing complement activation resulting from IgG administration comprising administering to a subject an engineered IgG antibody or fragment thereof comprising the constant regions of an IgA antibody.

DETAILED DESCRIPTION OF THE INVENTION

Gangliosides are sialic acid-containing glycosphingolipids that play important roles in signal transduction as well as cell adhesion and recognition. The ganglioside GD2 is a b-series ganglioside that requires the enzymes GD3 synthase and GD2 synthase to add sialic acid units onto its precursor $G_{M2}$. Normal tissues generally express a-series gangliosides, whereas b-series gangliosides are expressed during fetal development and are restricted primarily to the nervous system in healthy adults and at low levels in peripheral nerves and skin melanocytes. A structure of the ganglioside GD2 is depicted in FIG. 10.

The ganglioside GD2 is highly expressed on neuroectoderm-derived tumors and sarcomas, including neuroblastoma, retinoblastoma, melanoma, small cell lung cancer, brain tumors, osteosarcoma, rhabdomyosarcoma, Ewing's sarcoma in children and adolescents, as well as liposarcoma, fibrosarcoma, leiomyosarcoma and other soft tissue sarcomas in adults. GD2 expression in normal individuals appears to be limited to the brain and certain peripheral nerves and melanocytes. As the brain is typically not accessible for normal circulating antibodies GD2 is considered an attractive target for tumor-specific therapy (For review see Mahiuddin et al., 2014; FEBS letters 588: 288-297). Mahiuddin et al describe various GD2 targeted approaches among which there are the GD2 specific antibodies. A number of targeted therapies has reached the clinic and show promise in phase I, II and III trials.

Various GD2 antibodies are presently under development. The antibodies are thought to induce ADCC and CDC, for which in particular neuroblastoma appears to be relatively sensitive. Various avenues are being pursued to improve the efficacy and reduce the toxicity of the targeted approaches. The most frequently used antibodies all originate from murine IgG3 antibodies. The murine antibodies have been humanized in recent years. A number of variants have been made. Murine antibody 14.18 has been chimerized to ch14.18 and humanized into hu14.18 both have a human IgG1 background (Mahiuddin et al., 2014; FEBS letters 588: 288-297). The murine IgG3 antibody 3F8 has been used in humans. To reduce human anti-mouse responses and improve the efficacy of the antibody while reducing toxicity 3F8 was chimerized (ch3F8) and humanized 3F8 (hu3F8-IgG1 and hu3F8-IgG4). In GD2 binding studies by SPR, ch3F8 and hu3F8 maintained KD comparable to m3F8. Unlike other anti-GD2 antibodies, m3F8, ch3F8 and hu3F8 had substantially slower koff. Similar to m3F8, both ch3F8 and hu3F8 inhibited tumor cell growth in vitro, while cross-reactivity with other gangliosides was comparable to that of m3F8. Both peripheral blood mononuclear cell (PBMC)-ADCC and polymorphonuclear leukocytes (PMN)-ADCC of ch3F8 and hu3F8-IgG1 were more potent than m3F8. Hu3F8-IgG4 had near absent PBMC-ADCC and CDC. Hu3F8 and m3F8 had similar tumor-to-non tumor ratios in biodistribution studies. Anti-tumor effect against neuroblastoma xenografts was better with hu3F8-IgG1 than m3F8 (see Cheung et al., 2012; Oncoimmunology 1.4: 477-486).

An antibody (Ab), also known as an immunoglobulin (Ig), is a large protein. An antibody interacts with various components of the immune system. Some of the interactions are mediated by its Fc region (located at the base), which contains site(s) involved in these interactions.

Antibodies are proteins belonging to the immunoglobulin superfamily. They typically have two heavy chains and two light chains. There are several different types of antibody heavy chains that define the five different types of crystallizable fragments (Fc) that may be attached to the antigen-binding fragments. The five different types of Fc regions allow antibodies to be grouped into five isotypes. An Fc region of a particular antibody isotype is able to bind to its specific Fc receptor (FcR) thus allowing the antigen-antibody complex to mediate different roles depending on which FcR it binds. The ability of an IgG antibody to bind to its corresponding FcR is modulated by the presence/absence of interaction sites and the structure of the glycan(s) (if any) present at sites within its Fe region. The ability of antibodies to bind to FcRs helps to direct the appropriate immune response for each different type of foreign object they encounter.

Though the general structure of all antibodies is similar, a region at the tip of the protein is extremely variable, allowing millions of antibodies with slightly different tip structures, or antigen-binding sites, to exist. This region is known as the hypervariable region. The enormous diversity of antigen binding by antibodies is largely defined by the hypervariable region and the variable domain containing the hypervariable region.

An antibody of the invention is typically a full-length antibody. The term 'full length antibody' is defined as comprising an essentially complete immunoglobulin molecule, which however does not necessarily have all functions of an intact immunoglobulin. For the avoidance of doubt, a full length antibody has two heavy and two light chains. Each chain contains constant (C) and variable (V) regions. A heavy chain of a full length antibody typically comprises a $C_H1$, a $C_H2$, a $C_H13$, a VH region and a hinge region. A light chain of a full length antibody typically comprises a CL region and a VL region.

An antibody binds to antigen via the variable region domains contained in the Fab portion. An antibody variable domain comprises a heavy chain variable region and a light chain variable region. Full length antibodies according to the invention encompass heavy and light chains wherein mutations may be present that provide desired characteristics. Full length antibodies should not have deletions of substantial portions of any of the regions. However, IgG molecules wherein one or several amino acid residues are substituted, inserted, deleted or a combination thereof, without essentially altering the antigen binding characteristics of the resulting antibody, are embraced within the term "full length" antibody. For instance, a 'full length" antibody can have a substitution, insertion, deletion or a combination thereof, of between 1 and 10 (inclusive) amino acid residues, preferably in non-CDR regions, wherein the deleted amino acids are not essential for the binding specificity of the antibody.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions. Binding of IgG to the FcγRs or C1q depends on residues located in the hinge region and the $C_H2$ domain. Two regions of the $C_H2$ domain are critical for FcγRs and C1q binding, and have unique sequences in IgG2 and IgG4. Substitutions into human IgG1 of IgG2 residues at positions 233-236 were shown to greatly reduce ADCC and CDC. Furthermore, Idusogie et al. demonstrated that alanine substitution at different positions, including K322A, significantly reduced complement activation. Similarly, mutations in the CH2 domain of murine IgG2A were shown to reduce the binding to FcγRI, and C1q. Numerous mutations have been made in the $C_H2$ domain of human IgG1 and their effect on ADCC and CDC tested in vitro. Notably, alanine substitution at position 333 was reported to increase both ADCC and CDC. Fc-receptor functions are among others reviewed in Bruhns et al., 2009. Blood. 113(16):3716-25; Armour et al., 1999. Eur J Immunol. 29(8):2613-24; Shields et al., 2001. J Biol Chem. 276(9):6591-604; Idusogie et al., 2000. J Immunol. 164(8):4178-84; Steurer et al., 1995. J Immunol. 155(3): 1165-74; and Idusogie. et al., 2001. J Immunol. 166(4): 2571-5. IgG1 antibodies have a C1q binding site through which complement activation through the classical pathway is achieved. IgA antibodies can also activate complement. This can be through the alternative pathway, the complement lectin pathway and the classical pathway (Jarvis et al., J Immunol. 1989; 143(5):1703-9; Hiemstra et al., European journal of immunology. 1987; 17(3):321-6; Pfaffenbach et al., The Journal of experimental medicine. 1982; 155(1): 231-47; Roos et al., J Immunol. 2001; 167(5):2861-8; Pascal et al., Haematologica DOI: 10.3324/haematol.2011.061408; and Lohse et al., Britisch Journal of Haematology. 2011doi: 10.1111/bjh.14624).

The present inventors found that ADCC activity of a murine, murine chimerized or humanized IgG or human IgM GD2 antibody with unmodified constant regions can be increased by replacing at least the hinge domain and the $C_H2$ domain thereof by a hinge domain and $C_H2$ domain of a human IgA antibody, preferably a human IgA1 antibody. In a preferred embodiment also the $C_H3$ domain is of a human IgA antibody. In a preferred embodiment the antibody comprises an essentially complete IgA constant region. The invention therefore provides an antibody that can bind GD2 and that comprises ADCC activity and that comprises a hinge domain and $C_H2$ domain of a human IgA antibody. A GD2 antibody of the invention has a reduced capacity to induce CDC. A GD2 antibody of the invention has a reduced capacity to induce pain when compared to the murine, murine chimerized or humanized IgG or human IgM original GD2 antibody.

An IgA constant domain or hinge region may have one or more amino acid insertions, deletions, substitutions, additions or a combination thereof at one or more positions with respect to a germ line IgA domain or hinge region. An IgA domain or hinge region preferably has at most 4 amino acid insertions, deletions, substitutions, additions or a combination thereof, preferably at most 3; 2 or preferably at most 1 amino acid insertions, deletions, substitutions, additions or a combination thereof. Such a protein is still an IgA constant domain or hinge region. An IgA constant domain or hinge region may have one or more amino acid insertions, deletions, substitutions, additions or a combination thereof at one or more positions with respect to a germ line IgA. The IgA constant part (including the three domains and the hinge region) can have 0; 1; 2; 3; 4; 5; 6; 7; 8; 9; 10; 11; 12; 13; 14; or 15 amino acid insertions, deletions, substitutions, additions or a combination thereof.

In one embodiment the invention provides an anti-ganglioside GD2 antibody that comprises an antibody variable domain and antibody constant domains, wherein the variable domain comprises a heavy and light chain variable region comprising respectively at least the CDR3 of the heavy and light chain variable regions of antibody ch14.18 and an IgA hinge and $C_H2$ domain. The variable domain preferably comprises a heavy and light chain variable region comprising respectively at least the CDR1, CDR2 and CDR3 of the heavy and light chain variable regions of antibody ch14.18 as depicted in FIG. 1. The variable domain preferably comprises a heavy and light chain variable region of antibody ch14.18 as depicted in FIG. 1.

The anti-ganglioside GD2 antibody heavy chain variable region is preferably a heavy chain variable region of antibody ch14.18 with 0-5 amino acid insertions, deletions, substitutions, additions or a combination thereof at one or more positions with respect to the heavy chain variable region sequence of antibody ch14.18 indicated in FIG. 1. The one or more positions are preferably not positions in the CDR1, CDR2 and CDR3 regions. The sequence of the CDRs is thus as indicated for heavy chain variable region of antibody ch14.18 of FIG. 1. It is preferred that the heavy chain variable region has 0-4 amino acid insertions, deletions, substitutions, additions or a combination thereof at one or more positions with respect to the heavy chain variable region sequence of antibody ch14.18 indicated in FIG. 1, wherein the one or more positions are not positions in the CDR1, CDR2 and CDR3 regions. It is preferred that the heavy chain variable region has 0-3, more preferably 0-2, more preferably 0-1 amino acid insertions, deletions, substitutions, additions or a combination thereof at one or more positions with respect to the heavy chain variable region sequence of antibody ch14.18 indicated in FIG. 1, wherein the one or more positions are not positions in the CDR1, CDR2 and CDR3 regions. In a preferred embodiment a heavy chain variable region in the antibody of the invention has 0 amino acid insertions, deletions, substitutions, additions or a combination thereof with respect to the heavy chain variable region sequence of antibody ch14.18 in FIG. 1.

The anti-ganglioside GD2 antibody light chain variable region is preferably a light chain variable region of antibody ch14.18 with 0-5 amino acid insertions, deletions, substitutions, additions or a combination thereof at one or more positions with respect to the light chain variable region sequence of antibody ch14.18 indicated in FIG. 1. The one or more positions are preferably not positions in the CDR1, CDR2 and CDR3 regions. The sequence of the CDRs is thus as indicated for light chain variable region of antibody ch14.18 of FIG. 1. It is preferred that the light chain variable region has 0-4 amino acid insertions, deletions, substitutions, additions or a combination thereof at one or more positions with respect to the light chain variable region sequence of antibody ch14.18 indicated in FIG. 1, wherein the one or more positions are not positions in the CDR1, CDR2 and CDR3 regions. It is preferred that the light chain variable region has 0-3, more preferably 0-2, more preferably 0-1 amino acid insertions, deletions, substitutions, additions or a combination thereof at one or more positions with respect to the light chain variable region sequence of antibody ch14.18 indicated in FIG. 1, wherein the one or more positions are not positions in the CDR1, CDR2 and CDR3 regions. In a preferred embodiment a light chain variable region in the antibody of the invention has 0 amino acid insertions, deletions, substitutions, additions or a combination thereof with respect to the light chain variable region sequence of antibody ch14.18 in FIG. 1.

In another embodiment the invention provides an anti-ganglioside GD2 antibody that comprises an antibody variable domain and antibody constant domains, wherein the variable domain comprises a heavy and light chain variable region comprising respectively at least the CDR3 of the heavy and light chain variable regions of antibody 3F8 and an IgA hinge and $C_H2$ domain. The variable domain preferably comprises a heavy and light chain variable region comprising respectively at least the CDR1, CDR2 and CDR3 of the heavy and light chain variable regions of antibody 3F8 (as depicted in FIG. 1). The variable domain preferably comprises a heavy and light chain variable region of antibody 3F8 as depicted in FIG. 1. The anti-ganglioside GD2 antibody heavy chain variable region is preferably a heavy chain variable region of antibody 3F8 with 0-5 amino acid insertions, deletions, substitutions, additions or a combination thereof at one or more positions with respect to the heavy chain variable region sequence of antibody 3F8 indicated in FIG. 1. The one or more positions are preferably not positions in the CDR1, CDR2 and CDR3 regions. The sequence of the CDRs is thus as indicated for heavy chain variable region of antibody 3F8 of FIG. 1. It is preferred that the heavy chain variable region has 0-4 amino acid insertions, deletions, substitutions, additions or a combination thereof at one or more positions with respect to the heavy chain variable region sequence of antibody 3F8 indicated in FIG. 1, wherein the one or more positions are not positions in the CDR1, CDR2 and CDR3 regions. It is preferred that the heavy chain variable region has 0-3, more preferably 0-2, more preferably 0-1 amino acid insertions, deletions, substitutions, additions or a combination thereof at one or more positions with respect to the heavy chain variable region sequence of antibody 3F8 indicated in FIG. 1, wherein the one or more positions are not positions in the CDR1, CDR2 and CDR3 regions. In a preferred embodiment a heavy chain variable region in the antibody of the invention has 0 amino acid insertions, deletions, substitutions, additions or a combination thereof with respect to the heavy chain variable region sequence of antibody 3F8 in FIG. 1.

The anti-ganglioside GD2 antibody light chain variable region is preferably a light chain variable region of antibody 3F8 with 0-5 amino acid insertions, deletions, substitutions, additions or a combination thereof at one or more positions with respect to the light chain variable region sequence of antibody 3F8 indicated in FIG. 1. The one or more positions are preferably not positions in the CDR1, CDR2 and CDR3 regions. The sequence of the CDRs is thus as indicated for light chain variable region of antibody 3F8 of FIG. 1. It is preferred that the light chain variable region has 0-4 amino acid insertions, deletions, substitutions, additions or a combination thereof at one or more positions with respect to the light chain variable region sequence of antibody 3F8 indicated in FIG. 1, wherein the one or more positions are not positions in the CDR1, CDR2 and CDR3 regions. It is preferred that the light chain variable region has 0-3, more preferably 0-2, more preferably 0-1 amino acid insertions, deletions, substitutions, additions or a combination thereof at one or more positions with respect to the light chain variable region sequence of antibody 3F8 indicated in FIG. 1, wherein the one or more positions are not positions in the CDR1, CDR2 and CDR3 regions. In a preferred embodiment a light chain variable region in the antibody of the invention has 0 amino acid insertions, deletions, substitutions, additions or a combination thereof with respect to the light chain variable region sequence of antibody 3F8 in FIG. 1.

IgA has two subclasses (IgA1 and IgA2) and can be produced as a monomeric as well as a dimeric form. The antibody in the present invention is preferably a monomeric antibody. The IgA elements in an antibody of the invention are preferably human IgA elements. An IgA element can be an IgA1 element or an IgA2 element. IgA elements in an antibody of the invention can be all IgA1 elements or all IgA2 elements or a combination of IgA1 and IgA2 elements. An IgA element is preferably a human IgA element. Preferably all IgA element in the antibody are human IgA elements. The IgA elements can be IgA1 elements, preferably human IgA1 elements. The IgA elements can also be IgA2, preferably IgA2m(1) elements, preferably human IgA1 elements. The $C_H1$ domain and/or $C_H3$ domain of the antibody can be an IgG $C_H1$ domain, an IgG $C_H3$ domain or a combination thereof. It is preferred that the $C_H1$ domain, $C_H3$ domain or combination thereof is an IgA $C_H1$ domain, an IgA $C_H3$ domain or a combination thereof. It is preferred that the IgA $C_H1$ domain and/or hinge region is a human IgA $C_H1$ domain and/or human IgA hinge region. Said human IgA $C_H1$ domain and/or human IgA hinge region is preferably an human IgA1 $C_H1$ domain or human IgA1 hinge region. Said human IgA $C_H1$ domain and/or human IgA hinge region is preferably an human IgA2m(1) $C_H1$ domain or human IgA2m(1) hinge region. The constant domains and hinge region of the antibody are preferably human constant regions and hinge region, preferably of a human IgA antibody. The constant domains and hinge region of the antibody are preferably human IgA1 or human IgA2m(1) constant domains and hinge region.

A human constant region can have 0-15 amino acid changes with respect to a human allele as found in nature. An amino acid change may be introduced for various reasons. Non-limiting examples include but are not limited to improving production or homogeneity of the antibody, adapting half-life in the circulation, stability of the HC/LC combination, optimizing glycosylation, adjusting dimerization or complex formation, adjusting ADCC activity. A human constant region can have 0; 1; 2; 3; 4; 5; 6; 7; 8; 9; 10; 11; 12; 13; 14; and 15 amino acid changes with respect to a human allele as found in nature. The changed amino acid is preferably one chosen from an amino acid at a corresponding position of a different isotype.

In one embodiment the constant regions of the heavy chain are IgA2 constant regions, preferably human IgA2 constant regions, preferably human IgA2m(1). In one aspect the human constant region is a mutated IgA2m(1) sequence.

In one embodiment the antibody comprises the constant regions of an IgA2m(1) sequence, preferably with at least one and preferably at least 2; 3; 4; 5; and preferably at least 7 of the following mutations: N166G; P221R; N337T; I338L; T339S; C331S; and mutation of the C-terminal amino acid sequence which is a human IgA2m(1) antibody is "...VDGTCY" (SEQ ID NO: 5) into "...VDGT" (SEQ ID NO: 6). FIG. 12 shows the sequence of human IgA1; IgA2m(1) and a preferred mutated IgA2m(1) sequence (hIgA2.0); see also FIG. 12A.

In one embodiment the GD2 antibody comprises a heavy chain with the constant regions of FIG. 12A with 0; 1; 2; 3; 4; 5; 6; 7; 8; 9; 10; 11; 12; 13; 14; and amino acid changes with respect to the sequence provided in FIG. 12A, provided that amino acids at positions 166; 221; 337; 338; 339; and 331 are 166G; 221R; 337T; 338L; 339S and 331S. Preferably the C-terminal amino acid sequence which is a human IgA2m(1) antibody is "...VDGTCY" (SEQ ID NO: 5) is "...VDGT" (SEQ ID NO: 6).

A human IgA sequence of whatever subtype relates to the heavy chain of the antibody. The heavy chain is subject to isotype switching.

The mention IgA antibody preferably comprises a ch14.18 variable domain or a 3F8 variable domain, preferably a ch14.18 variable domain.

An anti-ganglioside GD2 antibody comprising:
a heavy chain variable region of antibody ch14.18 with 0-5 amino acid insertions, deletions, substitutions, additions or a combination thereof at one or more positions with respect to the heavy chain variable region sequence of antibody ch14.18 indicated in FIG. 1. The one or more positions are preferably not positions in the CDR1, CDR2 and CDR3 regions. The sequence of the CDRs is thus as indicated for heavy chain variable region of antibody ch14.18 of FIG. 1. It is preferred that the heavy chain variable region has 0-4 amino acid insertions, deletions, substitutions, additions or a combination thereof at one or more positions with respect to the heavy chain variable region sequence of antibody ch14.18 indicated in FIG. 1, wherein the one or more positions are not positions in the CDR1, CDR2 and CDR3 regions. It is preferred that the heavy chain variable region has 0-3, more preferably 0-2, more preferably 0-1 amino acid insertions, deletions, substitutions, additions or a combination thereof at one or more positions with respect to the heavy chain variable region sequence of antibody ch14.18 indicated in FIG. 1, wherein the one or more positions are not positions in the CDR1, CDR2 and CDR3 regions. In a preferred embodiment a heavy chain variable region in the antibody of the invention has 0 amino acid insertions, deletions, substitutions, additions or a combination thereof with respect to the heavy chain variable region sequence of antibody ch14.18 in FIG. 1;
a light chain variable region of antibody ch14.18 with 0-5 amino acid insertions, deletions, substitutions, additions or a combination thereof at one or more positions with respect to the light chain variable region sequence of antibody ch14.18 indicated in FIG. 1. The one or more positions are preferably not positions in the CDR1, CDR2 and CDR3 regions. The sequence of the CDRs is thus as indicated for light chain variable region of antibody ch14.18 of FIG. 1. It is preferred that the light chain variable region has 0-4 amino acid insertions, deletions, substitutions, additions or a combination thereof at one or more positions with respect to the light chain variable region sequence of antibody ch14.18 indicated in FIG. 1, wherein the one or more positions are not positions in the CDR1, CDR2 and CDR3 regions. It is preferred that the light chain variable region has 0-3, more preferably 0-2, more preferably 0-1 amino acid insertions, deletions, substitutions, additions or a combination thereof at one or more positions with respect to the light chain variable region sequence of antibody ch14.18 indicated in FIG. 1, wherein the one or more positions are not positions in the CDR1, CDR2 and CDR3 regions. In a preferred embodiment a light chain variable region in the antibody of the invention has 0 amino acid insertions, deletions, substitutions, additions or a combination thereof with respect to the light chain variable region sequence of antibody ch14.18 in FIG. 1;
an IgA heavy chain, preferably comprising an amino acid sequence as depicted in FIG. 13E with 0; 1; 2; 3; 4; 5; 6; 7; 8; 9; 10; 11; 12; 13; 14; and 15 amino acid changes with respect to the sequence provided in FIG. 13E, provided that amino acids at positions 166; 221; 337; 338; 339; and 331 are 166G; 221R; 337T; 338L; 339S and 331S. Preferably the C-terminal amino acid sequence which is a human IgA2m(1) antibody is "...VDGTCY" (SEQ ID NO: 5) is "...VDGT" (SEQ ID NO: 6); and
a light chain constant domain, preferably of antibody ch14.18.

The anti-ganglioside GD2 antibody of the invention preferably exhibits more antibody-dependent cell-mediated cytotoxicity (ADCC) than the antibody dinutuximab when measured in a suitable in vitro ADCC assay. It preferably exhibits less complement-dependent cytotoxicity (CDC) than the antibody dinutuximab when measured in a suitable in vitro CDC assay. Various ADCC and CDC assays are available to the person skilled in the art. In the context of the present invention it is preferred that an ADCC assay or a CDC assay as described in the examples is used. ADCC function of an antibody as claimed is preferably measured in a classical chromium release assay (as described for instance in examples). CDC function of an antibody as claimed is preferably measured in a method based on 7-AAD positivity in flow cytometry (see for instance the examples). The antibody preferably exhibits 20% or less, more preferably 10% or less of the complement-dependent cytotoxicity (CDC) of the antibody dinutuximab when measured in a suitable in vitro CDC assay. In a preferred embodiment the antibody comprises an albumin-binding domain (ABD) attached to a heavy or light chain of the antibody. Reference is made to Meyer, et al., 2016; MAbs. Vol. 8. No. 1; for details on the linkage of the albumin-binding domain to a heavy or light chain. In another embodiment another domain is added to increase the half-life of the antibody. In a preferred embodiment the domain the DIII domain of human albumin. Such a domain is preferably physically linked to a constant region of an IgA part of the antibody.

In an aspect, an engineered antibody or fragment thereof, as provided herein comprising the variable region of an IgG antibody and the constant regions of an IgA antibody, can reduce a side effect. In an aspect, an engineered antibody or fragment thereof, as provided herein, can reduce a side effect associated with an IgG antibody therapy. In an aspect, an engineered antibody or fragment thereof, as provided herein, can reduce a side effect associated with an innate immune response. Side effects associated with such innate immune response can be inflammation, complement system activation, white blood cell (mast cell, phagocyte, macrophage, neutrophil, dendritic cell, basophil, eosinophil, natural killer cell, and gamma delta cell activity. In some cases, an engineered antibody or fragment thereof, as provided herein, can reduce a side effect associated with complement system activation.

Complement system activation can be a biochemical cascade of the immune system that complements the ability of antibodies or fragments thereof to clear pathogens or mark them for destruction. The complement cascade comprises a variety of plasma proteins, which are synthesized in the liver, these proteins have various functions comprising: triggering the recruitment of inflammatory cells, tagging pathogens for destruction (opsonization), perforating the plasma membrane of pathogens, eliminating neutralized antigen-antibody complexes, and any combination thereof. In some aspects, a reduction of a side effect can comprise the reduction of complement system activation.

In an aspect, an IgG antibody or portion thereof can react with a target resulting in binding of C1q to the Fc portion of antigen-bound IgG after which C1r and C1s attach to form C1, an enzyme associated with complement activation. C1 can proceed to enzymatically cleave C4 into C4a and C4b. C4b binds to adjacent proteins and carbohydrates on the surface of the target and then binds C2. Activated C1 can cleave C2 into C2a and C2b forming C4b2a, a C3 convertase. C3 convertase can cleave C3 into C3a and C3b. In further steps of the complement activation pathway, C3b can bind to C4b2a, a C3 convertase, to form C4b2a3b, a C5 convertase that can cleave C5 into C5a and C5b. C5b can bind to the target and also bind C6, C7, c8, and C9 to form C5b6789n, the membrane attack complex (MAC). MAC can destroy gram-negative bacteria as well as cells displaying foreign antigens (such as virus-infected cells, tumor cells, to name a few) by causing their lysis. In an aspect, a reduction in a complement response can be measured by the absence or reduced level of any one of: C1q, C1r, C1s, C1, C4, C4a, C4b, C2, C2a, C2b, C4b2a, C3, C3a, C3b, C4b2a3b, C5, C5a, C5b, C6, C7, C8, C9, C5b6789m, MAC, and any combination thereof. In an aspect, a reduction in a complement response can refer to a reduction of about 5%, 10%, 15%, 20%, 25%, 30%, 35%, 40%, 45%, 50%, 55%, 60%, 65%, 70%, 75%, 80%, 85%, 90%, 95%, 99%, 100% of binding of a complement factor selected from any one of: C1q, C1r, C1s, C1, C4, C4a, C4b, C2, C2a, C2b, C4b2a, C3, C3a, C3b, C4b2a3b, C5, C5a, C5b, C6, C7, C8, C9, C5b6789m, and MAC to the engineered antibody that comprises an IgG variable region and the IgA constant regions or portion thereof as described herein, as compared to a comparable amount of an IgG antibody.

A reduction of a complement response can be determined by performing an ELISA, flow cytometry, hematology, or an in vitro assay to quantify an amount of a complement factor selected from any one of: (C1q, C1r, C1s, C1, C4, (4a, (4b, C2, (C2a, C2b, C4b2a, C3, C3a, C3b, C4b2a3b, C5, C5a, C5b, C6, C7, C8, C9. C5b6789m, MAC, and any combination thereof. In some aspects, an antibody or fragment thereof provided herein can result in a lower level of a complement factor as compared to a comparable antibody or fragment thereof comprising the provided CDR1, CDR2, and CDR3 regions. In some aspects, an engineered IgG-IgA antibody or fragment thereof provided herein can result in a lower level of a complement factor as compared to a comparable IgG antibody or fragment thereof comprising the same CDR1, CDR2, and CDR3. A reduction of a complement response can also be measured by flow cytometric quantification of complement dependent lysis of target cells as well as described in the examples.

Additional side effects which can be mitigated or reduced by administration of an engineered antibody or fragment thereof described herein, as compared to administration of an IgG, can refer to any side effects associated with IgG antibody therapy. Side effects associated with IgG antibody therapy can include inflammation, thromboembolic events, haemolytic events, complement-system associated events, and a combination thereof. In some cases, an Ig; antibody therapy can result in side effects such as: inflammation, hypertension, hypotension, pain, fever, urticaria, allergy, chill, weakness, diarrhea, nausea, vomit, rash, itch, cough, constipation, edema, headache, fever, shortness of breath, muscle ache, pain, decreased appetite, insomnia, dizziness, anaphylaxis, thrombosis, heart failure, bleeding, hepatitis, enterocolitis, mucositis, cytokine syndrome, hypothyroidism, hyponatremia, hyponotremia, capillary leak syndrome, and allodynia.

In an aspect, reducing a complement response, complement-associated side-effect, or a toxicity can improve treatment compliance of a subject in need thereof.

In some cases, an antibody or fragment thereof provided herein, such as engineered antibodies, can be administered at a higher dose, a longer treatment period, or with more frequency as compared to a comparable IgG antibody comprising the same CDR1, CDR2, and CDR3 regions. In some cases, an antibody or fragment thereof provided herein, such as engineered antibodies, can be administered at a higher dose from about 1×, 2×, 3×, 4×, 5×, 6×, 7×, 8×, 9×, 10×, over that of a comparable IgG antibody comprising the same CDR1, CDR2, and CDR3 regions. In some cases, an antibody or fragment thereof provided herein, such as engineered antibodies, can be administered for a longer time period from about 1 hour, 5 hrs, 10 hrs, 1 day, 2 days, 3 days, 4 days, 5 days, 7 days, 14 days, 24 days, 30 days, monthly, bimonthly, bi-yearly, yearly, and daily over that of a comparable IgG antibody comprising the same CDR1, CDR2, and CDR3 regions. In some cases, an antibody or fragment thereof provided herein, such as engineered antibodies, can be administered more frequency such as hourly, daily, weekly, monthly, yearly as compared to a comparable IgG antibody comprising the same CDR1, CDR2, and CDR3 regions.

A reason for changing an amino acid at a certain position can be immunogenicity. Other reasons include but are not limited to improving production or homogeneity of the antibody. Antibodies of the present invention have variable heavy and variable light chain regions derived from a murine background.

Antibodies with such variable domains can be used in humans. Presently it is preferred to de-immunize such variable domains. De-immunization typically involves the modification of the murine sequence into a more human sequence whenever possible. Typically such modifications are directed towards removing one or more T-cell epitopes or one more B-cell epitopes from the variable domain. In a preferred embodiment one or more (human) T-cell epitopes have been removed by replacement of at least one amino acid of the epitope with a different amino acid. Often it is sufficient to substitute the so-called "anchor" amino acid. Suitable replacement amino acids can be obtained from somatic cell hypermutants of the particular VH or VL. Replacement with an amino acid that is naturally present at that position in a human antibody is preferred. Also human B-cell epitopes can be removed by replacement of at least one amino acid of the epitope with a different amino acid. Often it, is sufficient to substitute only one amino acid of the epitope. Suitable replacement amino acids can be obtained from somatic cell hypermutants of the particular VH or VL. Replacement, with an amino acid that is naturally present at that position in a human antibody is preferred. Preferably a variable domain of the invention is modified with respect to one or more exterior residues. Such residues are readily encountered by the immune system and are preferably selectively replaced with human residues to provide a hybrid molecule that comprises either a weakly immunogenic or substantially non-immunogenic surface. Suitable replacement amino acids can be obtained from somatic cell hypermutants of the particular VH or VL. Replacement with an amino acid that is naturally present at that position in a human antibody is preferred. The invention thus further provides an antibody of the invention that comprises a humanized heavy chain variable region, a humanized light chain variable region or a combination thereof. A light chain of an antibody as defined herein has a light chain constant region. The light, chain constant, region is preferably the light chain constant region of the corresponding antibody. A light, chain comprising a ch14.18 light chain variable region preferably also comprises the light chain constant region of the ch14.18 antibody. A light chain comprising a 3F8 light chain variable region preferably also comprises the light chain constant region of the 3F8 antibody.

The invention further provides a method of treatment of a subject that has a GD2 positive tumor or is at risk of having said GD2 positive tumor the method comprising administering a therapeutic amount of an antibody of the invention to the subject in need thereof. Also provided is an antibody of the invention for use in the treatment of a subject that has a GD2 positive tumor or is at risk of having a GD2 positive tumor. The treatment preferably further comprises administering retinoic acid in an amount effective to upregulate the ganglioside GD2 in neuroblastoma cells in said subject. The treatment preferably further comprises administering granulocyte-macrophage colony-stimulating factor (GM-CSF). G-CSF or a combination thereof in an amount effective to increase the number of granulocytes in the subject and/or to increase ADCC. The GM-CSF, G-CSF or a combination thereof is preferably of a species that is to be treated. It is preferably human GM-CSF, human G-CSF or a combination thereof.

The GD2 positive tumor is preferably a GD2 positive neuroblastoma such as a neuroectoderm-derived tumor or a sarcoma. In a preferred embodiment the GD2 positive tumor is a GD2 positive neuroblastoma, retinoblastoma, melanoma, small cell lung cancer, brain tumor, osteosarcoma, rhabdomyosarcoma. Ewing’s sarcoma in children and adolescents, or liposarcoma, fibrosarcoma, leiomyosarcoma or another soft tissue sarcoma in adults. In a preferred embodiment the GD2 positive tumor is a neuroblastoma. The neuroblastoma treated with a method or use of the invention is preferably a high risk neuroblastoma.

The retinoic acid is preferably 13-cis-retinoic acid (isotretinoin).

The invention further provides an antibody of the invention or a method or antibody for use of the invention, wherein the antibody comprises a heavy chain variable region with the amino acid sequence

```
EVQLLQSGPE LEKPGASVMI SCKASGSSFT GYNMNWVRQN
IGKSLEWIGA IDPYYGGTSY NQKFKGRATL TVDKSSSTAY
MHLKSLTSED SAVYYCVSGM EYWGQGTSVT VSS
``` and a light chain variable region with the amino acid sequence

```
EIVMTQSPAT LSVSPGERAT LSCRSSQSLV HRNGNTYLHW
YLQKPGQSPK LLIHKVSNRF SGVPDRFSGS GSGTDFTLKI
SRVEAEDLGV YFCSQSTHVP PLTFGAGTKL ELK.
```

The invention also provides a nucleic acid molecule or combination of nucleic acid molecules that codes for a heavy chain, a light or preferably both of an antibody as described herein. The nucleic acid molecule or combination preferably further comprises one or more sequences for the expression of an antibody as described. Non-limiting examples of such expression sequences are a promoter, a termination sequence, an enhancer, an intron etc. Such sequences are not necessarily present on the nucleic acid molecule as such sequences can be provided in cis by the integration site of the nucleic acid molecule in, for instance, a chromosome of a cell, or a vector comprising said nucleic acid molecule. Suitable integration sites in a cellular chromosome can easily be determined and targeted, for instance by means of homologous recombination.

Further provided is a cell that comprises a nucleic acid molecule or combination as described herein.

Further provided are means and methods for the production of an antibody as described herein using a nucleic acid molecule or combination of the invention or a cell comprising a nucleic acid molecule or combination of nucleic acid molecules of the invention.

A nucleic acid molecule or combination according to the invention is for instance comprised in a cell. When said nucleic acid is expressed in said cell the translated product of the nucleic acid molecule can be, or be incorporated into, an antibody of the invention. The invention thus also provides a cell comprising a nucleic acid molecule or combination according to the invention. The invention further provides a cell comprising a nucleic acid molecule or combination of the invention and that is capable of producing an antibody of the invention. Further provided is a method for producing an antibody of the invention comprising culturing a cell comprising expressing one or more nucleic acid molecules that code for an antibody of the invention and harvesting the antibody from the culture medium, the cell or a combination thereof. Said cell is preferably an animal cell, more preferably a mammalian cell. The cell is preferably a cell that is normally used for the production of an antibody for use in humans. Non-limiting examples of such cells are CHO, NSO, HEK cells preferably HEK293F cells, and PER.C6 cells. Cells may specifically designed to suit certain purposes, for instance, most cell lines used for the production of antibodies have been adapted for growth in suspension, in high densities and other properties. For the purpose of the invention a suitable cell is any cell capable of comprising and preferably of producing an antibody according to the invention.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 1: Variable heavy and light chain amino acid of the antibodies ch14.18 (panel A (SEQ ID NO: 3) and B (SEQ ID NO: 4) respectively; the CDR regions are underlined). DNA sequences coding for the variable heavy and light chain of the antibody ch14.18 (panel C (SEQ ID NO: 7) and D (SEQ ID NO: 8) respectively). For 3F8 a chimeric gammal heavy chain (SEQ ID NO: 1) and a chimeric kappa light chain (SEQ ID NO: 2) are depicted. The respective CDRs are underlined.

EXAMPLES

Example 1

Figure 2A:
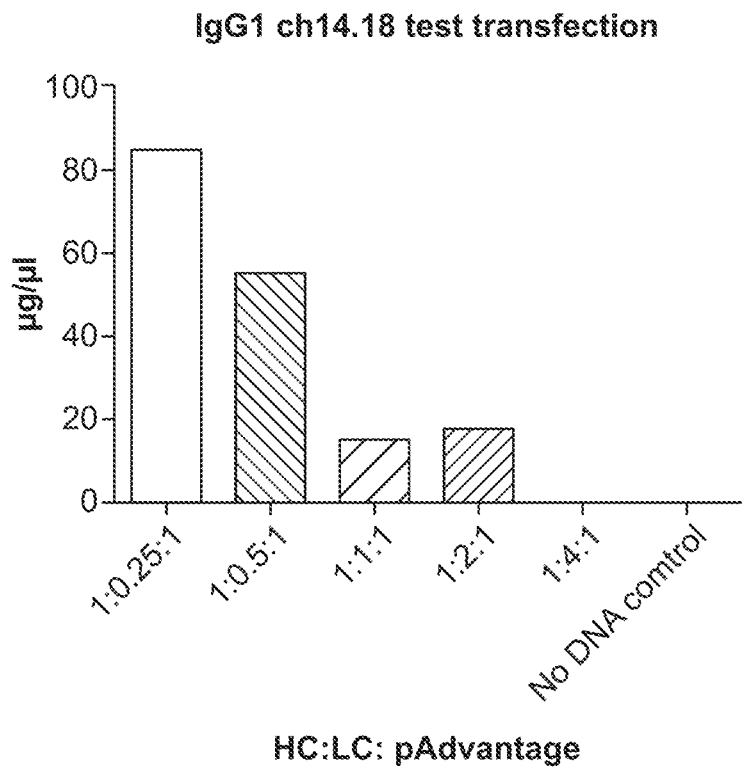
FIG. 2: Quantification of IgA ch14.18 after transfection with several heavy (HC) and light chain (LC) ratio's. 5 different ratios were used for IgG1 and IgA1 production. The optimal ratios were used for larger scale production.
Figure 2B:
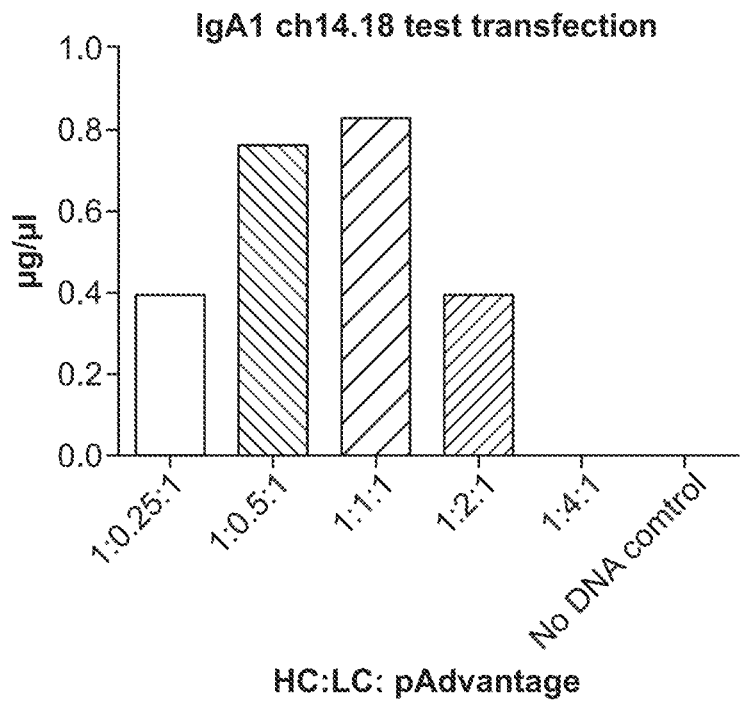

Generation of Anti-GD2 Antibody Producing Vectors:

The amino acid sequences of the variable regions from ch14.18 were found in the FDA application of dinutuximab (application 125516; depicted in FIG. 1). These amino acid sequences were translated to the cDNA sequence representing the most likely non-degenerate coding sequence. The cDNAs were synthesized (Baseclear) and subcloned into the pEE14.4 expression vectors which contain either the IgA1 or IgG1 backbone (described in: Beyer, T., et al. "Serum-free production and purification of chimeric IgA antibodies." Journal of immunological methods 346.1 (2009): 26-37). The optimal ratio of heavy to light chain DNA for transfection was first determined by small scale test transfections in HEK293F cells. Antibody production was then quantified by anti-human IgG (FIG. 2A) or IgA ELISA (FIG. 2B).

Figure 3A:
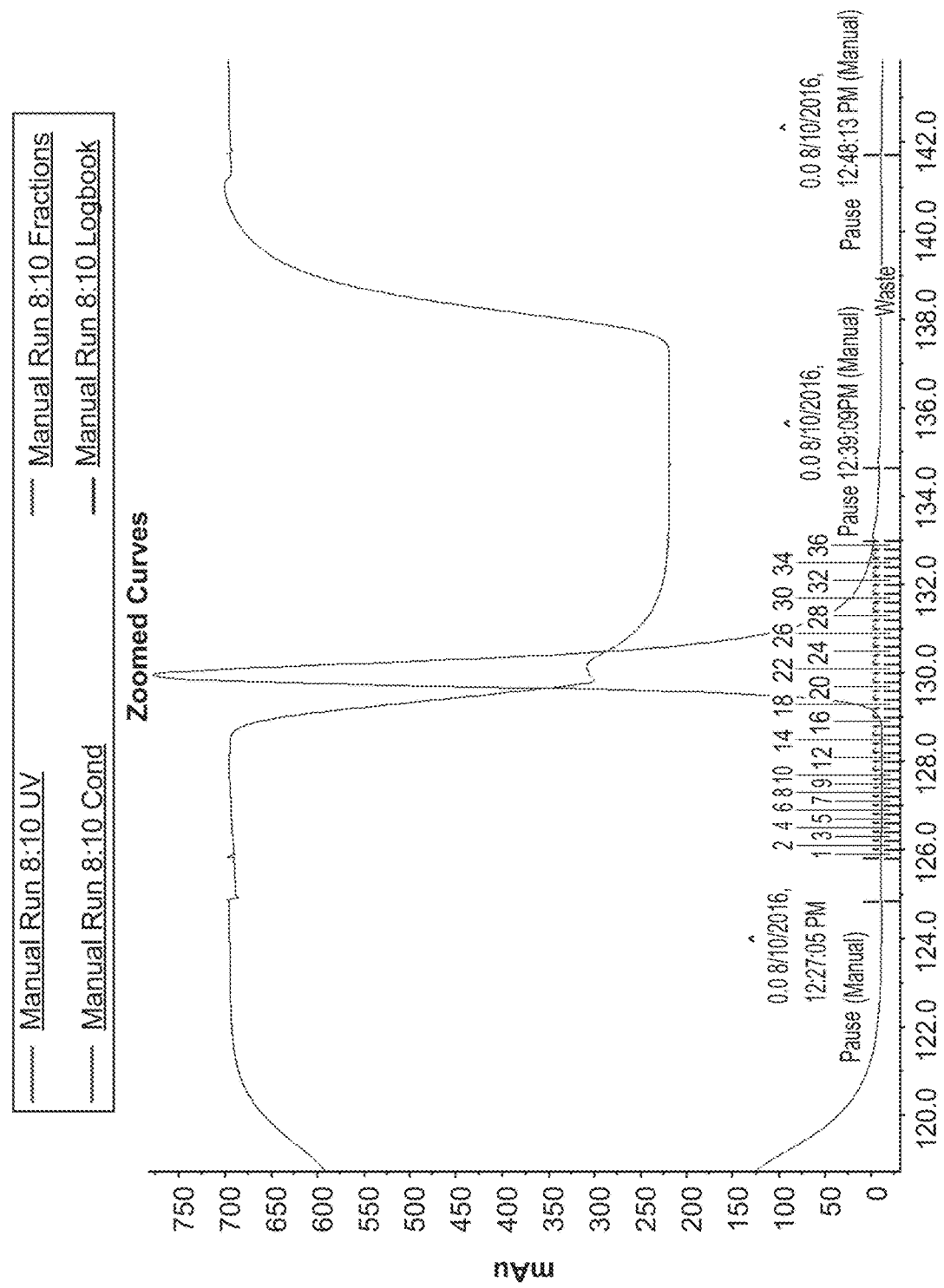
FIG. 3: A: K-light chain specific affinity chromatography of IgA ch14.18. B: Size exclusion chromatography of IgA ch14.18 UV absorption, representing protein concentration, is indicated by the trace.
Figure 3B:
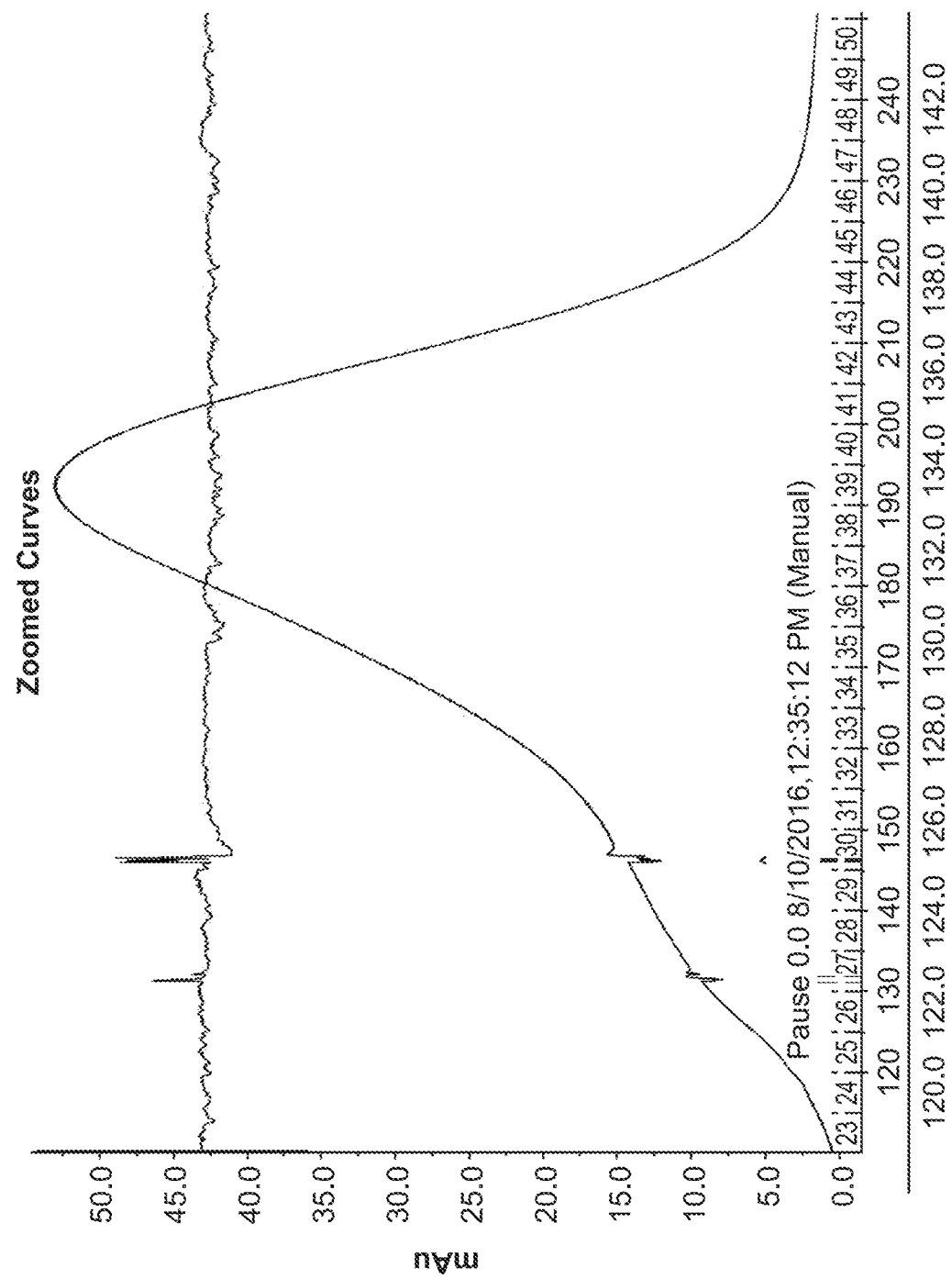

Production was scaled up to allow for antibody characterization and functional assays. Again, HEK293F cells were transfected with the pEE14.4 IgA ch14.18 heavy chain and ch14.18 kappa light chain at the optimal heavy to light chain transfection ratios. The produced IgA antibodies were purified by using a series of two liquid chromatography steps. First, IgA ch14.18 was isolated from the serum free supernatant using human K-light chain specific affinity chromatography (FIG. 3A). Next, size exclusion chromatography with a preparative prepacked Superdex200 26×600 column was used to separate intact IgA from free light chain (FIG. 3B). Finally, IgG antibodies were purified by protein affinity chromatography and were subsequently dialyzed to PBS. This multistep procedure results in highly pure preparations of recombinant monomeric IgA.

Characterization of Anti-GD2 Antibodies

Binding of anti-GD2 antibodies to the GD2 expressing cell lines IMR32 and SK-N-FI was analyzed by staining cells on ice for 45 minutes with anti-GD2 antibody at several concentrations. Cells were washed and a secondary goat-anti human IgA-PE or IgG-PE was added to the cells for 45 minutes on ice in the dark. Afterwards, antibody binding was quantified by flow cytometric analysis.

Complement activation of the produced antibodies was assessed by incubation of IMR32 and SK-N-FI cells with 15% pooled human serum and antibody (10-0.01 µg/ml) for 1 and 4 hours at 37° C. Afterwards, live/dead staining (7-AAD) of cells was performed and cellular lysis was quantified via flow cytometric analysis.

ADCC assays were performed to assess the efficacy of IgA and IgG1 ch14.18 to recruit effector cells against neuroblastoma cells. First, leukocyte ADCC's were performed. Hereto, peripheral blood from healthy donors was treated with RBC Lysis buffer to remove red blood cells. The remaining leukocytes were washed and added to radioactively labeled neuroblastoma cells with or without IL-2 and GM-CSF (both 10 ng/ml). After 4 hours of incubation at 37° C., cell death was quantified by $^{51}$Cr release, measured by liquid scintillation. The percentage of specific lysis was calculated by determining the maximal lysis in the presence of 2.5% triton X-100 and basal cell lysis in the absence of antibodies and effector cells.

To evaluate whether PMNs are an important effector cell population for IgA mediated killing, PMNs were isolated from peripheral blood from healthy donors by ficoll-histopaque and added in a 40:1 E:T ratio to radioactively labelled neuroblastoma cells with or without IL-2 and GM-CSF (both 10 ng/ml).

Results and Discussion

Figure 4A:
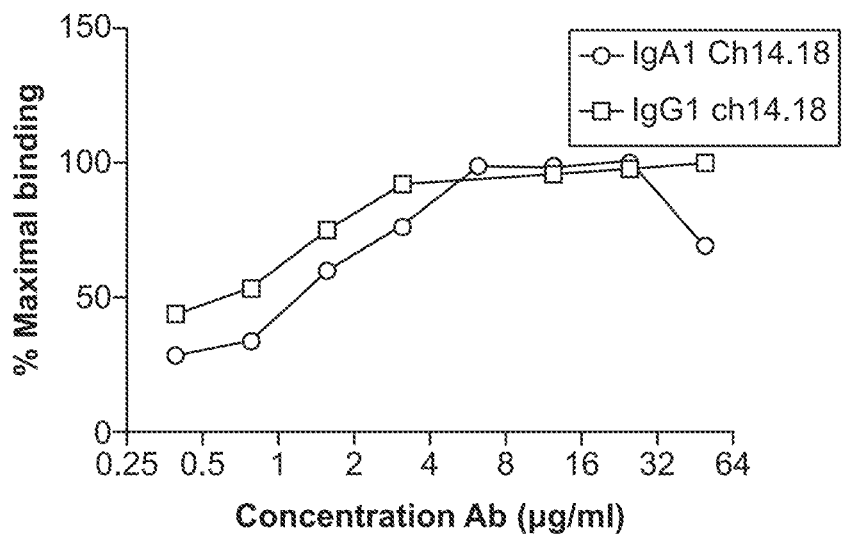
FIG. 4: binding of in-house produced and purified IgG1 and IgA ch14.18 to the GD2 expressing neuroblastoma cell line IMR32 and SK-N-FI in flow cytometry.
Figure 4B:
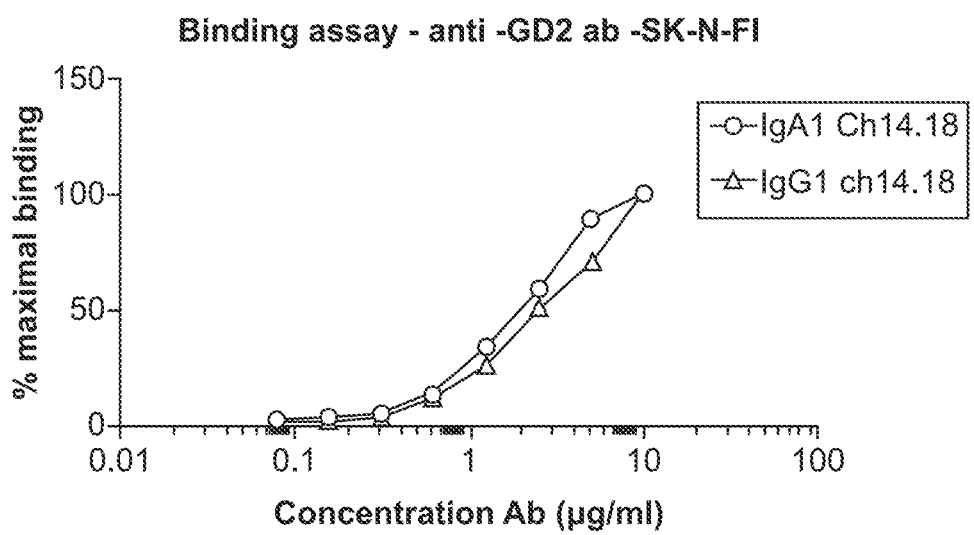
Figure 5A:
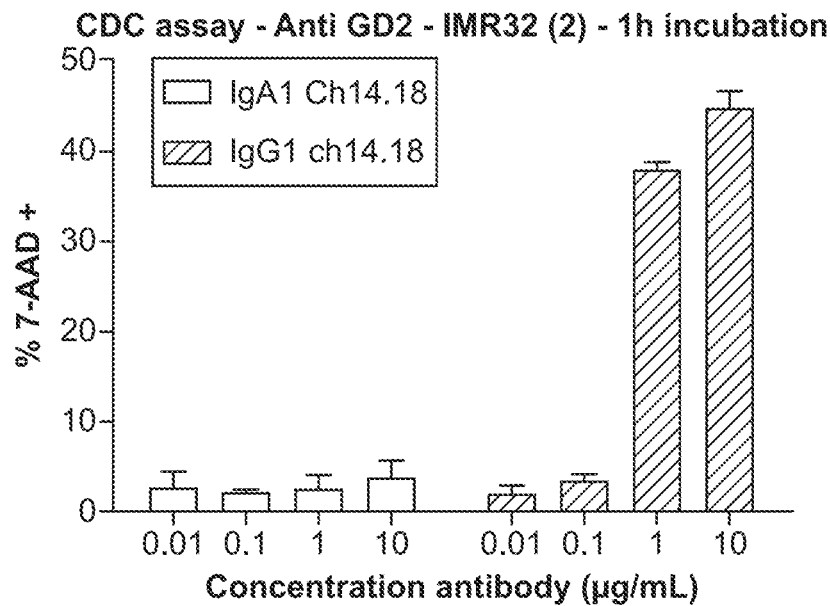
FIG. 5: CDC assay of IgG1 and IgA after 1 hr and 4 hrs of incubation with IMR32 cell line. Cell lysis through complement activation is analyzed by flow cytometric analysis. 15% pooled human serum was added, and cells were incubated for 60 min and 4 hrs at 37° C. The amount of cell lysis is measured by 7-AAD staining.
Figure 5B:
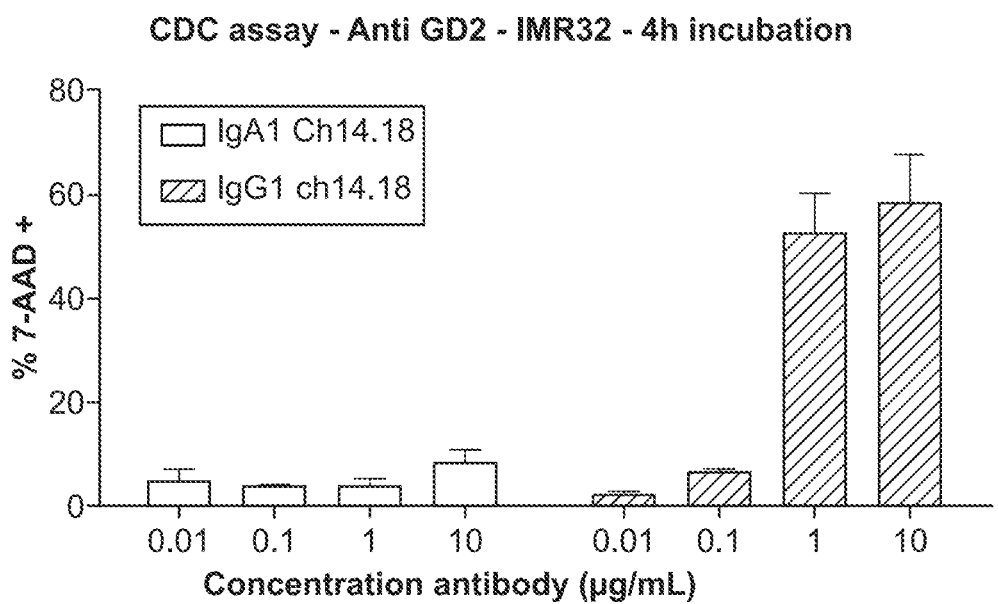
Figure 6A:
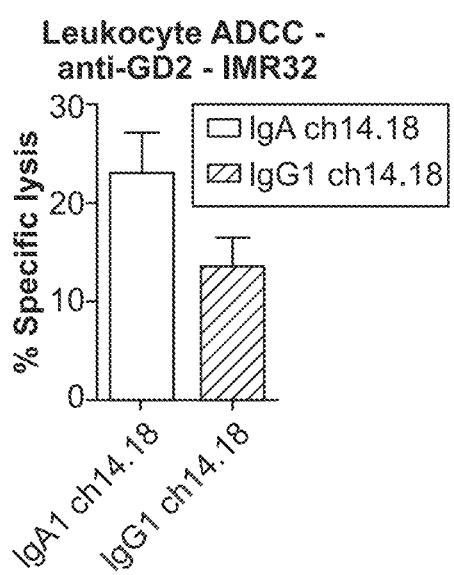
FIG. 6: Leukocyte (Panel A and C) and PMN (Panel B and D) ADCC assay of IgG1 and IgA after 4 hrs of incubation with the IMR32 (Panel A and B) and SK-N-FI (Panel C and D) cell lines. Red blood cells were lysed and the remaining effector cells were added to wells. After 4 hours of incubation at 37° C., $^{51}$Cr release was measured in counts per minute (cpm) by a beta-gamma counter. The percentage of specific lysis was calculated by determining the maximal lysis in the presence of triton and basal lysis in the absence of antibodies and effector cells.
Figure 6B:
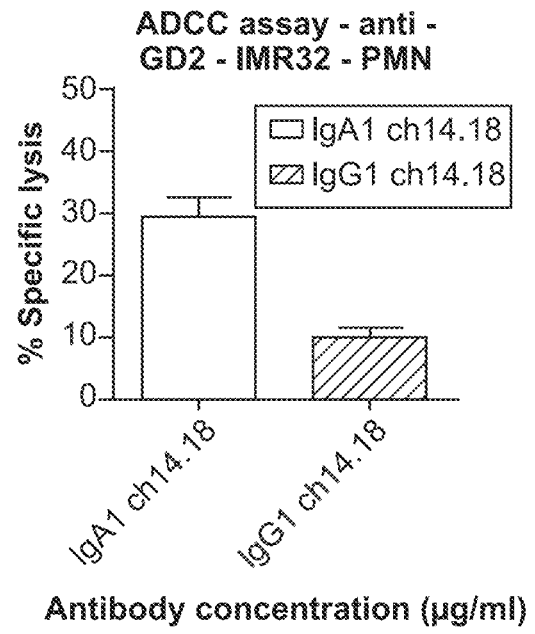
Figure 6C:
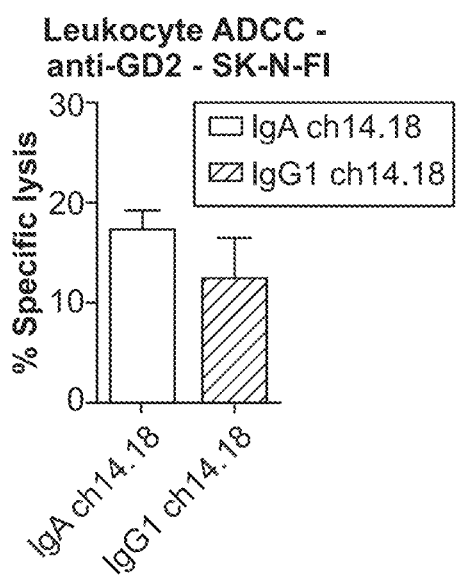
Figure 6D:
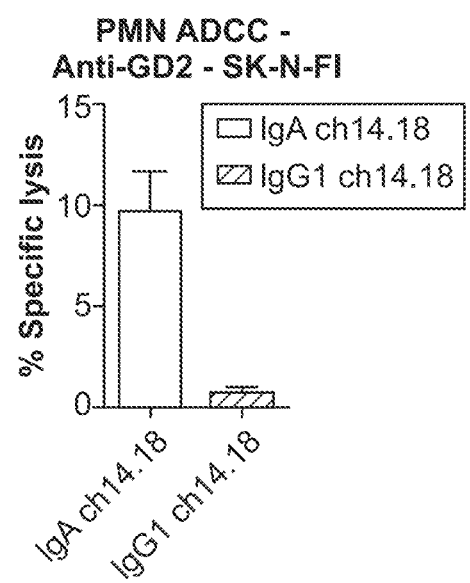
Figure 7A:
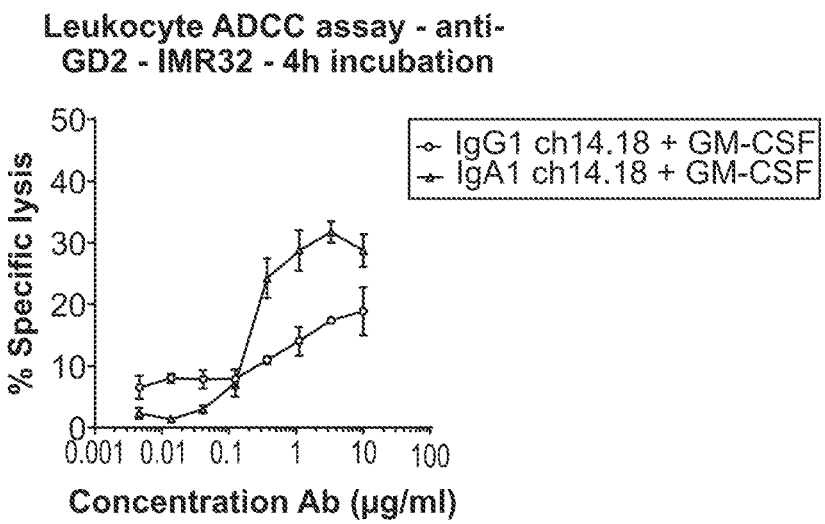
FIG. 7: Leukocyte ADCC assay of in-house produced and purified IgG1 and IgA after 4 hrs of incubation with the IMR32 and SK-N-FI cell line. Red blood cells were lysed and the remaining effector cells were added to wells together with cytokines. After 4 hours of incubation at 37° C., $^{51}$Cr release was measured in counts per minute (cpm) by a beta-gamma counter. The percentage of specific lysis was calculated by determining the maximal lysis in the presence of triton and basal lysis in the absence of antibodies and effector cells.
Figure 7B:
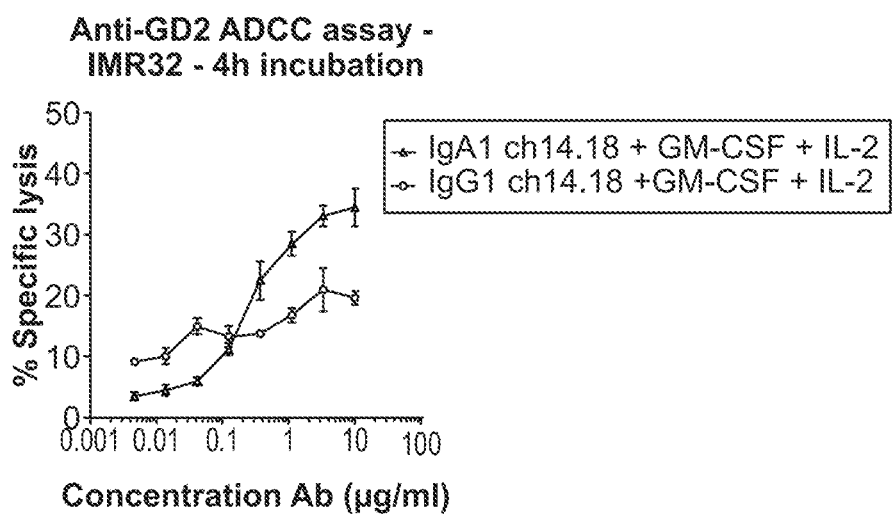
Figure 7C:
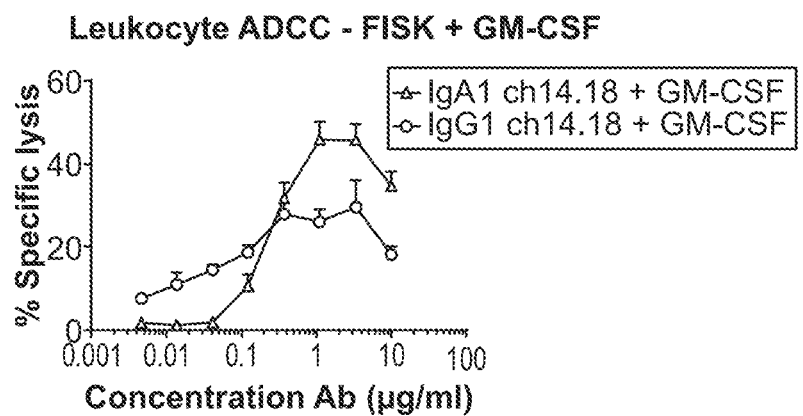
Figure 7D:
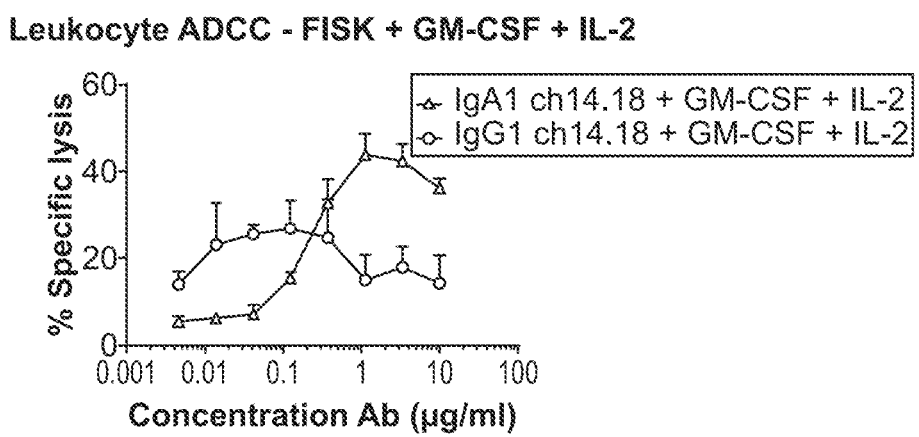
Figure 8A:
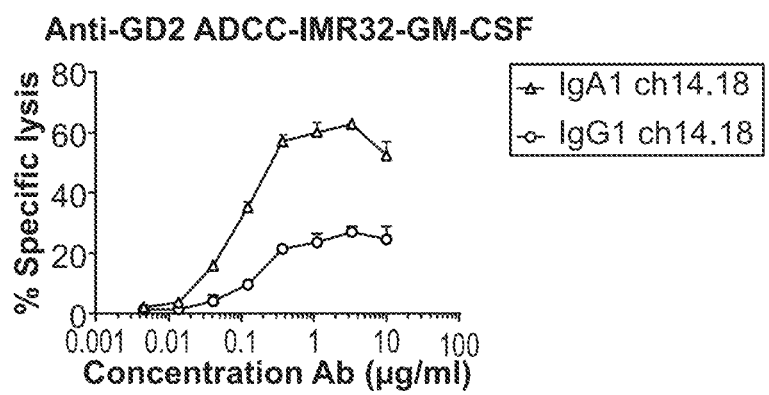
FIG. 8: PMN ADCC assay of IgG1 and IgA ch14.18 after 4 hrs of incubation with the IMR32 or SK-N-FI cell line. PMNs were isolated by Ficoll/Histopaque separation. Subsequently, effector cells, cytokines and antibodies at various concentrations were added to microtiter plates containing target cells. E:T ratios were 40:1 (PMN). After 4 hours of incubation at 37° C., $^{51}$Cr release was measured in counts per minute (cpm) by a beta-gamma counter. The percentage of specific lysis was calculated by determining the maximal lysis in the presence of triton and basal lysis in the absence of antibodies and effector cells.
Figure 8B:
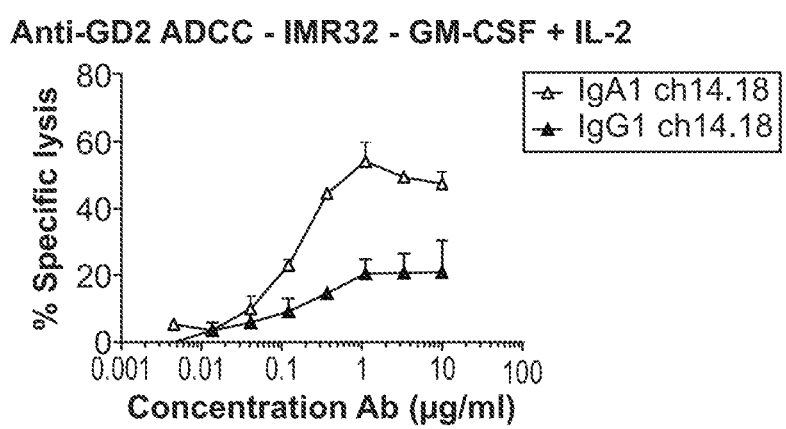
Figure 8C:
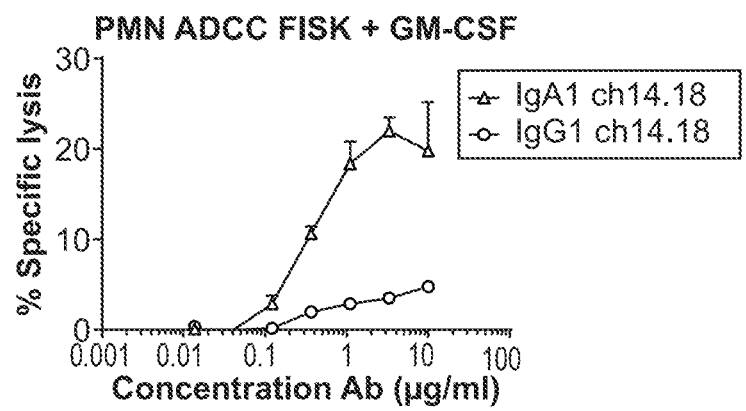
Figure 8D:
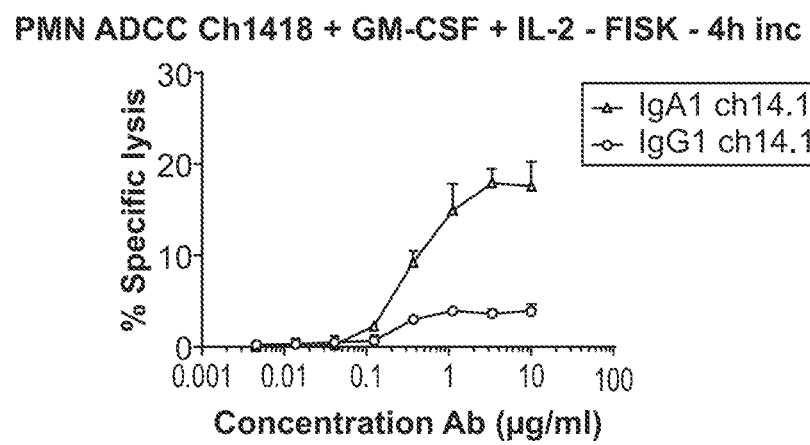

The functional characterization of the antibodies was performed by determining binding capacity to GD2, complement activation and effector cell recruitment. Flow cytometric analysis of binding to the GD2-positive cell lines IMR32 and SK-N-FI showed similar binding patterns for both IgG1 and IgA (FIG. 4). Complement activation of the produced antibodies was assessed by live/dead staining (7-AAD) after incubation with 15% pooled human serum and several concentrations of antibody The IgA anti-GD2 antibody did not show activation of complement, while the IgG1 variant having the same variable regions did activate the complement system after 1 hour of incubation (FIG. 5A). Lysis increased further for IgG when incubation time increased to 4 hours, while for IgA no complement activation was observed (FIG. 5B)

ADCC assays were performed to assess the efficacy of IgA and IgG1 ch14.18 to recruit effector cells against neuroblastoma cells. First, leukocyte ADCC's were performed. Here, the IgA anti-GD2 antibody showed to be superior for both the IMR32 and SK-N-FI cell line (FIG. 6). To evaluate whether PMNs are an important effector cell population for IgA mediated killing, PMN were isolated from peripheral blood from healthy donors. It was shown that the IgA anti-GD2 antibody stimulates PMN better than IgG1 to kill IMR32 and SK-N-FI cells (FIG. 6).

When cells were incubated together with the clinically used cytokine GM-CSF, maximal lysis induced by the IgA anti-GD2 antibody strongly increased, while only minimal effects were seen for the IgG1 variant (FIG. 7). Furthermore, addition of IL-2 did not increase the observed lysis (FIG. 7). Similar effects were observed for PMN mediated ADCC (FIG. 8).

Figure 9A:
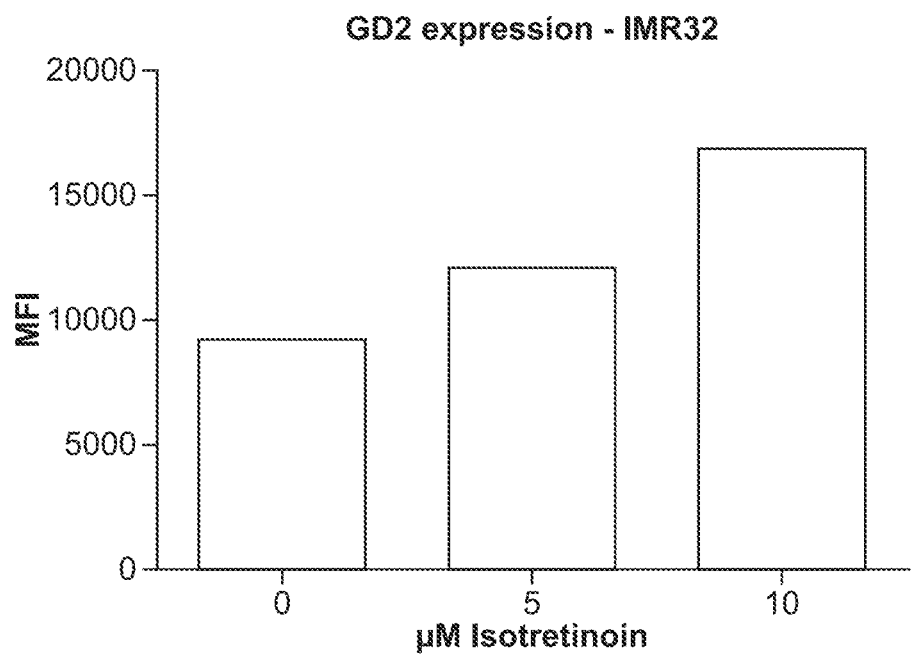
FIG. 9: GD2 (Panel A) and MHC-I (Panel B) expression on IMR32 cells after exposure to different concentrations of isotretinoin for 4 consecutive days. Cells were stained with IgA ch14.18 and detected with a secondary anti-IgA PE or anti-MHC-I-PE.
Figure 9B:
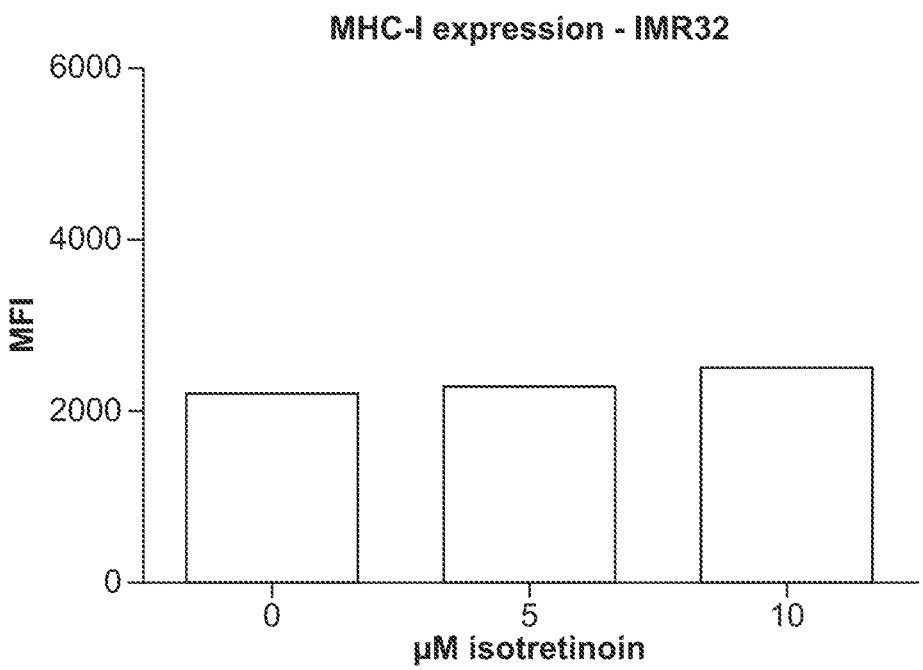
Figure 10:
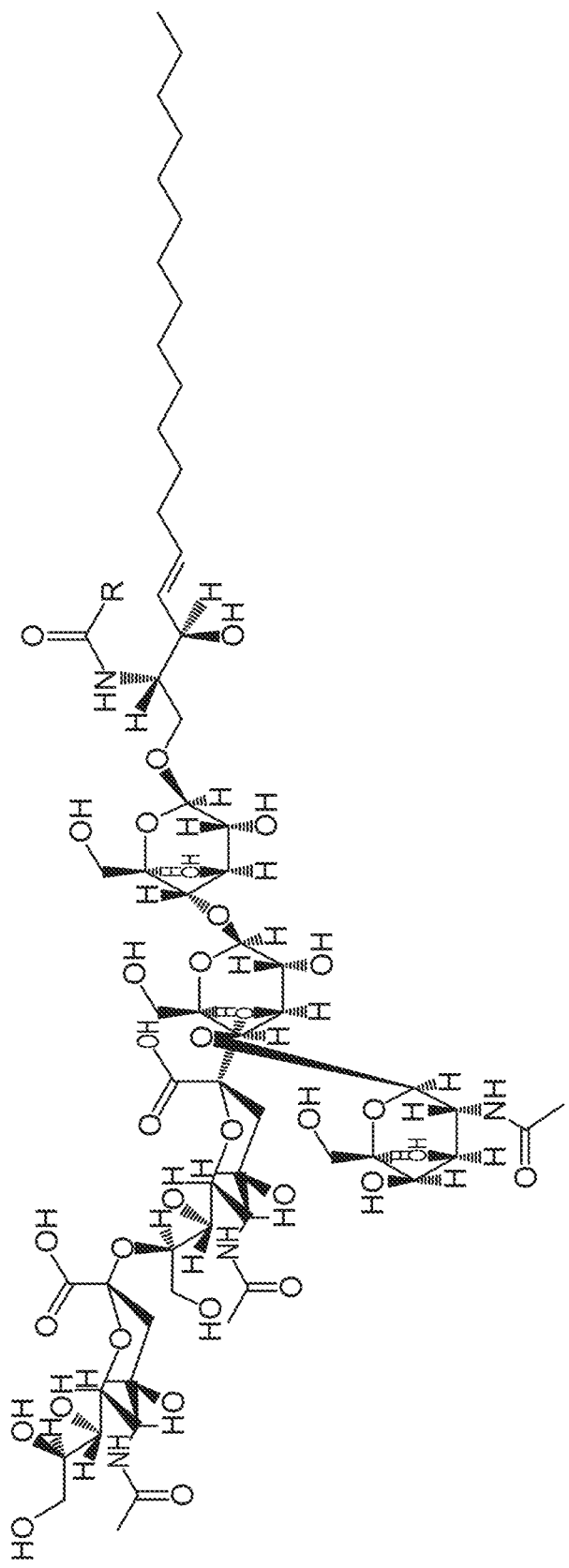
FIG. 10: Schematic representation of the ganglioside GD2.
Figure 11:
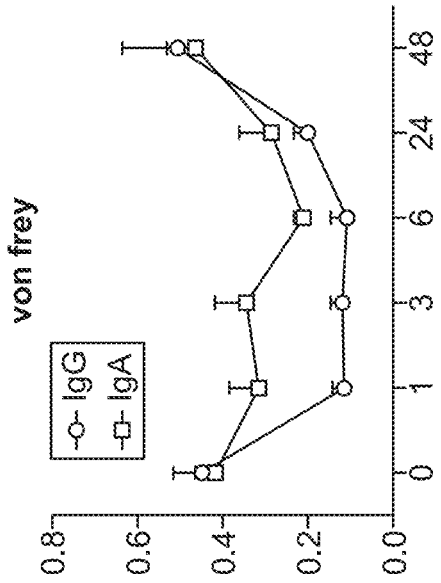
FIG. 11: Quantification of in vivo mechanical thresholds. Experiments were conducted using female (aged 8-12 weeks) C57BL/6 mice (Harlan Laboratories). Mice received an intravenous injection of 100 microgram of antibody. Mechanical thresholds were determined using the von Frey test (Stoelting) with the up-and-down method as is described in Eijkelkamp et al., 2010; J. Neurosci. 30:2138-2149 and Chaplan et al., 1994; J. Neurosci. Methods 53:55-63. All experiments were performed by experimenters blinded to treatment.
Figure 12B:
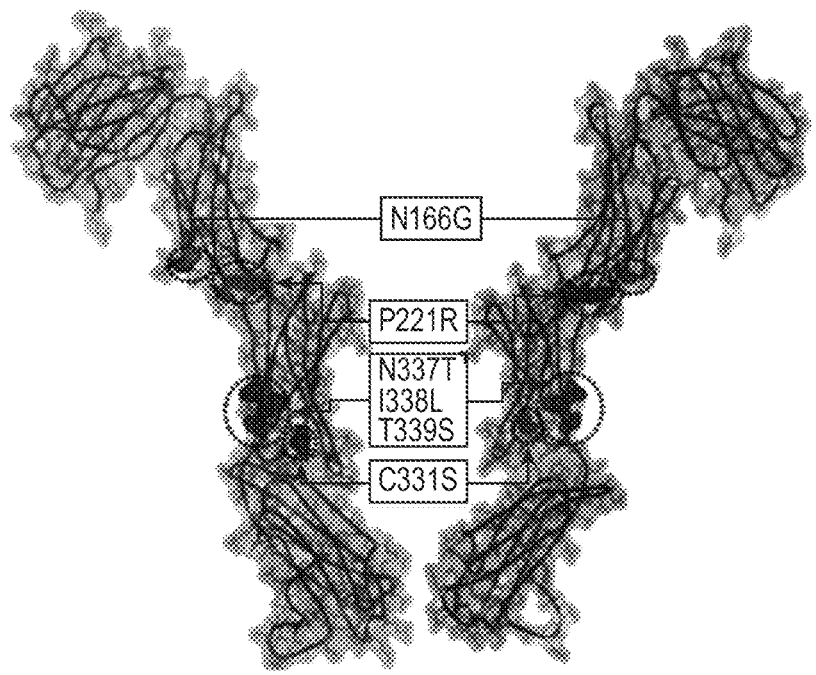
FIG. 12: Primary sequence and modeling of the IgA1/IgA2.0 hybrid antibody. A, alignment of primary sequences of the constant regions of hIgA1 (SEQ ID NO: 12), IgA2m (1) (SEQ ID NO: 11), and a IgA1/IgA2m(1) hybrid (hIgA2.0) (SEQ ID NO: 13). Residues are numbered according to the myeloma IgA1 protein (Bur) scheme. Domain boundaries are indicated by vertical lines above the sequences. The following features are highlighted: light gray underlined residues are unique for IgA1, dark gray underlined asparagines are conserved N-glycosylation consensus sequences, and black underlined residues are unique for IgA2.0. B, the heavy chain of 225-IgA2.0 was modeled and illustrated in front and side view, with mutations marked. C, heavy chains of wild-type and mutant IgA2 were modeled. The resulting alignment indicates a different orientation of C241 in the heavy chains of IgA2-wt compared with IgA2.0, possibly due to the P221R mutation. D, focus on the tailpiece of 225-IgA2-wt (green, C471; red, Y 472) and IgA2.0 (red). Prediction and alignment of models were performed using I-TASSER; models were modified in 3D-Mol Viewer. E, nucleic acid sequence and protein sequence of the constant regions of the heavy chain of IgA2.0.
Figure 12C:
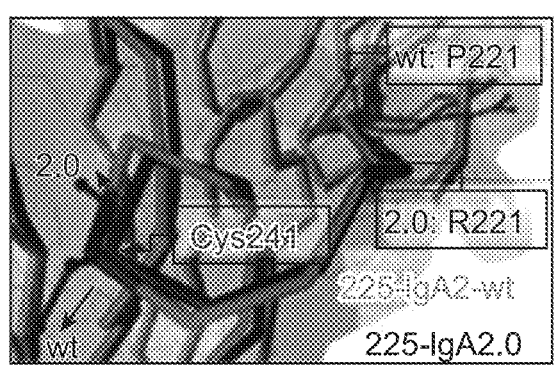
Figure 12D:
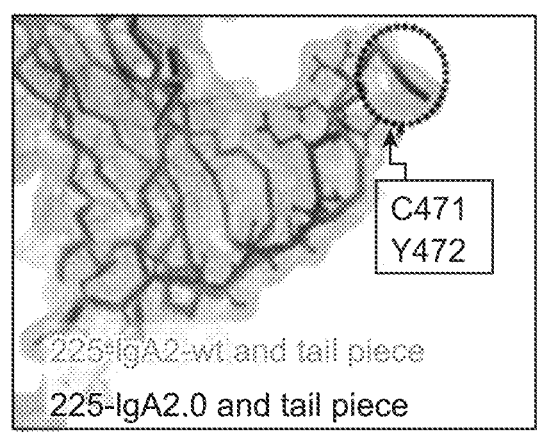

We also show that treatment of neuroblastoma cell lines with isotretinoin is able to influence GD2 expression. It was shown that after 4 days of incubation with isotretinoin, binding of IgA ch14.18 is increased, while MHC-I expression remained stable (FIG. 9).

The examples show that an IgA isotype variant of dinutuximab has higher ADCC capacity for killing of neuroblastoma's, and no complement activation. The IgA anti-GD2 antibody enhances destruction of neuroblastoma cells, whereas side effects such as neuropathic pain are reduced.

In the present invention it is shown that isotype conversion of dinutuximab to IgA provides a solution to one or more of the toxicity problems of the dinutuximab antibody. The antibody of the invention provides potent ADCC activity while simultaneously reducing at least the pain problem associated with dinutuximab administration. Antibodies of the invention efficiently activate neutrophils presumably through the FcαR (CD89). This generates potent anti-tumor reactions. The susceptibility of neuroblastoma cells to an antibody of the invention shows that an IgA anti-GD2 exhibits improved efficacy against neuroblastoma when compared to an IgG isotype variant with the same variable domains, and simultaneously reduces treatment toxicity. This significantly improves anti-neuroblastoma immunotherapy.

Antibody function is governed by a number of factors. The target and the epitope that is recognized play an important role as does the cell on which the target resides. Effector functions of the antibody are often correlated with the isotype of the antibody. Although this is useful as a general rule, many exceptions indeed exist. This is exemplified for instance for ADCC activity by Rajasekaran et al (Rajasekaran et al., 2015; ImmunoTargets and Therapy Vol 4: 91) and for CDC activity by Lohse et al., 2017; Br J Haematol. doi:10.1111/bjh.14624dgf; and Pascal, et al., (2012) Haematologica 97.11: 1686-1694).

Conversion of IgG to IgA can alter the receptors which interact with the antibodies. For IgG, the activating Fc gamma receptors (FcγR), bearing an ITAM motif, are the principal mediators of antibody mediated activation of leukocytes. Inhibitory FcγRs and polymorphisms in FcγRs interfere with these effects. This can make IgG treatment less suitable for subgroups of patients. We and others have shown that IgA also exerts anti-tumor effects through an Fc receptor, the FcαR, which is expressed on neutrophils, monocytes and macrophages. Inhibitory receptors and polymorphisms are not reported for FcαRII. However, the FcαRI is not expressed in mice, making it for a long time not possible to do the necessary preclinical in vivo studies with IgA therapeutic antibodies. However, within our laboratory the human FcαRI transgenic mouse was generated. This mouse has a similar expression pattern of human FcαRI as in humans. These mice were back-crossed in the relevant backgrounds, i.e. balb/c, C57B/L6, and SCID for growing human tumors.

IgA as Therapeutic Antibody.

Although IgA is known as a mucosal antibody, in its monomeric form it is the second class of antibody present in the human serum. In previous studies we have shown that an anti-tumor antibody IgA can be effective in vitro. The anti-tumor mechanism is different and mainly through the recruitment of neutrophils, the most abundant type of leucocytes. Also in vivo IgA can be efficacious as a therapeutic antibody. A drawback of an IgA molecule is its on average relatively short half-life, due to different glycosylation and lack of binding to the neonatal Fc receptor, FcRn. The present invention solves this problem for GD2 specific IgA antibodies by providing them with adapted glycosylation and targeting of the IgA to FcRn indirectly (Meyer et al., 2016 MAbs Vol 8: pp 87-98).

In the present invention we show that anti-GD2 IgA isotype antibodies are targeting neuroblastoma, in vitro, in vivo and in patient-derived models.

Example 2

The efficacy of the anti-GD2 antibodies to elicit ADCC, will be assay against a further panel of GD2 expressing neuroblastoma cell lines (e.g. IMR-32, SH-SY5Y, SK-N-FI, LAN-5), from ATCC) and ex vivo neuroblastoma cells as targets. In addition, the panel will include tumor-initiating cells that have been generated from primary neuroblastoma samples and that contain stem cell-like cells that may represent the chemotherapy-resistant cell population responsible for resistance to conventional chemotherapy (such as described in Bate-Eya, et al., 2014; European journal of cancer 50.3: 628-637). Both whole blood and isolated effector populations from healthy volunteers and patients will be used as effector cells. Practically, target cells will be labelled with $^{51}$Cr for 2 hours. PMNs and PBMCs will be isolated by Ficoll/Histopaque separation. Subsequently, effector cells, antibodies at various concentrations, and medium will be added to microtiter plates containing target cells. E:T ratios will be 40:1 (PMN) and 50:1 (PBMC). After 4 hours of incubation at 37° C., $^{51}$Cr release will be measured in counts per minute (cpm). The percentage of specific lysis will be calculated by determining the maximal lysis in the presence of triton and basal lysis in the absence of antibodies and effector cells.

Testing on Organoids Derived from Neuroblastoma Patients

We have generated tumor-derived organoids from primary neuroblastoma samples. Tumor-derived organoids reflect tumor heterogeneity and allow performing these functional tests on tissues representing primary tumor tissue. We will use the IgA dinutuximab on these organoids. We will evaluate binding, ADCC microscopically by death markers and complement depositions with C1q and iC3b detecting antibodies.

In Vivo Experiments in FcαR Transgenic Mice

For in vivo experiments, we will make use of syngeneic models, xenograft models and patient derived xenograft (PDX) models.

For syngeneic models, we will make use of the TH-MYCN 9464D-based syngeneic neuroblastoma mouse model, grown orthotopically or subcutaneously. For xenograft models we will make use of the HTLA-230 NB cells implanted in SCID mice, as described in Bogenmann 1996 Int. J. Cancer Vol 67: 379; and Raffaghello et al., 2003 Cancer Lett, Vol 197(1-2): p. 205-9. Previously, the anti-GD2 antibody 14G2a was tested in this model, and it was shown that it worked very efficiently, but still in the absence of NK cells and macrophages (Raffaghello et al., 2003 supra). That fits with the notion that neutrophils are important effector cells for dinutuximab. When we will test IgA in these mice, we will use the SCID/FcαR transgenic mice, available in our laboratory, since mice lack the FcαR. We will compare the efficacy of IgG and IgA in these transgenic SCID mice.

For PDX models we will make use of the NSG mice (NOD/SCID/gamma$^{null}$ mice). These models allows for orthotopic positioning of patient tumors, outgrowth and subsequent treatment (Braekeveldt et al., 2016 Cancer Lett. Vol 1; 375(2):384-9. doi: 10.1016/j.canlet.2016.02.046).

Example 3

Improvement in neuroblastoma patient survival came in 2015, with the FDA approval of ch14.18, a chimeric antibody of the IgG1 isotype directed against the ganglioside GD2, expressed on neuroblastoma cells, but also on peripheral and central nervous tissue. Ch14.18 is given as second-line treatment in combination with IL-2, GM-CSF and 11-cis retinoic acid for the treatment of high-risk neuroblastoma after hematopoietic stem cell transplantation. In a large phase III clinical trial (n=226) it was shown that ch14.18 combination therapy resulted in 20% more event-free survival than standard therapy and 10% more overall survival, 2 years after treatment (Yu et al. 2010, N Engl J Med 363(14): 1324-1334). Although the inclusion of immunotherapy improved the survival of neuroblastoma patients, there are important side effects caused by the administration of ch14.18. Of these, severe neuropathic pain is the most frequent (Yu et al. 2010, N Engl J Med 363(14): 1324-1334). This is believed to be caused by ch14.18 binding to GD2 on A6 and C pain fibers and activates the complement system locally, which is the cause for the observed pain (Xiao et al 1997, Pain 69(1-2): 145-151). This pain does not respond well to analgesics and can be dose limiting (Gilman et al 2009, J Clin Oncol 27(1): 85-91). Ch14.18-antibody-opsonized tumor cells can be killed by leukocytes through antibody-dependent cell-mediated cytotoxicity (ADCC), depending on antibody binding to Fc receptors on leucocytes. Ch14.18 is also able to activate the complement system on the tumor cell surface, causing lysis of the cell via complement-dependent cytotoxicity (CDC). For ADCC mediated by IgG1 antibody therapy, natural killer (NK) cells are regarded as important cells for mediating ADCC. For neuroblastoma, there is evidence that granulocytes also play a role in mediating ADCC when treated with an anti-GD2 IgG1 antibody (Bruchelt et al 1989, Immunol Lett 22(3): 217-220; Gilman et al 2009, J Clin Oncol 27(1): 85-91; Cheung et al 2012, J Clin Oncol 30(4): 426-432).

Results

Production and Purification of IgG1 and IgA1 ch14.18

Figure 13A:
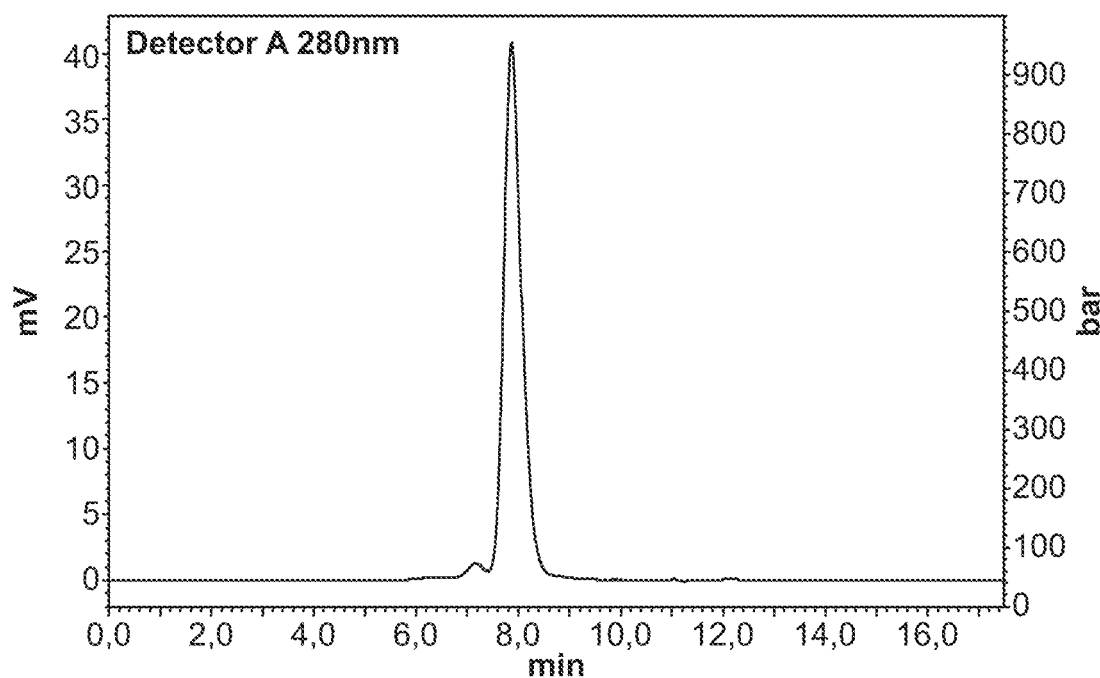
FIG. 13: HP-SEC analysis of IgA1 and IgG1 ch14.18. Purified antibodies were subjected to HP-SEC analysis. Both IgA1 ch14.18 (A) and IgG1 ch14.18 (B) showed to be highly monomeric. Traces show the UV absorbance at 280 nm.
Figure 13B:
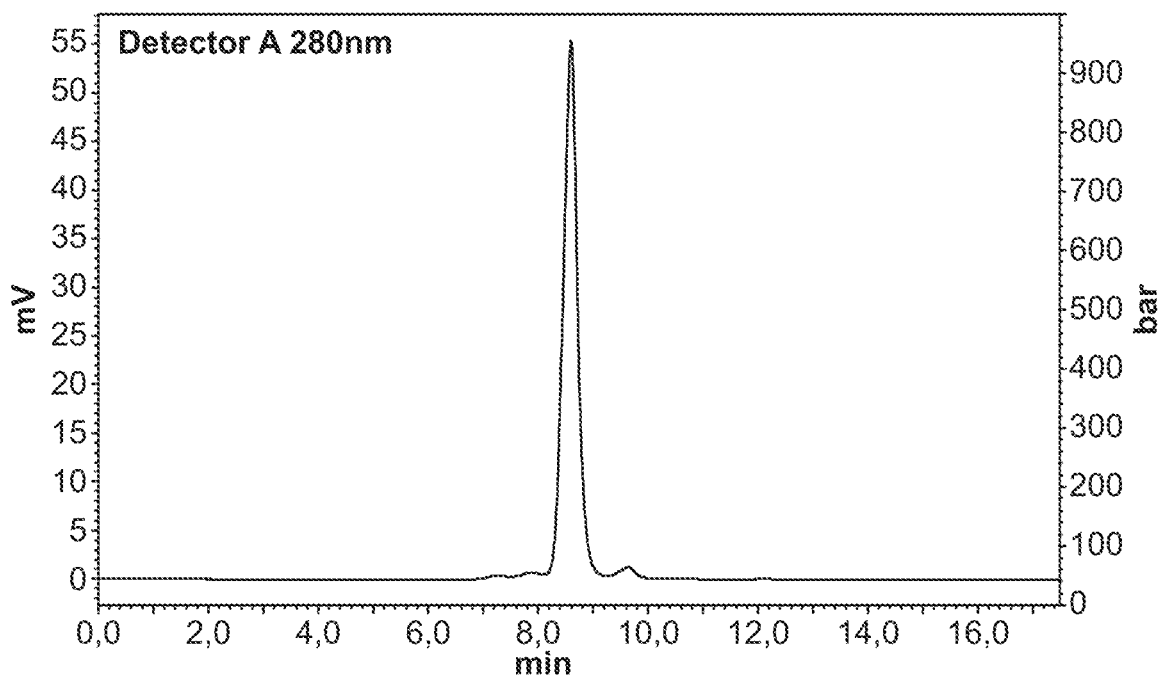

To compare IgA1 and IgG1 antibodies with the ch14.18 variable region, both antibodies were produced and purified in-house. All antibodies were analyzed by HP-SEC to confirm their purity. Both IgA1 ch14.18 (FIG. 13A) and IgG1 ch14.18 (FIG. 13B) were shown to be monomeric, with a purity greater than 95%.

IgA1 and IgG1 ch14.18 Specifically Bind GD2 with Similar Affinity

Figure 14A:
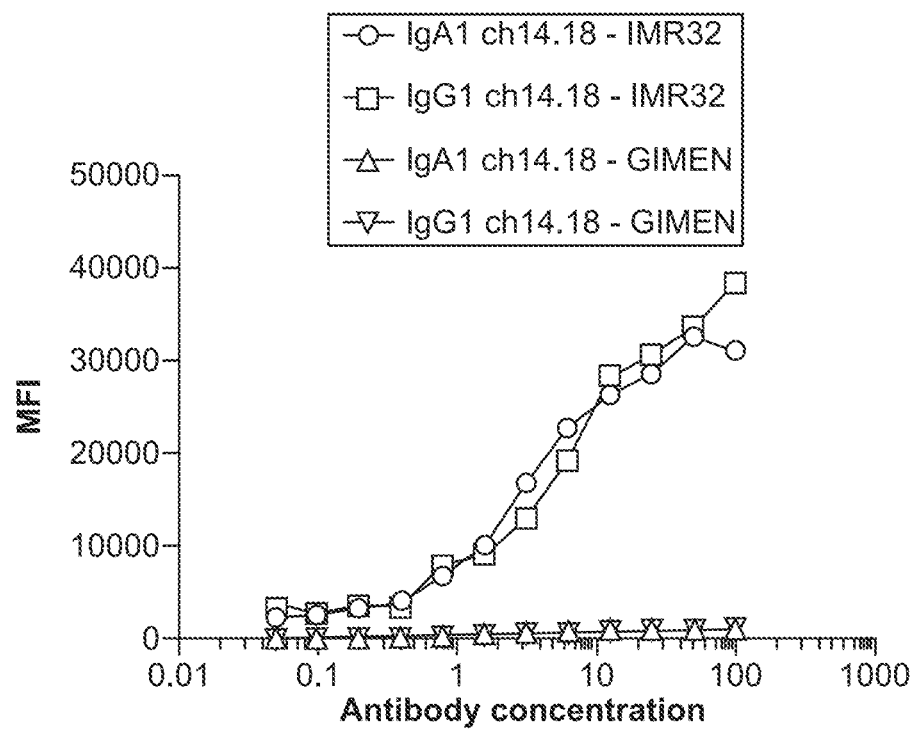
FIG. 14: Binding of IgG1 and IgA1 ch14.18 antibodies to neuroblastoma cell lines. (A) Antibody binding of IgA1-FITC and IgG1-FITC ch14.18 to GD2 expressing neuroblastoma cell line IMR32 and GD2-negative cell line GI-ME-N(B) Real time cell-based affinity measurement of neuroblastoma antibodies on IMR32 cells. IMR32 cell lines were treated with 10 nM of antibody for 1 hour Subsequently, concentration was increased to 20 nM of antibody for 1 hour). Dissociation was followed from 130-250 minutes by replacing antibody containing medium with medium without antibody. Calculated affinities from cell-based affinity measurements are shown in B.
Figure 14B:
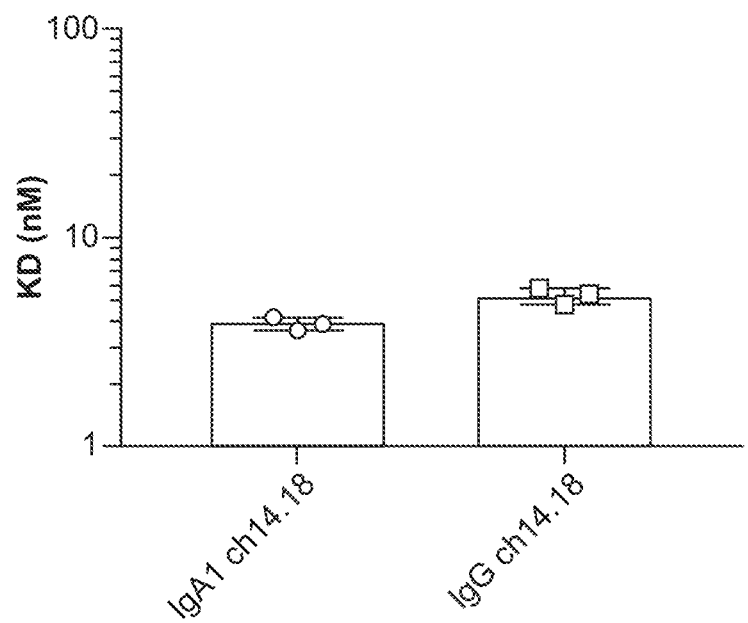

Next, we determined the binding of IgA1 and IgG1 ch14.18 to a panel of neuroblastoma cell lines. Both antibodies recognized the GD2 expressing neuroblastoma cell line IMR-32 similarly, while the GI-ME-N cell line without GD2 expression was not bound (FIG. 14A). To establish whether the affinity of the antibodies remained unchanged after changing the isotype to IgA1, we performed real time cell-based affinity measurements on IMR-32 cells with Ligand Tracer. The antibodies closely follow the same association pattern at 2 different concentrations (10 and 20 nM respectively) and also overlap in the dissociation phase). The assays indicate that the calculated affinity to IMR32 cells did not differ significantly between IgA1 and IgG1 (3.8 nM vs 4.8 nM) (FIG. 14B).

Mechanism of Action of IgA1 and IgG1 ch14.18 Antibodies

Figure 15A:
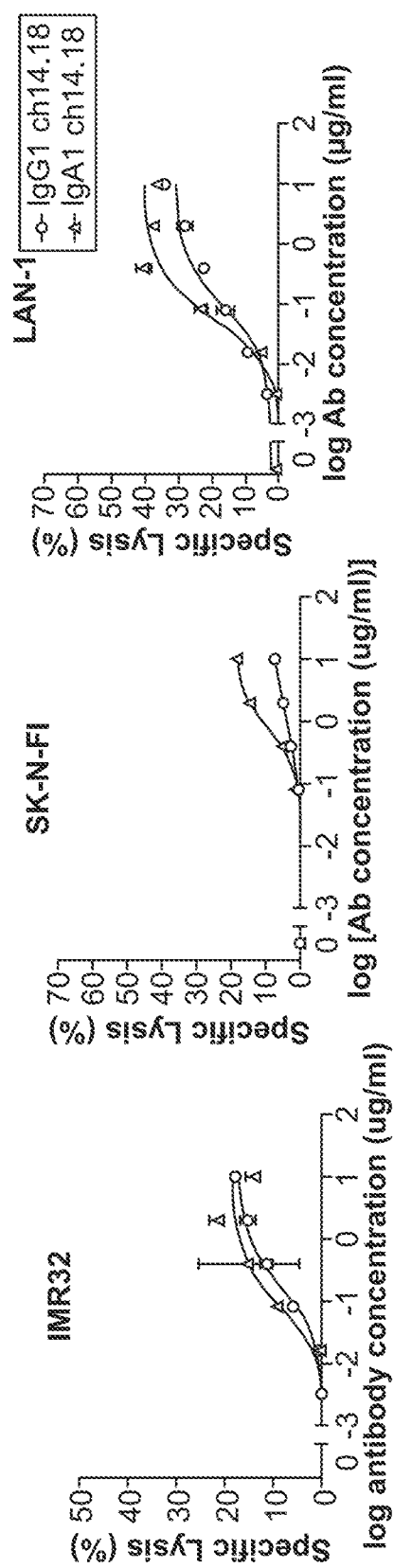
FIG. 15: Characterization of ADCC by IgA1 and IgG1 ch14.18 against a panel of neuroblastoma cell lines. (A) ADCC assays with IgA1 and IgG1 ch14.18 on 3 different neuroblastoma cell lines with leukocytes from peripheral blood as effector cells. (B) ADCC assays with IgG1 ch14.18 on IMR-32cell line with isolated PBMC's (E:T ratio of 100:1) or h isolated neutrophils (E:T ratio of 40:1) as effector cells (C) ADCC assays with IgG1 ch14.18 on IMR32 cell line with isolated PBMC's (E:T ratio of 100:1) or isolated neutrophils (E:T ratio of 40:1) as effector cells with co-treatment of 10 ng/ml GM-CSF, 6545 U/ml of IL-2 and 24 hours of pre-incubation with 10 µM of 11-cis retinoic acid. (D) ADCC assays with leukocytes from peripheral blood as effector cells in combination with 15% pooled human complement active serum.

Subsequently, we compared the in vitro mechanism of action of these antibodies. Both ADCC and CDC are known to be induced by ch14.18 against neuroblastoma in vivo. To compare killing with a mix of effector cells, ADCC assays were performed on IMR-32, SK-N-FI and LAN-1 neuroblastoma cell lines with leukocytes as effector cells. Both IgA and IgG antibodies lysed IMR-32 cells to a similar extent, while SK-N-FI and LAN-1 cells were killed better with IgA1 ch14.18 (FIG. 15A). The GI-ME-N cell line, that has no detectable GD2 expression on FACS could not be lysed by both antibodies, showing that GD2 expression is a prerequisite for ADCC (data not shown). To evaluate the relative importance of certain leukocyte subsets in mediating ADCC, neutrophils and peripheral blood mononuclear cells (PBMC) were separately used as effector cells to determine their respective cytotoxic capacity against neuroblastoma cell lines with these antibodies.

Figure 15B:
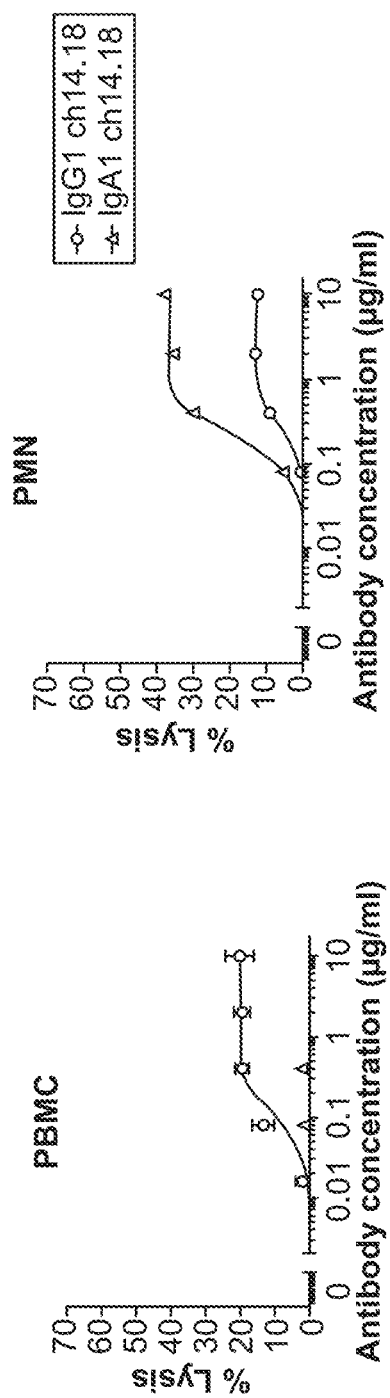

With PBMC's as effector cells, IgG1 ch14.18 effectively lysed IMR32 cells, while lysis with the IgA antibody did not perform as well (FIG. 15B). This was also seen for 2 other neuroblastoma cell lines (data not shown) On the contrary, when neutrophils were used as effector cells, IgA ch14.18 mediated superior ADCC for all tested cell lines in comparison to IgG1 (FIG. 15B).

In the clinic, ch14.18 is administered as combination therapy with GM-CSF, IL-2 and retinoic acid. Next, the impact of these compounds on ADCC was assessed for both antibodies. When PBMCs were used as effector cells, addition of GM-CSF did not increase ADCC by IgG1. Combination of GM-CSF and IL-2 led to a minor increase of cell death, even without the presence of antibody, showing increases in PBMC-mediated killing regardless of antibody. Finally, addition of pre-treatment of 11-cis retinoic acid for 24 hours to the previous combination showed further increases in killing for the IMR32 and SK-N-FI cell lines (FIG. 15C). With IgA, no antibody dependent killing could be induced by PBMC's, but cells were lysed in presence of IL-2 and the combination with cis-retinoic acid, indicating antibody independent recognition of neuroblastoma cells by PBMC's (data not shown). Different from IgG1, GM-CSF in combination with IgA1 ch14.18 boosted ADCC with neutrophils as effector cells (FIG. 15C). Presence of IL-2 did not further increase neutrophil mediated killing, while maximal lysis increased with pre-exposure to 11-cis-retinoic acid. For IgG1 antibodies, GM-CSF improved killing with neutrophils slightly, while addition of IL-2 or retinoic acid did not enhance killing further (data not shown).

Finally, ADCC assays were supplemented with human pooled serum to investigate whether CDC could enhance neuroblastoma cell lysis. For both IgG1 and IgA1 ch14.18 no significant differences in lysis were observed after addition of serum (FIG. 15D).

IgA1 ch14.18 does not Activate Complement

Figure 16A:
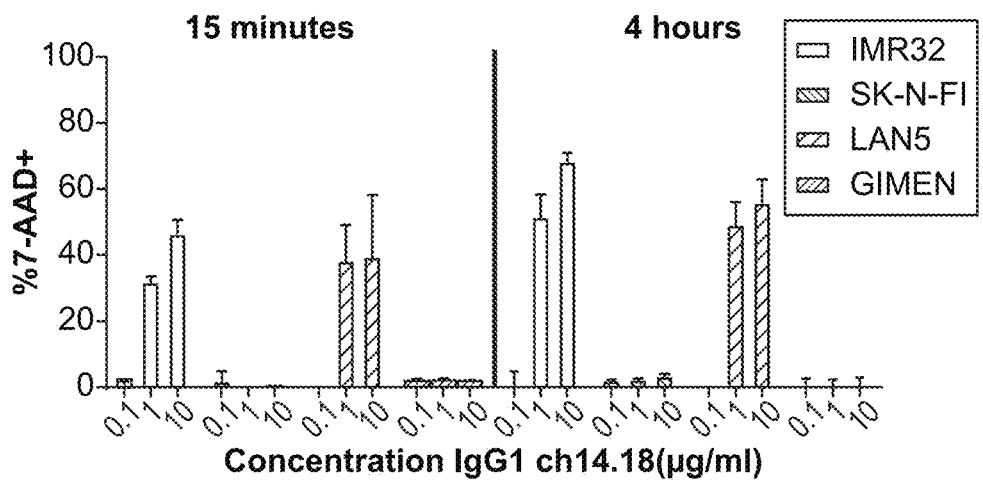
FIG. 16: Complement assays on a panel of neuroblastoma cell lines by IgG1 and IgA1 ch14.18 antibodies. (A) Lysis by IgG1 ch14.18 antibodies on 4 different neuroblastoma cell lines. Cells were incubated with 4 different concentrations of antibody and 15% serum for 15 minutes and 4 hours. (B) Lysis by IgA1 ch14.18 antibodies on 4 different neuroblastoma cell lines. Cells were incubated with 4 different concentrations of antibody and 15% serum for 15 minutes and 4 hours. (C) Expression of complement regulatory proteins CD46, CD55 and CD59 on neuroblastoma cell lines.
Figure 16B:
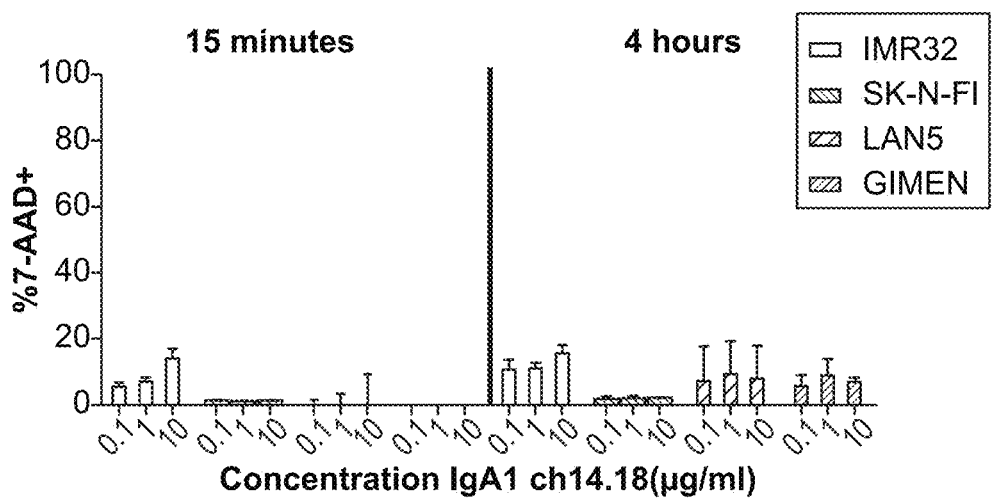
Figure 16C:
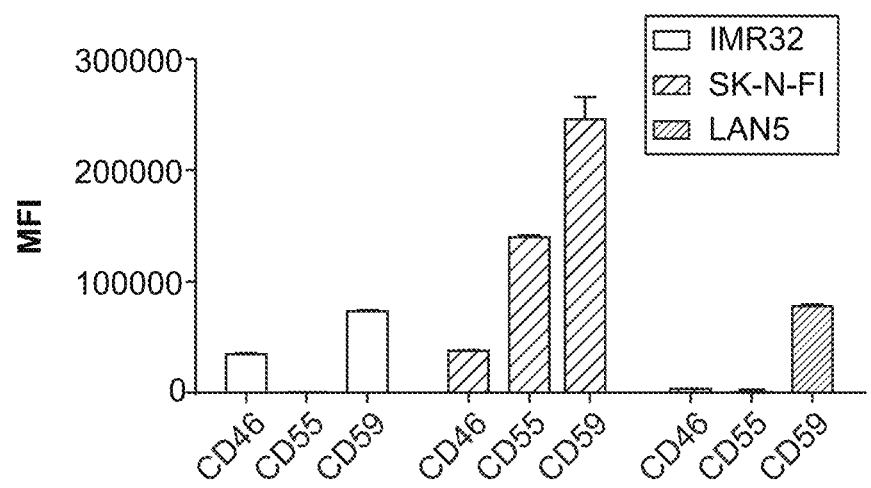

A second effect mediated by ch14.18 is activation of the complement system. Ch14.18 is known to lyse neuroblastoma target cells via CDC in vitro. We assessed in vitro complement activation by these antibodies on the same panel of neuroblastoma cell lines as were used in ADCC assays. IgG1 ch14.18 lysed all tested neuroblastoma cell lines except SK-N-FI via CDC after 15 minutes (FIG. 16A). Contrary to this, no lysis could be observed for IgA1 ch14.18 (FIG. 16B). With longer incubation for 1 hour, the amount of lysis further increased for IgG1, but cells remained negative for 7-AAD with IgA1 (FIG. 16A,B). Since the amount of complement regulatory proteins CD55 and CD59 on SK-N-FI is significantly higher than on the other tested neuroblastoma cell lines, this cell line seems to be less prone to complement mediated lysis (FIG. 16C).

IgA1 Excels in Tumor Cell Depletion In Vivo in Comparison to IgG1 ch14.18

Figure 17A:
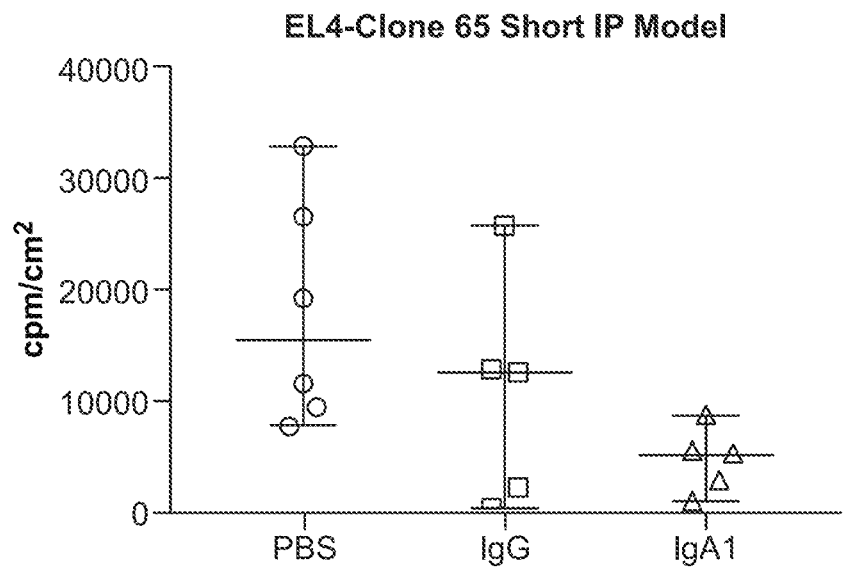
FIG. 17: In vivo efficacy of IgG1 and IgA1 ch14.18 antibodies. (A) Quantification of bioluminescent signal of neuroblastoma cells after 24 hours of treatment with IgA1 or IgG1 ch14.18. (B)) Quantification of bioluminescent signal at 3 days of treatment after I.V. injection of tumor cells.
Figure 17B:
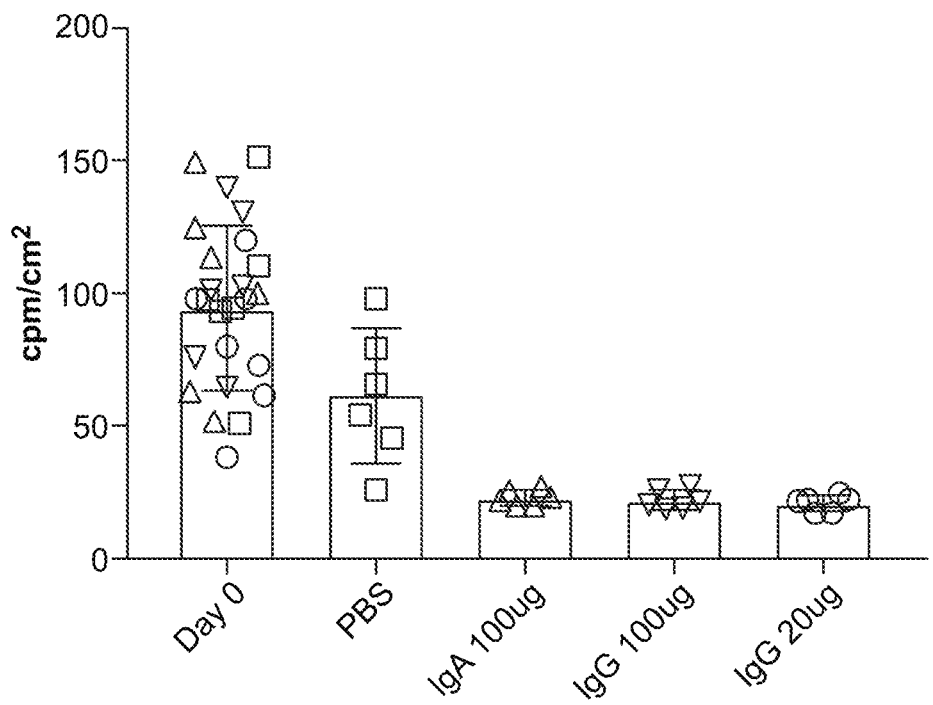

Finally, we analyzed the capacity of the antibodies to kill GD2 expressing cells in vivo in 2 syngeneic mouse models. As a model for a localized tumor, animals were intraperitoneally injected with EL4 cells naturally expressing GD2. After 24 hours of outgrowth, animals were treated with IgA1 or IgG1. Outgrowth of tumor cells was evaluated 24 hours after injection of the antibody. Although both antibodies reduced the average tumor burden treatment with IgA which has only one of the two effector mechanisms, was more effective (FIG. 17A). In a second systemic mouse model, we assessed tumor cell killing for a longer period of time. EL4 cells were intravenously injected). Shortly after injection of cells, tumor cells localized to the lungs, as observed with bioluminescent imaging (Data not shown). After three days of treatment, both IgA1 and IgG1 cleared the tumor cells, while cells were still present in mice treated with PBS (FIG. 17B) Outgrowth was observed in the abdomen of the mice by bioluminescent imaging (data not shown).

Anti GD2-IgA1 does not Induce Pain

A major limitation of IgG1 antibodies directed against GD2 is the increased sensitivity to light touch after treatment. To test whether the lack of complement activation by IgA would mitigate this problem, we conducted in vivo pain experiments in mice. Paw retraction thresholds after stimulation with von Frey hairs were determined as a measure for allodynia.

Figure 18A:
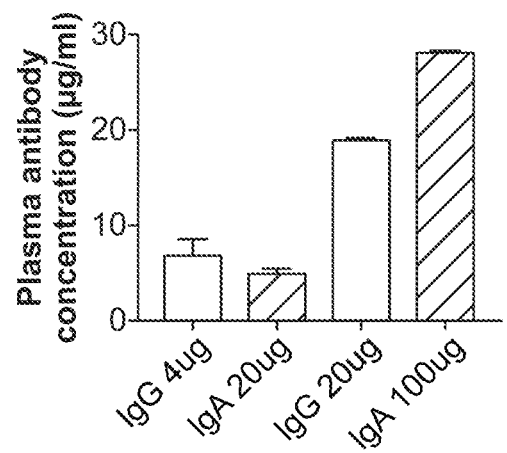
FIG. 18: Neuronal exposure of to IgA1 does not lead to decreases in mechanical withdrawal thresholds. (A) Plasma concentrations of IgA1 and IgG1 ch14.18 3 hours after intravenous injection. (B) Von-Frey withdrawal thresholds. (C) Von-Frey withdrawal thresholds after I.V. injection of fluorescently labeled IgA1 ch14.18 or IgG1 ch14.18. (D) Left column: Visualization of intravenously injected Alexa-488 labeled antibodies on sciatic nerves. Right column: Visualization of ex-vivo staining of GD2 by incubation of neurons with Alexa-549 labeled IgG1 ch14.18.
Figure 18B:
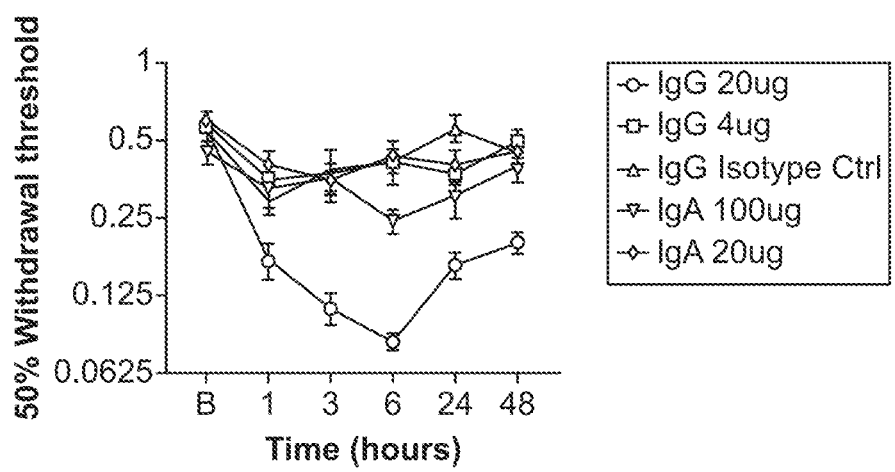
Figure 18C:
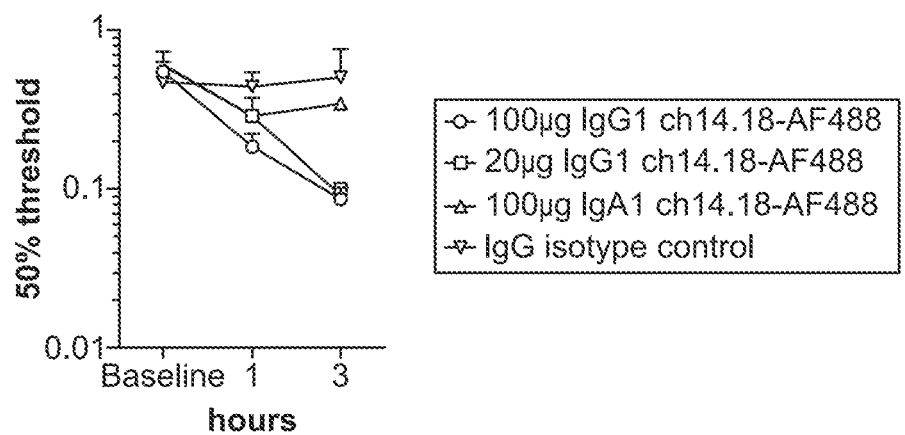
Figure 18D:
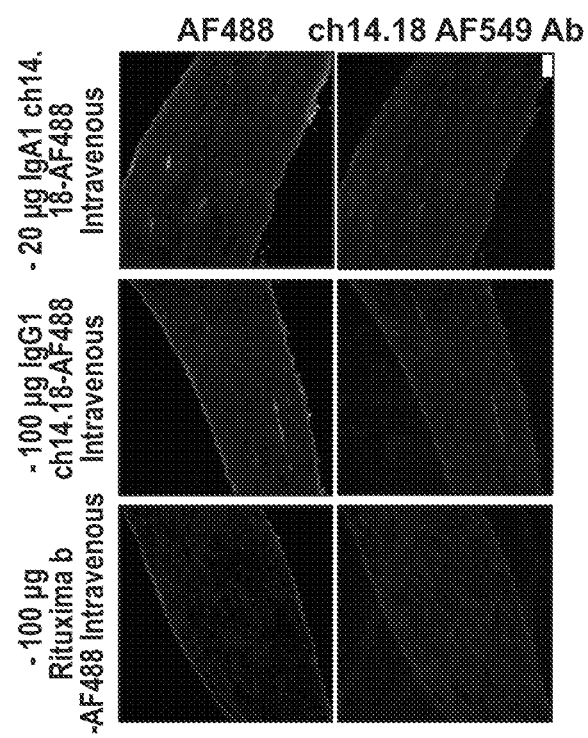

To correct for differences between the half-life of IgA1 and IgG1, mice were intraperitoneally injected with either a low dose of IgG1 (20 μg), corresponding to a dose of 100 μg of IgA at 24 hours or a high dose of IgG1 (100 μg) (FIG. 18A). The antibody concentration found back in the serum after 24 hours is in line with the clinical phenotype after ch14.18 treatment. Treatment with 20 μg of IgG1 ch14.18 showed a significant decrease in withdrawal threshold, which returned to baseline after 48h. A sub-therapeutic dose of IgG1 (4 μg) did not lead to a significant reduction in withdrawal threshold. Different from IgG1, all tested doses of IgA1 did not decrease the paw retraction threshold, indicating that IgA1 does not induce allodynia at levels comparable with IgG (FIG. 18B). Similar results were obtained when fluorescently labeled IgA1 and IgG1 ch14.18 antibodies were injected intravenously. Here, IgG1 ch14.18 also reduced the withdrawal threshold, while IgA1 ch14.18 did not (FIG. 18C. Subsequently, binding of the antibodies was assessed on the sciatic nerve. Antibody exposure was observed with 20 μg of IgG1 and 100 μg of IgA1 ch14.18 to a similar extent and corresponded to the amount of antibody present in the serum (FIG. 18D). The anti-CD20 antibody rituximab was not detected on sciatic nerves. Ex vivo staining of GD2 overlapped with the signal from directly labeled antibodies.

Kits

Provided herein are kits comprising compositions of engineered antibody or fragments thereof. Disclosed herein can also be kits for the reduction of a complement response, such as reducing complement activation, Disclosed herein can also be kits for the treatment of a cancer, pathogen infection, immune disorder or allogeneic transplant. In one embodiment, a kit can include a therapeutic or prophylactic composition containing an effective amount of an engineered antibody in unit dosage form. In some embodiments, a kit comprises a sterile container which can contain a therapeutic composition of engineered antibodies or fragments thereof; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, engineered antibodies and fragments thereof can be provided together with instructions for administering the antibody or fragment thereof to a subject having or at risk of developing a toxicity, complement-associated toxicity, cancer, pathogen infection, immune disorder or allogeneic transplant. Instructions can generally include information about the use of the administration how to utilize the composition to treat toxicity, a side effect, cancer, pathogen infection, immune disorder or allogeneic transplant.

Discussion

The approval of ch14.18 for high-risk neuroblastoma led to improvements in the survival of neuroblastoma patients. Nevertheless, IgG1 antibody therapy for neuroblastoma comes with a major limitation: presence of severe side effects such as neuropathic pain and allodynia. We investigated whether changing the isotype of ch14.18 from IgG1 to IgA1 would abrogate this antibody-induced allodynia.

The present invention shows that IgA1 ch14.18 offers surprisingly strong anti-tumoral effects through neutrophil mediated ADCC and does not induce allodynia in vivo. Blocking the C5a receptor with an antagonist completely stopped allodynia (Sorkin et al 2010, Pain 149(1): 135-142). Thus far, several approaches were undertaken to amend side-effects caused by ch14.18. A first approach was to mutate the C1q-binding site of ch14.18 (K322A). This mutation is thought to abrogate complement activation of ch14.18 (Sorkin et al 2010, Pain 149(1): 135-142). This approach only reduced complement activation, and, as a result, residual pain remained. Also in a phase I clinical trial with this antibody, grade 3-4 toxicity in the form of pain occurred in 68% of patients (Navid et al 2014, J Clin Oncol 32(14): 1445-1452).

Another approach to circumvent ch14.18 induced allodynia was performed by targeting a differentially glycosylated variant of GD2 (0-acetyl-GD2), which is solely present on neuroblastoma cells and not on peripheral nervous tissue by the antibody c.8B6 (Terme et al 2014, PLoS One 9(2): e87210). The antibody c.8B6 does not induce complement activation around pain fibers, however, this antibody is likely less effective.

During the first reports on 14.18, the parental mouse-antibody where ch14.18 is derived from, it was noted that granulocytes mediated effects against neuroblastoma (Bruchelt et al (1989); Immunol Lett 22(3): 217-220). Later, it was shown that their killing potential could be enhanced with the addition of GM-CSF. In clinical studies, it was found that the activation of granulocytes is an indicator for a good outcome of antibody therapy against neuroblastoma (Cheung et al (2012); J Clin Oncol 30(4): 426-432). Besides co-treatment with GM-CSF, there has been a lack of approaches to further engage this target cell population for therapeutic purposes.

Next to an inherent vulnerability of neuroblastoma cells to neutrophil mediated killing, the timing of the current treatment protocol also favors an approach were neutrophils are used as effector cells. Now, patients are prescribed with a myeloablative regimen after which autologous stem cell transplantation follows (Yu et al. (2010). N Engl J Med 363(14): 1324-1334). Shortly thereafter, the immunotherapeutic protocol is started. Neutrophils are often the first leukocyte population which is restored to physiological levels and are therefore are an attractive leukocyte subset to active in such an immune-compromised state. Less than 25% of patients reached proper immune reconstitution for NK cells at the moment of immunotherapy (Nassin et al 2018, Biol Blood Marrow Transplant 24(3): 452-459). With an approach where neutrophils instead of NK cells are addressed, therapeutic variability will be reduced.

In the present invention it was found that IgA mediated killing was improved by the addition of GM-CSF.

IL-2 does not seem to improve IgA or IgG mediated killing. IL-2 was added to the clinical regimen after effects were seen in GD2-expressing melanoma and sarcoma patients which were treated with ch14.18. However, the effects of IL-2 on neuroblastoma therapy remain unclear. This is further stressed by the clinical trial which compared immunotherapy with and without IL-2 (Ladenstein et al 2013 MAbs 5(5): 801-809). The authors show that the addition of IL-2 did not have significant effects on EFS or OS and that early termination because of toxicity was significantly higher in the IL-2 arm.

Although IgA1 lacks a C1q binding site, complement activation of IgA has been documented. The MBL pathway was shown to be activated by polymeric IgA, while the classical complement pathway was triggered for monomeric IgA directed against CD20 (Roos et al; 2001; J Immunol 167(5): 2861-2868 and Lohse, Loew et al; 2018; Br J Haematol 181(3): 413-417). Nevertheless, IgA1 ch14.18 did not induce CDC of neuroblastoma cell lines and did not induce complement-dependent allodynia in mice.

Although allodynia can be solved with IgA, complement as an effector mechanism is also lost. In the present invention it was surprisingly shown that the expected loss of therapeutic effect did not occur. In the in vivo tumor models we indeed see that IgA is at least as efficient as IgG in killing tumor cells. In vivo complement consumption by anti-GD2 antibody has been demonstrated, indicating that complement activation does take place (Cheung at al 2014, Int J Cancer 135(9): 2199-2205).

In our studies, we dosed mice with 5 times the amount of IgA compared to IgG1 to adjust for the difference in half-life between the two antibodies in mice. A similar neuronal exposure and serum concentration could be achieved with the two antibodies. For longer models, multiple doses of IgA1 were injected to account for this. Although the in vivo half-life of IgA is approximately a week in humans, several approaches can be undertaken to improve the half-life of IgA in mice to improve future comparisons (Morell et al, 1973, Clin Exp Immunol 13(4): 521-528). The glycosylation of IgA can be reduced to decrease clearance by binding to the asialoglycoprotein receptor. Silencing of multiple IgA glycosylation sites was already accomplished before, leading to improved pharmacokinetics (Lohse et al, 2016, Cancer Res 76(2): 403-417). Contrary to IgG, IgA does not interact with the neonatal Fc receptor (FcRn). Therefore, antibodies pinocytosed by endothelial cells are degraded via the lysosomal pathway. Both albumin and IgG1 antibodies are rescued from degradation by binding to this receptor. IgA was previously modified to facilitate FcRn binding by introduction of a C-terminal albumin-binding site, which improved its pharmacokinetic profile and anti-tumor effects (Meyer et al, 2016 MAbs 8(1): 87-98).

The present invention shows that ch14.18 IgA offers both the benefit of overcoming allodynia and improved neutrophil activation in a single molecule. Our preclinical data shows that IgA can be dosed higher than IgG without side effects.

Material and Methods

Antibody Production, Isolation and Quality Control

The variable heavy and light chain sequences of ch14.18 were derived from Biologic License Application 125516. The variable heavy chain sequences were cloned into Lonza expression vectors (pEE14.4), coding for the IgA1 or IgG1 heavy chain while the variable light chain sequences were cloned into Lonza expression vectors (pEE14.4) coding for the kappa light chain. Monomeric antibodies were produced by transient transfection of HEK293F cells with vectors coding for the heavy chain, light chain and pAdvantage (accession number U47294; promega), using 293Fectin transfection reagent according to the manufacturer's instructions. IgG1 antibodies were purified using protein A columns (Hi-trap protein A) coupled to an ÄKTAprime plus chromatography system (GE lifesciences). Bound antibody was eluted with 0.1M sodium acetate pH 2.5 and neutralized with 1M TRIS-HCl pH 8.8. The eluate was dialyzed against PBS. IgA1 antibodies were purified using kappa light chain affinity chromatography columns (Hi-trap kappaSelect) and eluted with 0.1M glycine buffer pH 2.5. The eluate was applied on a SEC column ran with PBS as mobile phase. The fractions containing monomeric IgA were collected and concentrated with 100 KDa spin columns. All antibodies were filtered over 0.22 µm filters. Purity and stability of the antibodies was analyzed by HP-SEC (Yarra 3u SEC-2000 column) with 100 mM sodium phosphate, 150 mM NaCl pH 6.8 as mobile phase with detection at 280 nm.

Fluorescent Labeling of Antibodies

Purified antibodies were labelled with fluorescein by incubation at room temperature for 2 h with N-hydroxy-succimidyl-FITC while stirring. Unbound NHS-fluorescein was removed by using sephadex columns (NAP-5, GE-healthcare), according to the manufacturer's instructions. Antibodies were labelled with alexa fluor-488 antibody labeling kit (ThermoFisher) according to the manufacturer's instructions.

Cell Lines

All neuroblastoma cell lines were cultured in DMEM culture medium supplemented with HEPES, glutamax, 10% fetal calf serum, 1× penicillin and streptomycin at 37° C. in a humidified incubator containing 5% $CO_2$. HEK293F cells were cultured in FreeStyle 293 expression medium at 37° C. in a humidified incubator with orbital shaker platform containing 8% CO2.

Binding Assays 100.000 neuroblastoma cells were plated out in 96 well plates and centrifuged for 2 minutes at 1500 RPM. Cells were washed and incubated with fluorescein-labelled antibody at several concentrations for 45 minutes. Next, cells were centrifuged for 2 minutes at 1500 RPM, washed and resuspended in PBS. The amount of bound antibody to the cells was quantified by flow cytometry (BD FacsCanto II, BD).

Cell Based Affinity Measurements $1 \times 10^6$ IMR32 neuroblastoma cells were plated out on the side of a 10 cm culture dish in an elliptical shape and incubated overnight for attaching to the plate. Subsequently, plates were washed with culture medium and transferred to the LigandTracer apparatus (Ridgeview instruments). 10 nM of fluorescein-labelled antibody was added to the cells and association was measured for 1 hour. Afterwards, antibody concentration was increased to 20 nM to assess association at higher antibody concentrations for 1 hour. Finally, dissociation was measured by replacing the antibody containing solution for medium without antibody and dissociation was measured for 2 hours. The affinity of the antibodies was calculated via TraceDrawer software (Ridgeview instruments).

ADCC Assays

ADCC was quantified as described previously (Brandsma et al; 2015; Cancer Immunol Res 3(12): 1316-1324) In short, target cells with or without pre-treatment of 10 μM 11-cis-retinoic acid for 24 hours were labeled with 3.7 MBq $^{51}$Cr for 2 hours. Afterwards, cells were washed three times to remove excess chromium. Blood for ADCC's was obtained from healthy donors at the UMC Utrecht. For leukocyte isolation, blood was incubated with demiwater for 30 seconds to lyse erythrocytes. Afterwards, 10×PBS was added to restore physiological osmolality. Cells were washed in medium and resuspended in medium corresponding to the original blood volume. The number of leukocytes used per well corresponds to the number of leukocytes present in 50 μl of blood before lysis. For PMN and PBMC isolation, blood was added on top of Ficoll/Histopaque 1119 layers and centrifuged for 25 minutes at 1500 RPM without braking. Afterwards, PBMC's and PMN's were collected from the interphase between serum and ficoll or in the histopaque layer respectively. The effector-to-target (E:T) ratios were 80:1 for PBMCs, 40:1 for PMNs. Effector cells, antibodies at various concentration, GM-CSF and IL-2 and radioactively labeled tumor cells were added to round-bottom microtiter plates (Corning Incorporated) and incubated for 37° C. in a humidified incubator containing 5% $CO_2$. Plates were centrifuged for 2 minutes at 1500 RPM and 50 μl of the supernatant was transferred to lumaplates. Radioactive signal (in cpm) was quantified in a beta-gamma counter. Specific lysis was calculated using the formula: ((Experimental cpm−basal cpm)/(maximal cpm−basal cpm))×100, with maximal lysis determined by incubating labelled cells with 2.5% triton and basal release was determined in the absence of antibodies and effector cells.

CDC Assays $10^5$ neuroblastoma cells were added to microtiter plates and incubated for 30 minutes with antibodies at various concentrations at room temperature. Afterwards, pooled human serum (from 8 different healthy donors) was added to a concentration of 15% and incubated for 1 hour or 4 hours. Afterwards, cells were washed and stained with 7-AAD for 15 minutes. 7-AAD uptake, representing cell lysis was quantified by flow cytometry.

Antibody Concentration Determination in Mouse Serum

MaxiSorp 96 well ELISA plates were coated overnight with 0.5 μg/ml goat IgG anti-human kappa diluted in PBS. Next, plates were washed three times with 0.05% TWEEN 20 in PBS (PBST) and blocked for 1 hour by incubating with 1% BSA in PBST. Serum samples were diluted 1:2000 in 1% BSA in PBST and added to the wells and incubated for 1.5 at room temperature. Next, plates were washed three times with PBST. HRP-labeled-anti-human IgA or -IgG were used to bind human IgA or human IgG respectively. Plates were developed for 10 minutes with 2,2'-azino-bis(3-ethylbenzo-thiazoline-6-sulphonic acid (ABTS) and read out on a spectrophotometer at 415 nm.

Animals and Animal Experiments

Mice were maintained in the animal facility of the University of Utrecht. Experiments were conducted using both male and female C57BL/6 mice (Janvier) Mice were housed in groups under a 12:12 light dark cycle, with food and water available ad libitum. Mice were acclimatized for at least 1 week prior to the start of experiment. Sample sizes were calculated with power analysis at the time of the design of experiments.

Mechanical thresholds were determined using the von Frey test in mice after intravenous injection with IgG1 ch14.18, IgA1 ch14.18 or fluorescently labeled variants thereof. (Stoelting, Wood Dale, IL, US) with the up-and-down method as was described before previously (Eijkelkamp et al; 2016; J Neurosci 36(28): 7353-7363. In brief, mechanical nociception was tested with a calibrated von Frey hair monofilament (Stoelting). First, mice were acclimated for 15 to 20 min in a transparent box with a metal mesh floor. The von Frey hair monofilament was applied through the mesh floor to the plantar skin of the hindpaw. Mechanical nociception was measured as the total number of paw withdrawals in response to a series of six applications of a 0.02 mg von Frey hair, which does not elicit a response in untreated animals (Alessandri-Haber et al., 2006; J Neurosci. 2006 Apr. 5; 26(14):3864-74.). In experiments, the average of the left and right paw was considered as an independent measure. To minimize bias, animals were randomly assigned to the different groups prior to the start of experiment, and all experiments were performed by experimenters blinded to treatment. At the end of the experiments, mice were euthanized by cervical dislocation. Mechanical thresholds were assessed for 48 hours.

For evaluating the in vivo efficacy of antibodies, mice were injected intraperitoneally with $5 \times 10^6$ GD2 expressing EL4 cells expressing (ATCC). After 1 day, mice were intraperitoneally injected with 100 μg of IgG1 ch14.18, or 100 μg of IgA1 ch14.18. After 2 days, blood was taken and mice were injected with luciferin and subjected to bioluminescence analysis. Afterwards mice were euthanized by cervical dislocation.

GD2 antibody binding to neurons was visualized by i.v. injection of 20 μg or 100 μg alexa-488 labeled IgG1 ch14.18 or 20 μg of IgA1 ch14.18. Sciatic nerves were isolated and 10 μm thick slices were prepared with a cryostat cryotome and placed on slides. Slides were fixed for 10 minutes in 4% PFA and washed. Finally, slides were counterstained with DAPI, washed and treated with fluorsave. Slides were dried overnight at 4° C. and images were taken by fluorescence microscopy.

The invention claimed is:

1. An engineered antibody that comprises:
 (a) an IgG variable region that comprises:
  (i) a heavy chain variable domain that comprises:
   a complementarity determining region 1 (CDR1) comprising an amino acid sequence GSSFTGYN (SEQ ID NO: 14),
   a complementarity determining region 2 (CDR2) comprising an amino acid sequence IDPYYGGT (SEQ ID NO: 15), and
   a complementarity determining region 3 (CDR3) comprising an amino acid sequence VSGMEY (SEQ ID NO: 16), and
  (ii) a light chain variable domain that comprises:
   a complementarity determining region 1 (CDR1) comprising an amino acid sequence QSLVHRNG-NTY (SEQ ID NO: 17),
   a complementarity determining region 2 (CDR2) comprising an amino acid sequence KVS (SEQ ID NO: 18), and
   a complementarity determining region 3 (CDR3) comprising an amino acid sequence of QSTHVP-PLT (SEQ ID NO: 19); and
 (b) a heavy chain constant region that comprises an IgA CH1 heavy chain constant domain, an IgA CH2 heavy chain constant domain, an IgA hinge domain, and an IgA CH3 heavy chain constant domain, wherein the heavy chain constant region comprises:
  (ii) an amino acid substitution at N337 according to Bur scheme corresponding to N207 of SEQ ID NO: 11; I338 according to Bur scheme corresponding to I208 of SEQ ID NO: 11; and T339 according to Bur scheme corresponding to T209 of SEQ ID NO: 11,
  (ii) an amino acid substitution at N166 according to Bur scheme corresponding to N49 of SEQ ID NO: 11,
  (iii) an amino acid substitution at P221 according to Bur scheme corresponding to P104 of SEQ ID NO: 11,
  (iv) an amino acid substitution at C311 according to Bur scheme corresponding to C181 of SEQ ID NO: 11,
  (v) a deletion of amino acid C471 according to Bur scheme corresponding to C341 of SEQ ID NO: 11,
  (vi) a deletion of amino acid Y472 according to Bur scheme corresponding to Y342 of SEQ ID NO: 11, or
  (vii) a combination thereof.

2. The engineered antibody of claim 1, wherein the heavy chain variable domain comprises an amino acid sequence of SEQ ID NO: 3, and wherein the light chain variable domain comprises an amino acid sequence of SEQ ID NO: 4.

3. The engineered antibody of claim 1, wherein the IgA CH1 heavy chain constant domain, the IgA CH2 heavy chain constant domain, the IgA hinge domain, and the IgA CH3 heavy chain constant domain are human IgA CH1, CH2, and CH3 heavy chain constant domains.

4. The engineered antibody of claim 1, wherein the IgA CH1 heavy chain constant domain, the IgA CH2 heavy chain constant domain, the IgA hinge domain, and the IgA CH3 heavy chain constant domain are IgA1 CH1, CH2, and CH3 heavy chain constant domains, or IgA2 CH1, CH2, and CH3 heavy chain constant domains.

5. The engineered antibody of claim 1, wherein the heavy chain constant region comprises:
 (i) a N337T amino acid substitution at N337 according to Bur scheme, wherein said N337 corresponds to N207 of SEQ ID NO: 11, a I338L amino acid substitution at I338 according to Bur scheme, wherein said I338 corresponds to I208 of SEQ ID NO: 11, and a T339S amino acid substitution at T339 according to Bur scheme, wherein said T339 corresponds to T209 of SEQ ID NO: 11,
 (ii) a N166G amino acid substitution at N166 according to Bur scheme, wherein said N166 corresponds to N49 of SEQ ID NO: 11,
 (iii) a P221R amino acid substitution at P221 according to Bur scheme, wherein said P221 corresponds to P104 of SEQ ID NO: 11,
 (iv) a C311S amino acid substitution at C311 according to Bur scheme, wherein said C311 corresponds to C181 of SEQ ID NO: 11,
 (v) a deletion of amino acid C471 according to Bur scheme corresponding to C341 of SEQ ID NO: 11,
 (vi) a deletion of amino acid Y472 according to Bur scheme corresponding to Y342 of SEQ ID NO: 11, or
 (vii) a combination thereof.

6. The engineered antibody of claim 1, wherein the engineered antibody exhibits increased antibody-dependent cell mediated cytotoxicity (ADCC) relative to a corresponding IgG antibody as measured in a suitable in vitro ADCC assay.

7. The engineered antibody of claim 1, wherein the engineered antibody exhibits decreased complement-dependent cytotoxicity (CDC) relative to a corresponding IgG antibody as measured in a suitable in vitro CDC assay.

\* \* \* \* \*